(12) United States Patent
Cook et al.

(10) Patent No.: US 8,293,917 B2
(45) Date of Patent: Oct. 23, 2012

(54) PYRAZOLE COMPOUNDS AS CCR1 ANTAGONISTS

(75) Inventors: Brian Nicholas Cook, Danbury, CT (US); Christian Harcken, New Milford, CT (US); Thomas Wei-Ho Lee, Lexington, MA (US); Pingrong Liu, Southbury, CT (US); Jord Lord, Poughkeepsie, NY (US); Can Mao, New Milford, CT (US); Wang Mao, Milford, CT (US); Brian Christopher Raudenbush, Beacon Falls, CT (US); Hossein Razavi, Danbury, CT (US); Christopher Ronald Sarko, New Milford, CT (US); Alen David Swinamer, Woodbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 87 days.

(21) Appl. No.: 12/990,248

(22) PCT Filed: May 1, 2009

(86) PCT No.: PCT/US2009/042455
§ 371 (c)(1),
(2), (4) Date: Nov. 8, 2010

(87) PCT Pub. No.: WO2009/137338
PCT Pub. Date: Nov. 12, 2009

(65) Prior Publication Data
US 2011/0230521 A1    Sep. 22, 2011

Related U.S. Application Data

(60) Provisional application No. 61/050,693, filed on May 6, 2008.

(51) Int. Cl.
*C07D 401/00*    (2006.01)
*A61K 31/44*    (2006.01)
(52) U.S. Cl. ..................... 546/275.4; 514/341
(58) Field of Classification Search ........................ None
See application file for complete search history.

(56) References Cited

U.S. PATENT DOCUMENTS

| | | |
|---|---|---|
| 4,999,363 A | 3/1991 | Oshima et al. |
| 5,118,701 A | 6/1992 | Oshima et al. |
| 5,242,931 A | 9/1993 | Oshima et al. |
| 5,302,596 A | 4/1994 | Oshima et al. |
| 5,534,481 A | 7/1996 | Suzuki et al. |
| 5,612,360 A | 3/1997 | Boyd et al. |
| 5,616,537 A | 4/1997 | Yokota et al. |
| 5,670,452 A | 9/1997 | Suzuki et al. |
| 5,760,028 A | 6/1998 | Jadhav et al. |
| 5,763,616 A | 6/1998 | Suzuki et al. |
| 5,770,544 A | 6/1998 | Yokota et al. |
| 5,973,156 A | 10/1999 | Chambers et al. |
| 6,025,374 A | 2/2000 | Castro Pineiro et al. |
| 6,107,321 A | 8/2000 | Madin |
| 6,211,219 B1 | 4/2001 | MacLeod et al. |
| 6,326,382 B1 | 12/2001 | Villalobos et al. |
| 6,331,640 B1 | 12/2001 | Fotouhi et al. |
| 6,498,255 B2 | 12/2002 | Villalobos et al. |
| 6,716,978 B2 | 4/2004 | Marfat |
| 6,784,182 B2 | 8/2004 | Liebeschuetz et al. |
| 6,803,384 B2 | 10/2004 | Fotouhi et al. |
| 6,855,715 B1 | 2/2005 | Liebeschuetz et al. |
| 6,878,725 B2 | 4/2005 | Liebeschuetz et al. |
| 6,900,196 B2 | 5/2005 | Liebeschuetz et al. |
| 6,936,611 B2 | 8/2005 | Liebeschuetz et al. |
| 7,049,297 B2 | 5/2006 | Zhang et al. |
| 7,053,078 B2 | 5/2006 | Liebeschuetz et al. |
| 7,129,264 B2 | 10/2006 | Smallheer et al. |
| 7,223,782 B2 | 5/2007 | Atkinson et al. |
| 7,429,609 B2 | 9/2008 | Ohi et al. |
| 7,879,873 B2 | 2/2011 | Cook et al. |

(Continued)

FOREIGN PATENT DOCUMENTS
EP        345747 A2    12/1989
(Continued)

OTHER PUBLICATIONS

Finar, I. J. Chem Soc. Sec. C 1969 pp. 1495-1499.*
Carter, P.N. et al., "N-aryl pyrazoles,indazoles and azaindazoles as antagonists of CC chemokine receptor 1: patent cooperation treaty applications WO2010036632, WO2009134666 and WO2009137337". Expert Opinion Ther. Patents, 2010, 20(11), p. 1-10.
International Search Report for PCT/US2009/042455 mailed Jul. 13, 2009 and Written Opinion.

(Continued)

*Primary Examiner* — Janet Andres
*Assistant Examiner* — Heidi Reese
(74) *Attorney, Agent, or Firm* — Michael P. Morris; Anthony P. Bottino

(57) ABSTRACT

Disclosed are compounds of the formula (I) which block the interaction of CCR1 and its ligands and are thus useful for treating a variety of diseases and disorders that are mediated or sustained through the activity of CCR1 including autoimmune diseases, such as rheumatoid arthritis and multiple sclerosis. Also disclosed are pharmaceutical compositions comprising these compounds, methods of using these compounds in the treatment of various diseases and disorders, processes for preparing these compounds and intermediates useful in these processes.

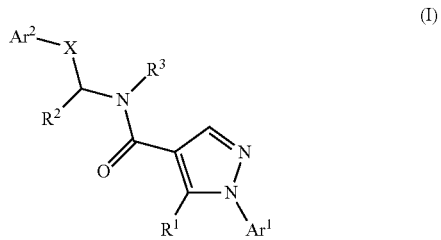

(I)

9 Claims, No Drawings

U.S. PATENT DOCUMENTS

| | | | |
|---|---|---|---|
| 8,063,065 | B2 | 11/2011 | Cook et al. |
| 2002/0037860 | A1 | 3/2002 | D'Andrea et al. |
| 2002/0052373 | A1 | 5/2002 | Zorn et al. |
| 2004/0127536 | A1 | 7/2004 | Bhagwat et al. |
| 2005/0009876 | A1 | 1/2005 | Bhagwat et al. |
| 2005/0020564 | A1 | 1/2005 | Atkinson et al. |
| 2005/0108582 | A1 | 5/2005 | Fung |
| 2005/0208582 | A1 | 9/2005 | Ohi et al. |
| 2005/0261339 | A1 | 11/2005 | Ohi et al. |
| 2006/0252781 | A1 | 11/2006 | Basarab et al. |
| 2006/0281739 | A1 | 12/2006 | Gadek et al. |
| 2007/0004761 | A1 | 1/2007 | Basarab et al. |
| 2008/0262040 | A1 | 10/2008 | Callahan et al. |
| 2009/0054397 | A1 | 2/2009 | Ohi et al. |
| 2010/0093724 | A1 | 4/2010 | Cook et al. |
| 2011/0034512 | A1 | 2/2011 | Disalvo et al. |
| 2011/0086846 | A1 | 4/2011 | Cook et al. |
| 2011/0137042 | A1 | 6/2011 | Razavi et al. |
| 2011/0230521 | A1 | 9/2011 | Cook et al. |
| 2011/0294808 | A1 | 12/2011 | Kuzmich et al. |
| 2012/0035370 | A1 | 2/2012 | Cook et al. |
| 2012/0136158 | A1 | 5/2012 | Cook et al. |

FOREIGN PATENT DOCUMENTS

| | | | |
|---|---|---|---|
| EP | 1201268 | A2 | 5/2002 |
| JP | 10001478 | A | 1/1998 |
| WO | 9217475 | A1 | 10/1992 |
| WO | 9401415 | A1 | 1/1994 |
| WO | 9500509 | | 5/1995 |
| WO | 9617842 | A1 | 6/1996 |
| WO | 9711945 | A1 | 4/1997 |
| WO | 9719073 | A1 | 5/1997 |
| WO | 9723480 | A1 | 7/1997 |
| WO | 9803504 | A1 | 1/1998 |
| WO | 9923076 | A1 | 5/1999 |
| WO | 0021920 | A1 | 4/2000 |
| WO | 0076970 | A2 | 12/2000 |
| WO | 0076971 | A2 | 12/2000 |
| WO | 0100656 | A2 | 1/2001 |
| WO | 0210137 | A2 | 2/2002 |
| WO | 03087085 | A1 | 10/2003 |
| WO | 03101968 | A1 | 12/2003 |
| WO | 03105853 | A1 | 12/2003 |
| WO | 2004043924 | A1 | 5/2004 |
| WO | 2004056831 | A1 | 7/2004 |
| WO | 2004094372 | A2 | 11/2004 |
| WO | 2005016929 | A1 | 2/2005 |
| WO | WO 2005061462 | A2 * | 7/2005 |
| WO | 2006091496 | A2 | 8/2006 |
| WO | 2006125119 | A1 | 11/2006 |
| WO | 2007002293 | A2 | 1/2007 |
| WO | 2007028083 | A2 | 3/2007 |
| WO | 2007102883 | A2 | 9/2007 |
| WO | 2008011131 | | 1/2008 |
| WO | 2009024585 | A2 | 2/2009 |
| WO | 2009037570 | A2 | 3/2009 |
| WO | 2009134666 | A1 | 11/2009 |
| WO | 2009137338 | A1 | 11/2009 |
| WO | 2010036632 | A1 | 4/2010 |
| WO | 2011049917 | A1 | 4/2011 |
| WO | 2011056440 | A1 | 5/2011 |
| WO | 2011071730 | A1 | 6/2011 |
| WO | 2011137109 | A1 | 11/2011 |

OTHER PUBLICATIONS

Alzheimer's Disease. Retrieved online Dec. 15, 2010. http:/www.cnn.com/HEALTH/mentalhealt/alzheimers.

CAPLUS: 1990:478384, Bruneau, 1990.

CAPLUS: 2008:94643, Kitamura, 2008.

CAPLUS: 2009:583109, Doherty, 2009.

Cheng, J-F, et al., "CCR1 Antagonists". Molecular Diversity, Kluwer Academic Publishers, vol. 12, No. 1, Jun. 17, 2008, p. 17-23.

Conlon, K. et al., "Comparison of lymphokine secretion and mRNA expression in the CD45RA+ and CD45RO+ subsets of human peripheral blood CD4+ and CD8+ lympocytes". European Journal of Immunology, 1995, vol. 25, p. 644-648.

Gerard, C. et al., "Chemokines and disease". 2001 Nature Publishing Group, Chemokine Reviews, Nature Immunology, vol. 2, No. 2, Feb. 2001, p. 108-115.

Haringman, J.J. et al., "Chemokine blockade and chronic inflammatory disease: proof of concept in patients with rheumatoid arthritis". Ann Rheum Dis, 2003, 62, p. 715-721.

Karpus, W. J. et al., "An Important Role for the Chemokine Macrophase Inflammatory Protein-1a in the Pathogenesis of the T Cell-Mediated Autoimmune Disease, Experimental Autoimmune Encephalomyelitis". The American Association of Immunologists, 1995, p. 5003-5010.

Koch, A. E., et al., "Macrophase Inflammatory Protein-1a. A Novel Chemotactic Cytokine for Macrophages in Rheumatoid Arthritis". The Journal of Clinical Investigation, Inc., vol. 93, Mar. 1994, p. 921-928.

Koch, A.E. et al., "Epithelial Neutrophil Activating Peptide-78: A Novel Chemotactic Cytokine for Neutrophils in Arthritis". The Journal of Clinical Investigations, Inc. vol. 94, Sep. 1994, p. 1012-1018.

Plater-Zyberk, C. et al., "Effect of a CC chemokine receptor antagonist on collagen induced arthritis in DBA/1 mice". Immunology Letters, 57, 1997, p. 117-120.

Revesz, L. et al., "Novel CCR1 antagonists with oral activity in the mouse collagen induced arthritis". Bioorganice and Medicinal Chemistry Letters, 2005, p. 1-5.

Trebst, C. et al., "CCR1+/CCR5+ Mononuclear Phagocytes Accumulate in the Central Nervous System on Patients with Multiple Sclerosis." American Journal of Pathology, Vol, 159, No. 4, Nov. 2001, p. 1701-1710.

Volin, M.V. et al., "RANTES Expression and Contribution to Monocyte Chemotaxix in Arthritis". Clinical Immunology and Immunopathology, vol. 89, No. 1, Oct. 1998, Article II984590, p. 44-53.

Caplus: 2009:2329372, Loiseleur, 2009.

Engbersen, J.F.J. et al., "Synthesis of 2-Aminomethyl-1,10-phenanthroline. A new Chelating Agent and Versatile Synthon for other Chelating Compounds", Journal of Heterocyl Cehm., 1986, vol. 23, pp. 989-990.

* cited by examiner

PYRAZOLE COMPOUNDS AS CCR1 ANTAGONISTS

APPLICATION DATA

This application claims benefit to U.S. provisional application Ser. No. 61/050,693 filed May 6, 2008.

FIELD OF THE INVENTION

This invention relates to pyrazoles which are useful as antagonists of CCR1 mediated activity and are thus useful for treating a variety of diseases that are mediated through CCR1 activity including autoimmune diseases such as rheumatoid arthritis and multiple sclerosis. The invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemotactic Cytokine Receptor 1 (CCR1) belongs to a large family (>20) of chemotactic cytokine (chemokine) receptors that interact with specific chemokines (>50) to mediate leukocyte trafficking, granule exocytosis, gene transcription, mitogenic effects and apoptosis. Chemokines are best known for their ability to mediate basal and inflammatory leukocyte trafficking. The binding of at least three chemokines (MIP-1 alpha/CCL3, MCP3/CCL7 and RANTES/CCL5) to CCR1 is responsible for the trafficking of monocytes, macrophages and TH1 cells to inflamed tissues of rheumatoid arthritis (RA) and multiple sclerosis (MS) patients (Trebst et al. (2001) American J of Pathology 159 p. 1701). Macrophage inflammatory protein 1 alpha (MIP-1 alpha), macrophage chemoattractant protein 3 (MCP-3) and regulated on activation, normal T-cell expressed and secreted (RANTES) are all found in the CNS of MS patients, while MIP-1 alpha and RANTES are found in the CNS in the experimental autoimmune encephalomyelitis (EAE) model of MS (Review: Gerard and Rollins (2001) Nature Immunology). Macrophages and Th1 cells in the inflamed synovia of RA patients are also major producers of MIP-1 alpha and RANTES, which continuously recruit leukocytes to the synovial tissues of RA patients to propagate chronic inflammation (Volin et al. (1998) Clin. Immunol. Immunopathology; Koch et al. (1994) J. Clin. Investigation; Conlon et al. (1995) Eur. J. Immunology). Antagonizing the interactions between CCR1 and its chemokine ligands is hypothesized to block chemotaxis of monocytes, macrophages and Th1 cells to inflamed tissues and thereby ameliorate the chronic inflammation associated with autoimmune diseases such as RA and MS.

Evidence for the role of CCR1 in the development and progression of chronic inflammation associated with experimental autoimmune encephalitis (EAE), a model of multiple sclerosis, is based on both genetic deletion and small molecule antagonists of CCR1. CCR1 deficient mice were shown to exhibit reduced susceptibility (55% vs. 100%) and reduced severity (1.2 vs. 2.5) of active EAE (Rottman et al. (2000) Eur. J. Immunology). Furthermore, administration of small molecule antagonist of CCR1, with moderate affinity ($K_i$=120 nM) for rat CCR1, was shown to delay the onset and reduce the severity of EAE when administered intravenously (Liang et al. (2000) J. Biol. Chemistry). Treatment of mice with antibodies specific for the CCR1 ligand MIP1alpha have also been shown to be effective in preventing development of acute and relapsing EAE by reducing the numbers of T cells and macrophages recruited to the CNS (Karpus et al. (1995) J. Immunology; Karpus and Kennedy (1997) J. Leukocyte Biology). Thus, at least one CCR1 ligand has been demonstrated to recruit leukocytes to the CNS and propagate chronic inflammation in EAE, providing further in vivo validation for the role of CCR1 in EAE and MS.

In vivo validation of CCR1 in the development and propagation of chronic inflammation associated with RA is also significant. For example, administration of a CCR1 antagonist in the collagen induced arthritis model (CIA) in DBA/1 mice has been shown to be effective in reducing synovial inflammation and joint destruction (Plater-Zyberk et al. (1997) Immunology Letters). Another recent publication described potent antagonists of murine CCR1 that reduced severity (58%) in LPS-accelerated collagen-induced arthritis (CIA), when administered orally (Biorganic and Medicinal Chemistry Letters (15 (2005) 5160-5164). Published results from a Phase I clinical trial with an oral CCR1 antagonist demonstrated a trend toward clinical improvement in the absence of adverse side effects (Haringman et al. (2003) Ann. Rheum. Dis.). One third of the patients achieved a 20% improvement in rheumatoid arthritis signs and symptoms (ACR20) on day 18 and CCR1 positive cells were reduced by 70% in the synovia of the treated patients, with significant reduction in specific cell types including 50% reduction in CD4$^+$ T cells, 50% reduction in CD8$^+$ T cells and 34% reduction in macrophages.

Studies such as those cited above support a role for CCR1 in MS and RA and provide a therapeutic rationale for the development of CCR1 antagonists.

BRIEF SUMMARY OF THE INVENTION

The present invention provides novel compounds which block the interaction of CCR1 and its ligands and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest generic aspect the invention provide a compound of the formula

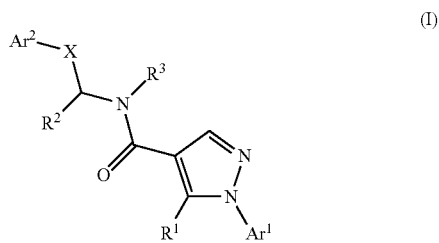

(I)

wherein

Ar$^1$ is carbocycle, heteroaryl or heterocycle each optionally substituted by one to three R$^a$;

X is —(CH$_2$)$_n$—;

Ar$^2$ is carbocycle, heteroaryl or heterocycle each optionally substituted by one to three R$^b$;

R$^1$ is hydrogen or R$^a$, with the proviso that R$^1$ is not CF$_3$ or n-Pr;

R$^2$ is C$_{1-6}$ alkyl, C$_{2-6}$alkenyl, C$_{3-6}$cycloalkyl or phenyl, each optionally substituted by R$^a$;

R$^3$ is hydrogen, C$_{1-6}$ alkyl or C$_{1-6}$alkoxyC$_{1-6}$alkyl;

R$^a$ is C$_{1-6}$ alkyl, C$_{1-6}$alkenyl, C$_{3-10}$ cycloalkyl, C$_{1-6}$ alkoxyC$_{1-6}$ alkyl, C$_{1-6}$ alkylthio, C$_{1-6}$ alkylsulfonyl, C$_{1-6}$ alkoxycarbonyl, hydroxyC$_{1-6}$alkyl, amino, mono-or di-C$_{1-6}$ alkylamino, aminoC$_{1-6}$alkyl, mono-or di-C$_{1-6}$alkylaminoC$_{1-6}$ alkyl, C$_{3-6}$ cycloalkylamino, C$_{1-6}$ alkylaminocarbonyl, C$_{1-6}$ acyl, C$_{1-6}$ acylamino, C$_{1-6}$ dialkylaminocarbonyl, hydroxyl, halogen, cyano, nitro, oxo, R$^4$—S(O)$_m$—NH—, R$^4$—NH—S(O)$_m$—, aryl, carboxyl, aryl(CH$_2$)$_{0-1}$amino, heteroaryl(CH$_2$)$_{0-1}$amino or heterocyclylcarbonyl wherein said heterocycle is optionally substituted with C$_{1-6}$alkyl, each substituent on R$^a$ where possible is optionally halogenated;

R$^b$ is hydroxyl, carboxyl, halogen, —(CH$_2$)$_n$—CN, nitro, oxo, C$_{1-6}$ alkyl, C$_{2-6}$ alkenyl, C$_{2-6}$ alkynyl, C$_{3-10}$ cycloalkyl, C$_{1-6}$ alkoxy, C$_{1-6}$ alkoxycarbonyl, —(CH$_2$)$_n$—NR$^c$R$^d$, R$_4$—S(O)$_m$—, R$^4$—S(O)$_m$—NR$^e$—, R$^4$—NR$^e$—S(O)$_m$—, —NR$^f$—C(O)—R$^e$, —(CH$_2$)$_x$—C(O)—(CH$_2$)$_n$—NR$^c$R$^d$, heterocyclyl, aryl or heteroaryl, each substituent on R$_b$ where possible is optionally halogenated or substituted with 1 to 3 C$_{1-6}$ alkyl, C$_{1-6}$ acyl, C$_{1-6}$ alkoxycarbonyl, C$_{1-6}$ alkyl-S(O)$_m$—, aryl or carboxyl;

each R$^c$, R$^d$ are independently hydrogen, C$_{1-6}$ alkyl, C$_{1-6}$ acyl, C$_{3-10}$ cycloalkyl, C$_{1-6}$ alkoxy, hydroxyC$_{1-6}$ alkyl, C$_{1-6}$ alkylC$_{1-6}$ alkoxy, C$_{1-6}$ alkylsulfonyl, C$_{1-6}$ alkoxycarbonyl or —(CH$_2$)$_n$—NR$^e$R$^f$;

each R$^e$, R$^f$ are independently hydrogen, C$_{1-6}$ alkyl, C$_{3-10}$ cycloalkyl, C$_{1-6}$ alkoxy, hydroxyC$_{1-6}$ alkyl or C$_{1-6}$ acyl;

R$^4$ is hydrogen, C$_{1-6}$ alkyl, C$_{3-10}$ cycloalkyl, heterocyclyl, aryl or heteroaryl each optionally substituted with C$_{1-6}$ alkyl, C$_{1-6}$ alkoxy, halogen, hydroxyl, amino, mono-or di-C$_{1-6}$ alkylamino, C$_{1-6}$ alkoxycarbonyl or C$_{1-6}$ acylamino;

each n, x are independently 0-3;

each m is independently 0-2;

or a pharmaceutically acceptable salt thereof.

In another embodiment, there is provided compounds as described in the embodiment immediately above and wherein:

Ar$^1$ is phenyl optionally substituted by one to three groups selected from C$_{1-6}$alkyl, halogen and C$_{1-6}$alkylSO$_2$—;

X is —(CH$_2$)$_n$—;

Ar$_2$ is phenyl, naphthyl or pyridyl each optionally substituted by one to three R$^b$;

R$^1$ is C$_{1-2}$alkyl, C$_{1-2}$alkoxyC$_{1-2}$alkyl, hydroxyC$_{1-2}$alkyl, aminoC$_{1-2}$alkyl or mono-or di-C$_{1-3}$ alkylaminoC$_{1-2}$alkyl;

R$^2$ is C$_{1-6}$ alkyl, C$_{2-6}$alkenyl, C$_{3-6}$cycloalkyl, C$_{1-6}$ alkoxycarbonylmethyl, hydroxyC$_{2-4}$alkyl, C$_{1-6}$ alkylaminocarbonylmethyl, C$_{1-6}$ dialkylaminocarbonylmethyl, 4-methylpiperidin-1-ylcarbonylC$_{2-4}$alkyl, phenyl(CH$_2$)$_{0-1}$ alkylaminoC$_{4-5}$alkyl or pyridyl(CH$_2$)$_{0-1}$alkylaminoC$_{4-5}$ alkyl;

R$^3$ is hydrogen;

R$^b$ is hydroxyl, halogen, CF$_3$, C$_{1-6}$ alkyl, C$_{1-6}$ alkoxy, R$^4$—S(O)$_m$—, R$^4$—S(O)$_m$—NR$^e$—, R$^4$—NR$^e$—S(O)$_m$—, —NR$^f$—C(O)—R$^e$, or —C(O)—NR$^c$R$^d$;

each R$^c$, R$^d$, R$^e$, R$^f$ are independently hydrogen, C$_{1-6}$ alkyl, C$_{3-10}$ cycloalkyl, hydroxyC$_{1-6}$ alkyl or C$_{1-6}$ acyl;

R$^4$ is hydrogen, tertrahydropyranyl or C$_{1-6}$ alkyl optionally substituted with C$_{1-6}$ alkoxy, C$_{3-6}$ cycloalkyl, halogen, hydroxyl, amino, mono-or di-C$_{1-6}$ alkylamino, C$_{1-6}$ alkoxycarbonyl or C$_{1-6}$ acylamino;

n is 0-1;

each m is independently 0-2.

In a further embodiment, there is provided compounds as described in the embodiment immediately above and wherein:

Ar$^1$ is phenyl optionally substituted by one to three groups selected from methyl, Br, Cl, F and C$_{1-3}$alkylSO$_2$—;

X is a bond;

Ar$^2$ is phenyl, naphthyl or pyridyl each optionally substituted by one to three R$^b$;

R$^1$ is —CH$_3$, —CH$_2$OH, —CH$_2$NH$_2$ or —CH$_2$NHCH$_3$;

R$^2$ is C$_{1-3}$ alkyl, C$_{2-6}$alkenyl, cyclopropyl, C$_{1-3}$ alkoxycarbonylmethyl, hydroxyC$_{2-4}$alkyl, C$_{1-3}$alkylaminocarbonylmethyl, C$_{1-3}$dialkylaminocarbonylmethyl, 4-methylpiperidin-1-ylcarbonylC$_{2-4}$alkyl, phenyl(CH$_2$)$_{0-1}$ alkylaminoC$_{4-5}$ alkyl or pyridyl(CH$_2$)$_{0-1}$alkylaminoC$_{4-5}$ alkyl R$^3$ is hydrogen;

R$^b$ is Br, Cl, F, CF$_3$, C$_{1-6}$ alkyl, C$_{1-6}$ alkoxy, —NHSO$_2$C$_{1-3}$ alkyl, —SO$_2$C$_{1-3}$alkyl, —SO$_2$(CH$_2$)$_{1-3}$OH, —SO$_2$(CH$_2$)$_{1-3}$CO$_2$C$_{1-3}$alkyl, —SO$_2$NH$_2$, —SO$_2$NHC$_{1-3}$alkyl, —SO$_2$N(diC$_{1-3}$alkyl), —SO$_2$NH(tetrahydropyran-4-yl) or —SO$_2$NH(CH$_2$)$_{2-3}$OH.

In a further embodiment, there is provided compounds as described in the embodiment immediately above and wherein:

Ar$^1$ is phenyl optionally substituted by one to three groups selected from methyl, Br, Cl, F and CH$_3$SO$_2$—;

X is a bond;

Ar$^2$ is phenyl or pyridyl each optionally substituted by one to three R$^b$;

R$^1$ is —CH$_3$;

R$^2$ is methyl, ethyl or n-propyl;

R$^3$ is hydrogen;

R$^b$ is Br, Cl, F, CF$_3$, —NHSO$_2$C$_{1-3}$alkyl, —SO$_2$C$_{1-3}$alkyl, —SO$_2$(CH$_2$)$_{1-3}$OH, —SO$_2$(CH$_2$)$_{1-3}$CO$_2$C$_{1-3}$alkyl, —SO$_2$NH$_2$, —SO$_2$NHC$_{1-3}$alkyl, —SO$_2$N(diC$_{1-3}$alkyl), —SO$_2$NH(tetrahydropyran-4-yl) or —SO$_2$NH(CH$_2$)$_{2-3}$OH.

The following are representative compounds of the invention which can be made by the general synthetic schemes, the examples, and known methods in the art.

TABLE 1

| STRUCTURE | Name | Observed mass ([M + H]) |
|---|---|---|
| 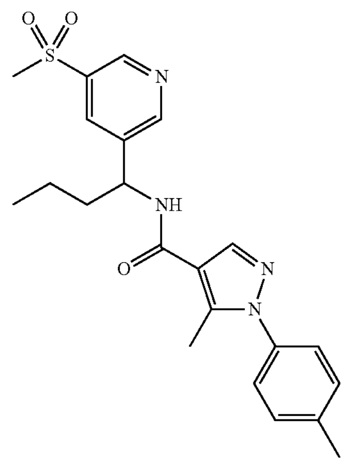 | 5-Methyl-1-p-tolyl-1H-pyrazole-4-carboxylic acid [1-(5-methanesulfonyl-pyridin-3-yl)-butyl]-amide | 427 |
| 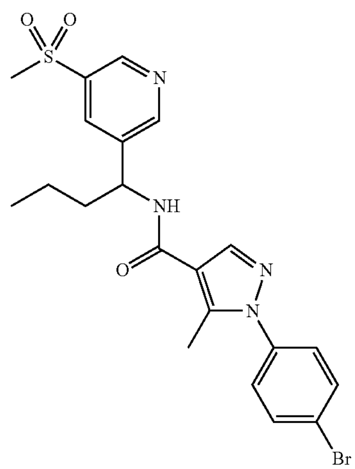 | 1-(4-Bromo-phenyl)-5-methyl-1H-pyrazole-4-carboxylic acid [1-(5-methanesulfonyl-pyridin-3-yl)-butyl]-amide | 491, 493 |
| 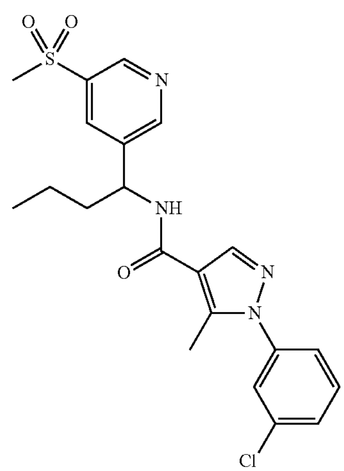 | 1-(3-Chloro-phenyl)-5-methyl-1H-pyrazole-4-carboxylic acid [1-(5-methanesulfonyl-pyridin-3-yl)-butyl]-amide | 447 |

TABLE 1-continued

| STRUCTURE | Name | Observed mass ([M + H]) |
|---|---|---|
| 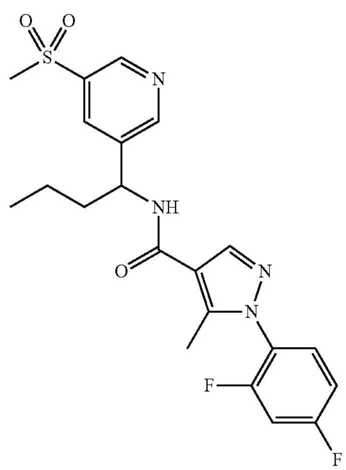 | 1-(2,4-Difluoro-phenyl)-5-methyl-1H-pyrazole-4-carboxylic acid [1-(5-methanesulfonyl-pyridin-3-yl)-butyl]-amide | 449 |
| 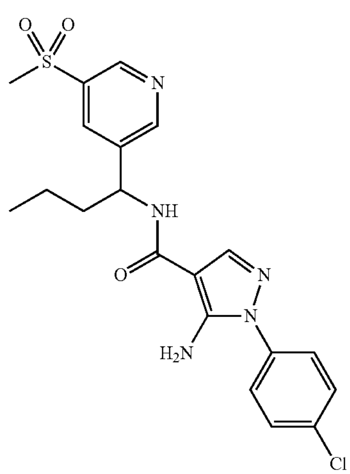 | 5-Amino-1-(4-chloro-phenyl)-1H-pyrazole-4-carboxylic acid [1-(5-methanesulfonyl-pyridin-3-yl)-butyl]-amide | 448 |
| 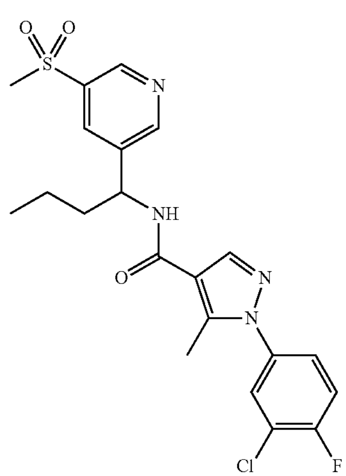 | 1-(3-Chloro-4-fluoro-phenyl)-5-methyl-1H-pyrazole-4-carboxylic acid [1-(5-methanesulfonyl-pyridin-3-yl)-butyl]-amide | 465 |

TABLE 1-continued
| STRUCTURE | Name | Observed mass ([M + H]) |
|---|---|---|
| 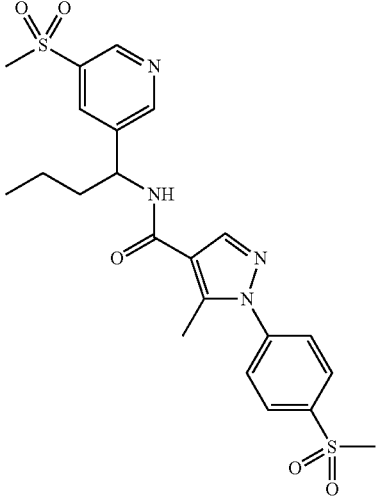 | 1-(4-Methanesulfonyl-phenyl)-5-methyl-1H-pyrazole-4-carboxylic acid [1-(5-methanesulfonyl-pyridin-3-yl)-butyl]-amide | 491 |
| 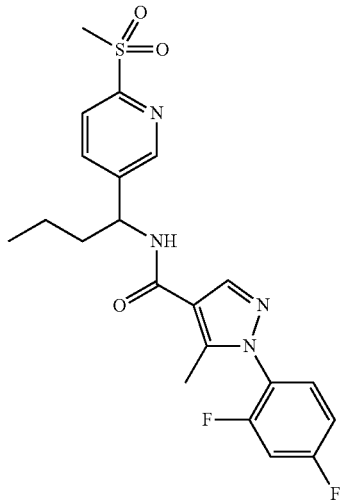 | 1-(2,4-Difluoro-phenyl)-5-methyl-1H-pyrazole-4-carboxylic acid [1-(6-methanesulfonyl-pyridin-3-yl)-butyl]-amide | 449 |
| 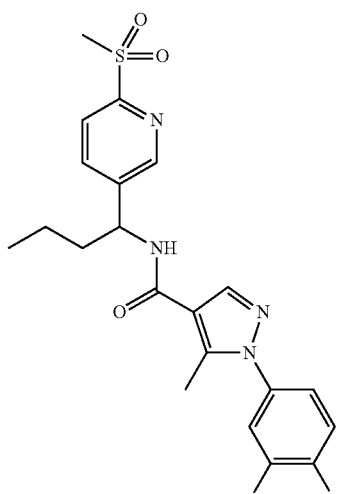 | 1-(3-Chloro-4-fluoro-phenyl)-5-methyl-1H-pyrazole-4-carboxylic acid [1-(6-methanesulfonyl-pyridin-3-yl)-butyl]-amide | 465 |

TABLE 1-continued

| STRUCTURE | Name | Observed mass ([M + H]) |
|---|---|---|
| 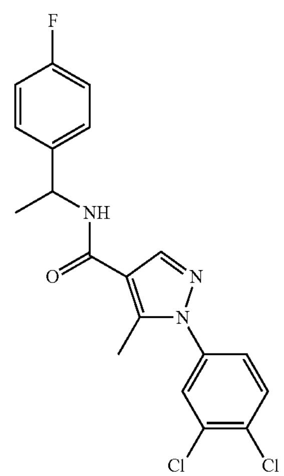 | 1-(3,4-Dichloro-phenyl)-5-methyl-1H-pyrazole-4-carboxylic acid [1-(4-fluoro-phenyl)-ethyl]-amide | 392 |
| 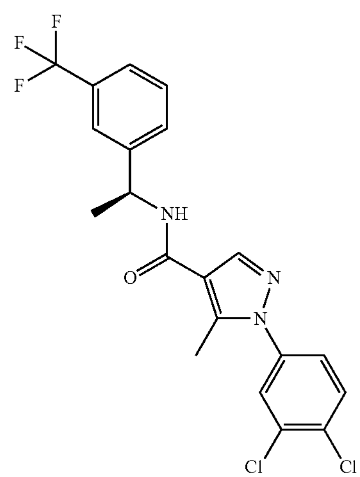 | 1-(3,4-Dichloro-phenyl)-5-methyl-1H-pyrazole-4-carboxylic acid [(S)-1-(3-trifluoromethyl-phenyl)-ethyl]-amide | 442 |
| 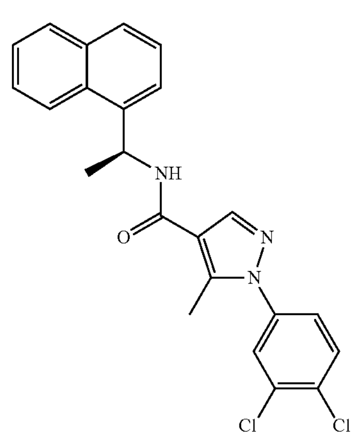 | 1-(3,4-Dichloro-phenyl)-5-methyl-1H-pyrazole-4-carboxylic acid ((S)-1-naphthalen-1-yl-ethyl)-amide | 424 |

TABLE 1-continued

| STRUCTURE | Name | Observed mass ([M + H]) |
| --- | --- | --- |
| 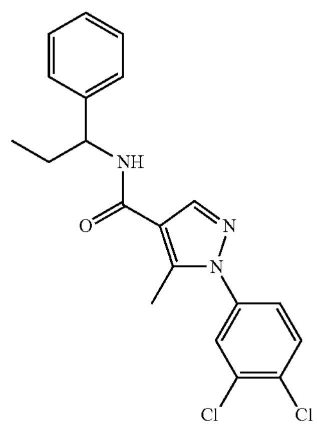 | 1-(3,4-Dichloro-phenyl)-5-methyl-1H-pyrazole-4-carboxylic acid (1-phenyl-propyl)-amide | 388 |
| 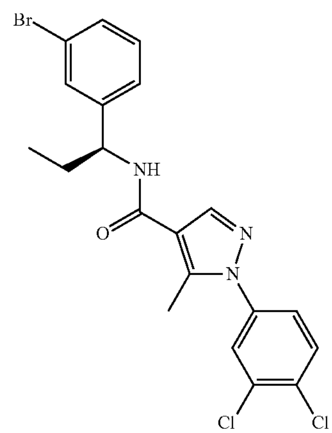 | 1-(3,4-Dichloro-phenyl)-5-methyl-1H-pyrazole-4-carboxylic acid [(S)-1-(3-bromo-phenyl)-propyl]-amide | 468, 470 |
| 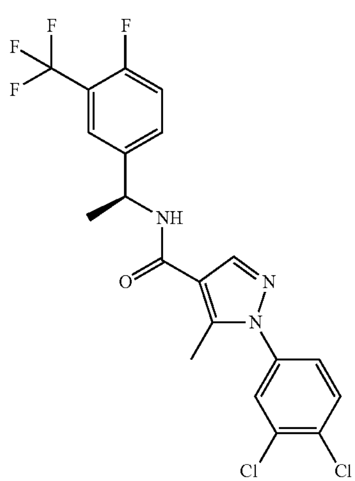 | 1-(3,4-Dichloro-phenyl)-5-methyl-1H-pyrazole-4-carboxylic acid [(S)-1-(4-fluoro-3-trifluoromethyl-phenyl)-ethyl]-amide | 460 |

TABLE 1-continued
| STRUCTURE | Name | Observed mass ([M + H]) |
|---|---|---|
| 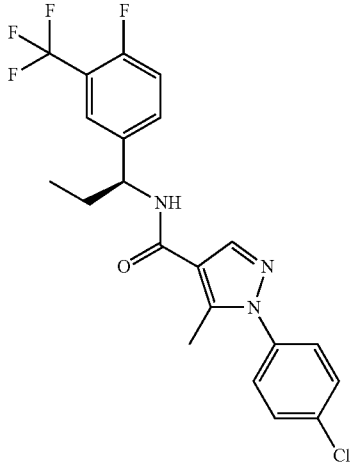 | 1-(4-Chloro-phenyl)-5-methyl-1H-pyrazole-4-carboxylic acid [(S)-1-(4-fluoro-3-trifluoromethyl-phenyl)-propyl]-amide | 440 |
| 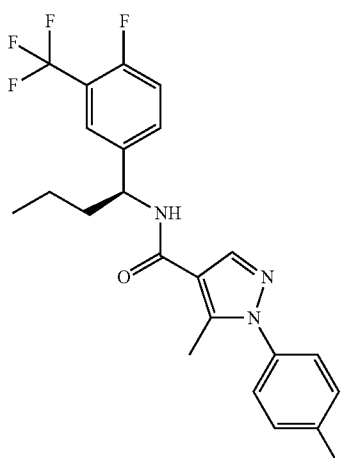 | 1-(4-Chloro-phenyl)-5-methyl-1H-pyrazole-4-carboxylic acid [(S)-1-(4-fluoro-3-trifluoromethyl-phenyl)-butyl]-amide | 453 |
| 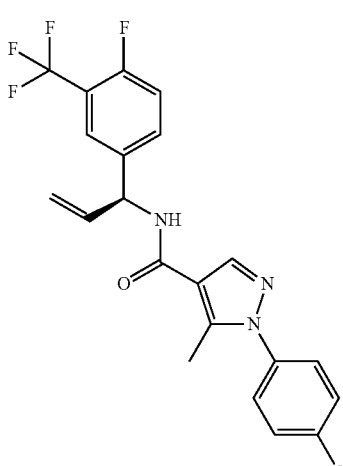 | 1-(4-Chloro-phenyl)-5-methyl-1H-pyrazole-4-carboxylic acid [(S)-1-(4-fluoro-3-trifluoromethyl-phenyl)-allyl]-amide | 437 |

TABLE 1-continued

| STRUCTURE | Name | Observed mass ([M + H]) |
|---|---|---|
| 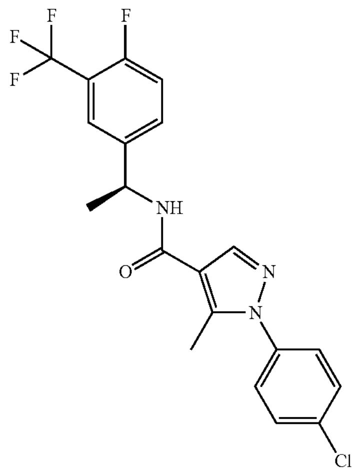 | 1-(4-Chloro-phenyl)-5-methyl-1H-pyrazole-4-carboxylic acid [(S)-1-(4-fluoro-3-trifluoromethyl-phenyl)-ethyl]-amide | 426 |
| 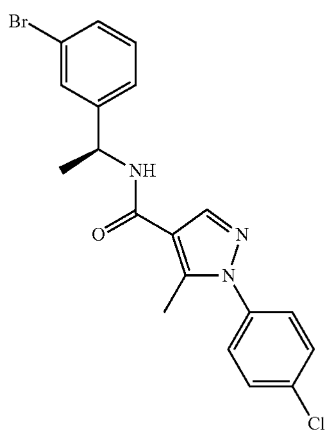 | 1-(4-Chloro-phenyl)-5-methyl-1H-pyrazole-4-carboxylic acid [(S)-1-(3-bromo-phenyl)-ethyl]-amide | 418, 420 |
| 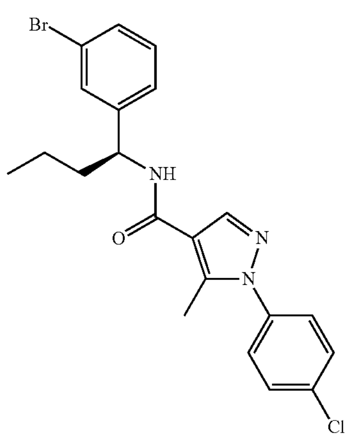 | 1-(4-Chloro-phenyl)-5-methyl-1H-pyrazole-4-carboxylic acid [(S)-1-(3-bromo-phenyl)-butyl]-amide | 446, 448 |

TABLE 1-continued
| STRUCTURE | Name | Observed mass ([M + H]) |
|---|---|---|
| 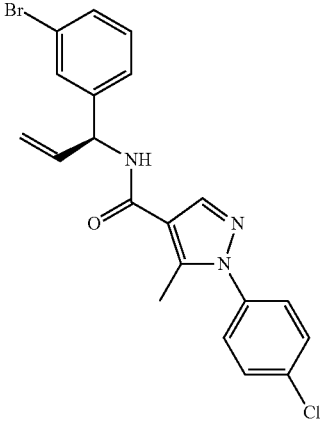 | 1-(4-Chloro-phenyl)-5-methyl-1H-pyrazole-4-carboxylic acid [(S)-1-(3-bromo-phenyl)-allyl]-amide | 430, 432 |
| 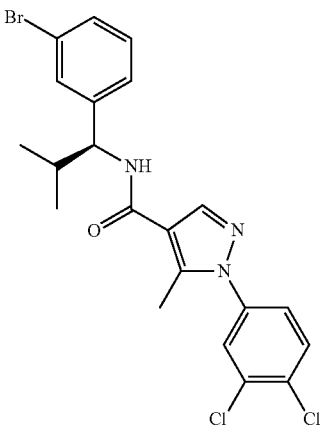 | 1-(3,4-Dichloro-phenyl)-5-methyl-1H-pyrazole-4-carboxylic acid [(S)-1-(3-bromo-phenyl)-2-methyl-propyl]-amide | 481, 483 |
| 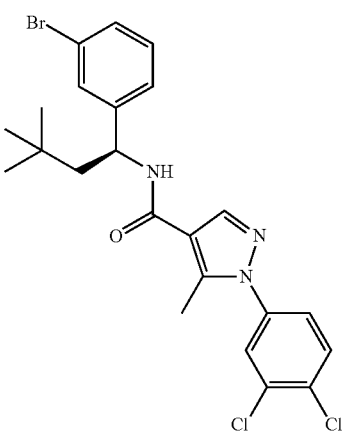 | 1-(3,4-Dichloro-phenyl)-5-methyl-1H-pyrazole-4-carboxylic acid [(S)-1-(3-bromo-phenyl)-3,3-dimethyl-butyl]-amide | 509, 511 |

TABLE 1-continued

| STRUCTURE | Name | Observed mass ([M + H]) |
|---|---|---|
| 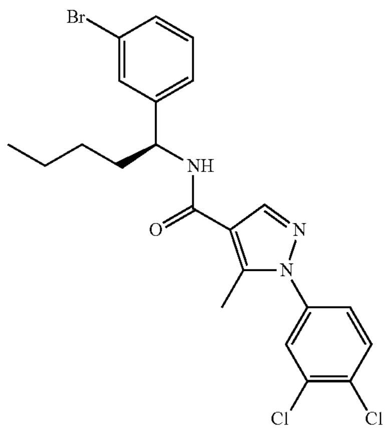 | 1-(3,4-Dichloro-phenyl)-5-methyl-1H-pyrazole-4-carboxylic acid [(S)-1-(3-bromo-phenyl)-pentyl]-amide | 495, 497 |
| 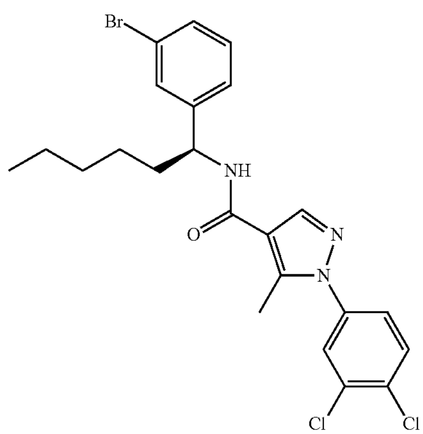 | 1-(3,4-Dichloro-phenyl)-5-methyl-1H-pyrazole-4-carboxylic acid [(S)-1-(3-bromo-phenyl)-hexyl]-amide | 509, 511 |
| 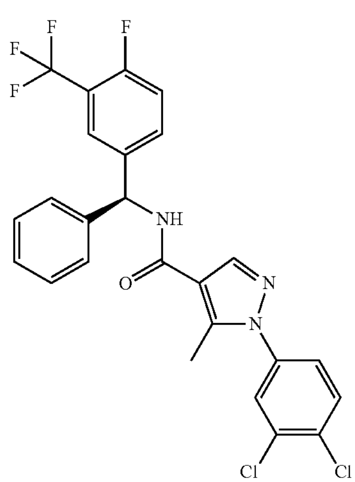 | 1-(3,4-Dichloro-phenyl)-5-methyl-1H-pyrazole-4-carboxylic acid [(S)-(4-fluoro-3-trifluoromethyl-phenyl)-phenyl-methyl]-amide | 522 |

TABLE 1-continued
| STRUCTURE | Name | Observed mass ([M + H]) |
|---|---|---|
| 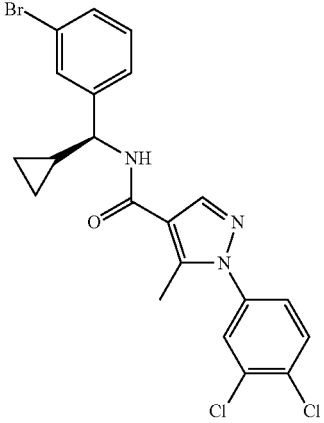 | 1-(3,4-Dichloro-phenyl)-5-methyl-1H-pyrazole-4-carboxylic acid [(S)-(3-bromo-phenyl)-cyclopropyl-methyl]-amide | 480, 482 |
| 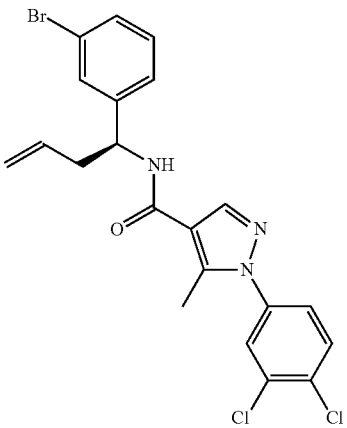 | 1-(3,4-Dichloro-phenyl)-5-methyl-1H-pyrazole-4-carboxylic acid [(S)-1-(3-bromo-phenyl)-but-3-enyl]-amide | 480, 482 |
| 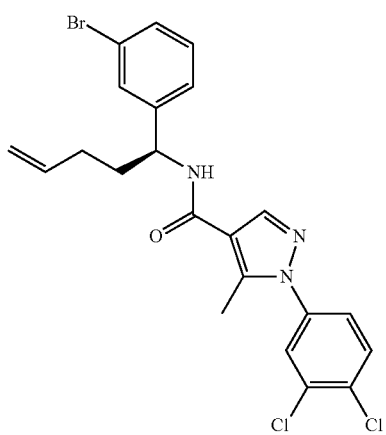 | 1-(3,4-Dichloro-phenyl)-5-methyl-1H-pyrazole-4-carboxylic acid [(S)-1-(3-bromo-phenyl)-pent-4-enyl]-amide | 494, 496 |

TABLE 1-continued

| STRUCTURE | Name | Observed mass ([M + H]) |
|---|---|---|
| 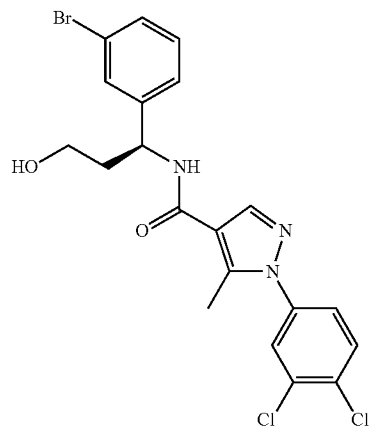 | 1-(3,4-Dichloro-phenyl)-5-methyl-1H-pyrazole-4-carboxylic acid [(S)-1-(3-bromo-phenyl)-3-hydroxy-propyl]-amide | 484, 486 |
| 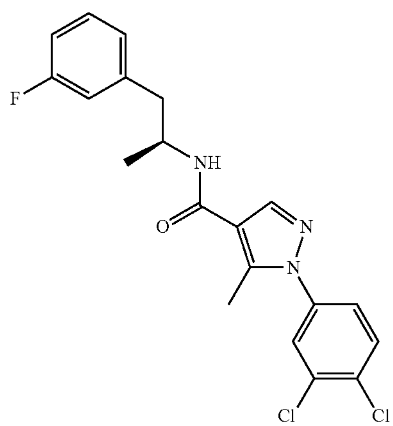 | 1-(3,4-Dichloro-phenyl)-5-methyl-1H-pyrazole-4-carboxylic acid [(S)-2-(3-fluoro-phenyl)-1-methyl-ethyl]-amide | 406 |
| 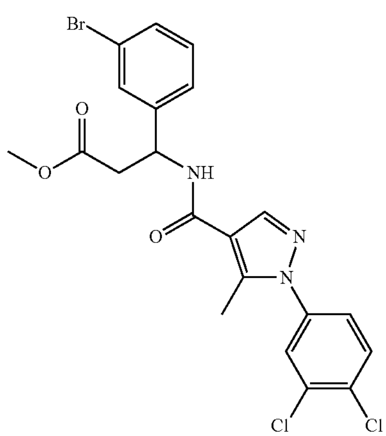 | 3-(3-Bromo-phenyl)-3-{[1-(3,4-dichloro-phenyl)-5-methyl-1H-pyrazole-4-carbonyl]-amino}-propionic acid methyl ester | 512, 514 |

TABLE 1-continued

| STRUCTURE | Name | Observed mass ([M + H]) |
|---|---|---|
| 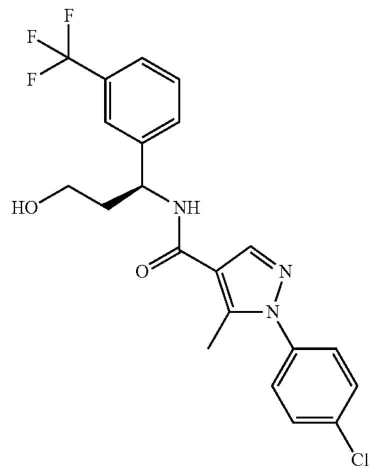 | 1-(4-Chloro-phenyl)-5-methyl-1H-pyrazole-4-carboxylic acid [(S)-3-hydroxy-1-(3-trifluoromethyl-phenyl)-propyl]-amide | 438 |
| 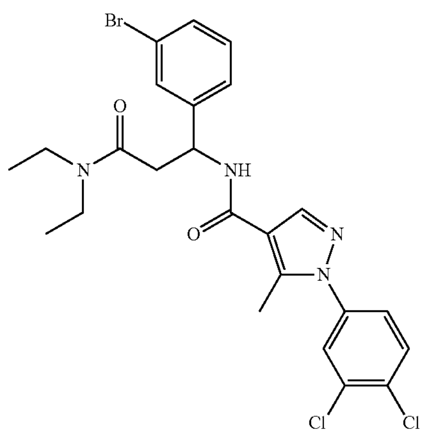 | 1-(3,4-Dichloro-phenyl)-5-methyl-1H-pyrazole-4-carboxylic acid [1-(3-bromo-phenyl)-2-diethylcarbamoyl-ethyl]-amide | 553, 555 |
| 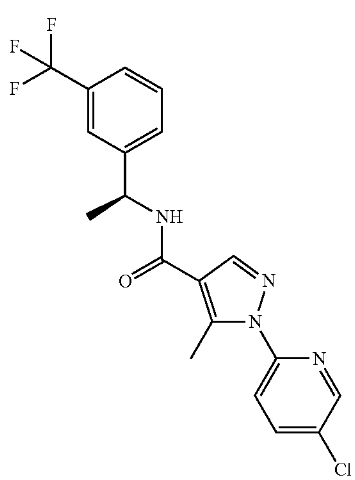 | 1-(5-Chloro-pyridin-2-yl)-5-methyl-1H-pyrazole-4-carboxylic acid [(S)-1-(3-trifluoromethyl-phenyl)-ethyl]-amide | 409 |

TABLE 1-continued

| STRUCTURE | Name | Observed mass ([M + H]) |
|---|---|---|
| 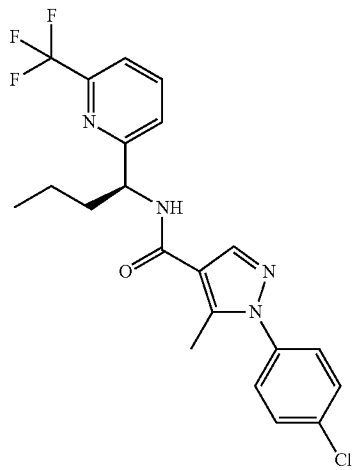 | 1-(4-Chloro-phenyl)-5-methyl-1H-pyrazole-4-carboxylic acid [(S)-1-(6-trifluoromethyl-pyridin-2-yl)-butyl]-amide | 437 |
| 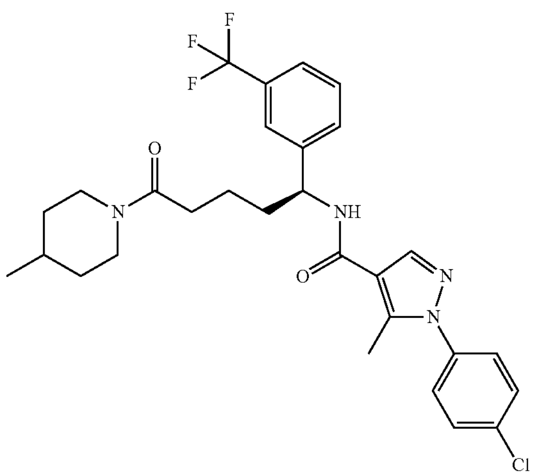 | 1-(4-Chloro-phenyl)-5-methyl-1H-pyrazole-4-carboxylic acid [(S)-5-(4-methyl-piperidin-1-yl)-5-oxo-1-(3-trifluoromethyl-phenyl)-pentyl]-amide | 561 |
| 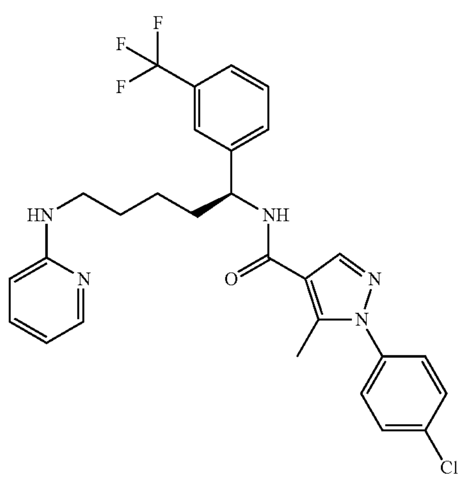 | 1-(4-Chloro-phenyl)-5-methyl-1H-pyrazole-4-carboxylic acid [(S)-5-(pyridin-2-ylamino)-1-(3-trifluoromethyl-phenyl)-pentyl]-amide | 542 |

TABLE 1-continued
| STRUCTURE | Name | Observed mass ([M + H]) |
|---|---|---|
| 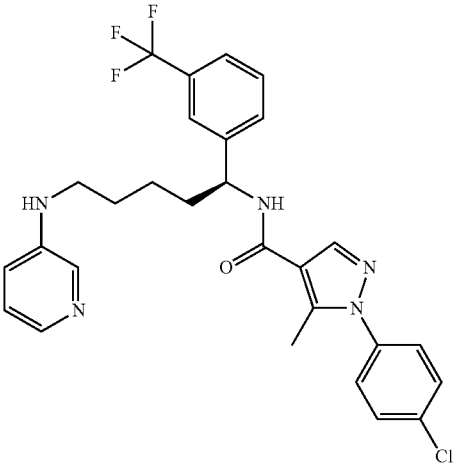 | 1-(4-Chloro-phenyl)-5-methyl-1H-pyrazole-4-carboxylic acid [(S)-5-(pyridin-3-ylamino)-1-(3-trifluoromethyl-phenyl)-pentyl]-amide | 542 |
| 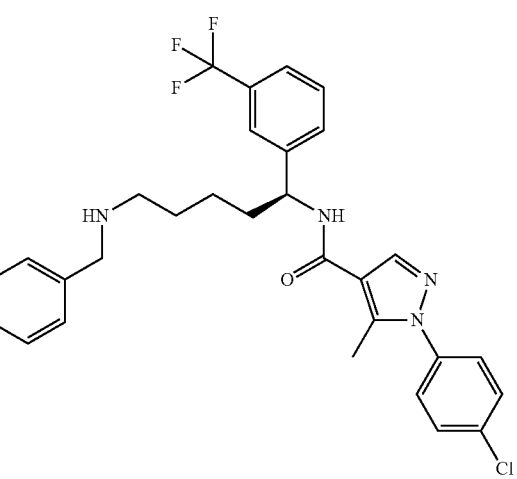 | 1-(4-Chloro-phenyl)-5-methyl-1H-pyrazole-4-carboxylic acid [(S)-5-benzylamino-1-(3-trifluoromethyl-phenyl)-pentyl]-amide | 555 |
| 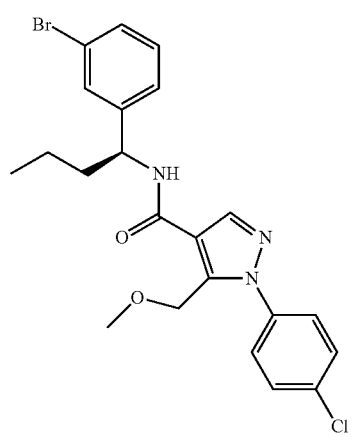 | 1-(4-Chloro-phenyl)-5-methoxymethyl-1H-pyrazole-4-carboxylic acid [(S)-1-(3-bromo-phenyl)-butyl]-amide | 476, 478 |

TABLE 1-continued

| STRUCTURE | Name | Observed mass ([M + H]) |
|---|---|---|
| 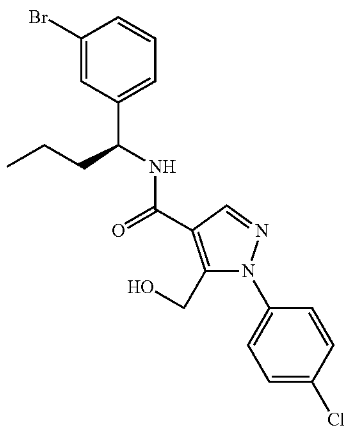 | 1-(4-Chloro-phenyl)-5-hydroxymethyl-1H-pyrazole-4-carboxylic acid [(S)-1-(3-bromo-phenyl)-butyl]-amide | 462, 464 |
| 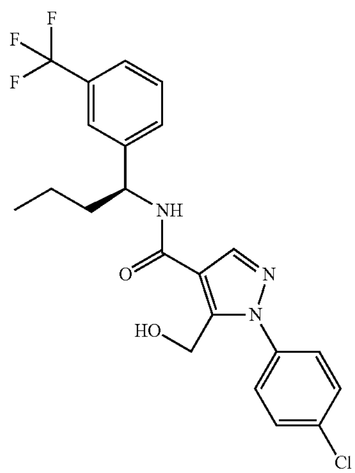 | 1-(4-Chloro-phenyl)-5-hydroxymethyl-1H-pyrazole-4-carboxylic acid [(S)-1-(3-trifluoromethyl-phenyl)-butyl]-amide | 453 |
| 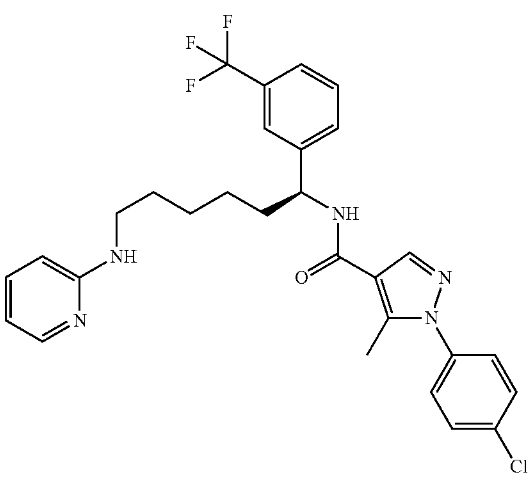 | 1-(4-Chloro-phenyl)-5-methyl-1H-pyrazole-4-carboxylic acid [(S)-6-(pyridin-2-ylamino)-1-(3-trifluoromethyl-phenyl)-hexyl]-amide | 556 |

TABLE 1-continued

| STRUCTURE | Name | Observed mass ([M + H]) |
|---|---|---|
| 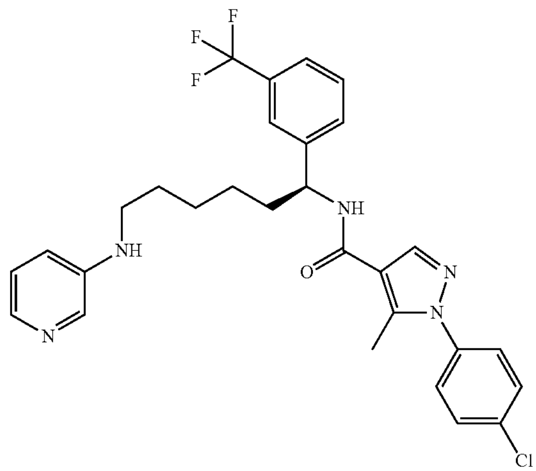 | 1-(4-Chloro-phenyl)-5-methyl-1H-pyrazole-4-carboxylic acid [(S)-6-(pyridin-3-ylamino)-1-(3-trifluoromethyl-phenyl)-hexyl]-amide | 556 |
| 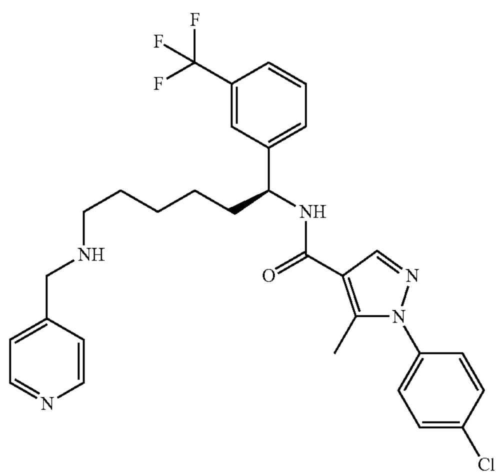 | 1-(4-Chloro-phenyl)-5-methyl-1H-pyrazole-4-carboxylic acid [(S)-6-[(pyridin-4-ylmethyl)-amino]-1-(3-trifluoromethyl-phenyl)-hexyl]-amide | 570 |
| 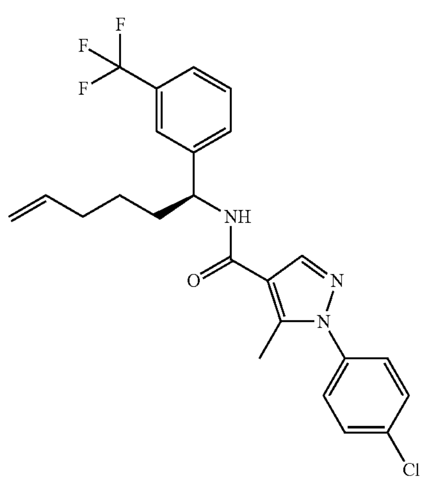 | 1-(4-Chloro-phenyl)-5-methyl-1H-pyrazole-4-carboxylic acid [(S)-1-(3-trifluoromethyl-phenyl)-hex-5-enyl]-amide | 462 |

TABLE 1-continued

| STRUCTURE | Name | Observed mass ([M + H]) |
|---|---|---|
| 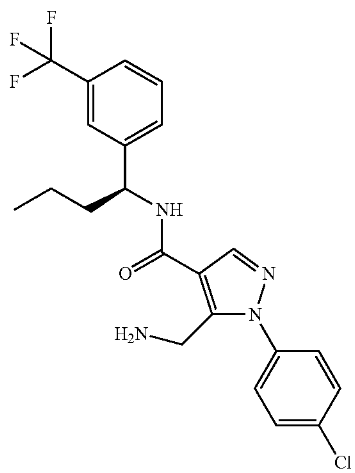 | 5-Aminomethyl-1-(4-chloro-phenyl)-1H-pyrazole-4-carboxylic acid [(S)-1-(3-trifluoromethyl-phenyl)-butyl]-amide | 452 |
| 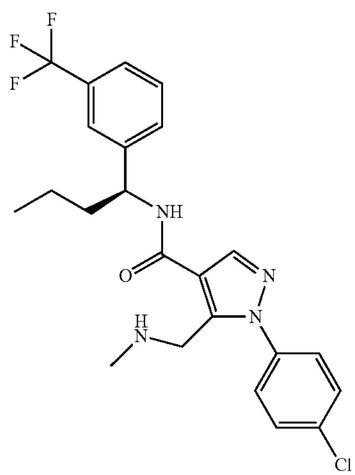 | 1-(4-Chloro-phenyl)-5-methylaminomethyl-1H-pyrazole-4-carboxylic acid [(S)-1-(3-trifluoromethyl-phenyl)-butyl]-amide | 465 |
| 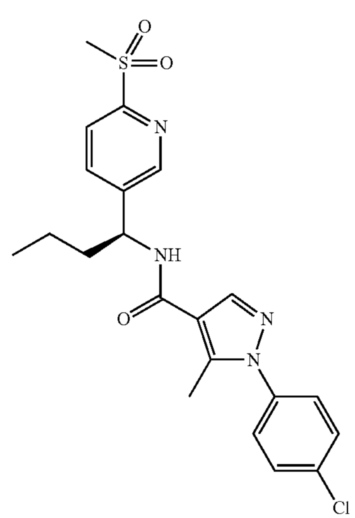 | 1-(4-Chloro-phenyl)-5-methyl-1H-pyrazole-4-carboxylic acid [1-(6-methanesulfonyl-pyridin-3-yl)-butyl]-amide | 447 |

TABLE 1-continued
| STRUCTURE | Name | Observed mass ([M + H]) |
|---|---|---|
| 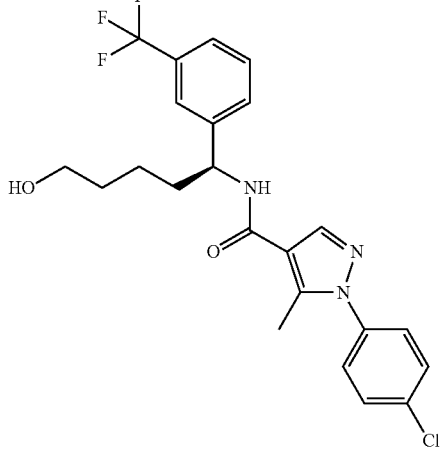 | 1-(4-Chloro-phenyl)-5-methyl-1H-pyrazole-4-carboxylic acid [(S)-5-hydroxy-1-(3-trifluoromethyl-phenyl)-pentyl]-amide | 466 |
| 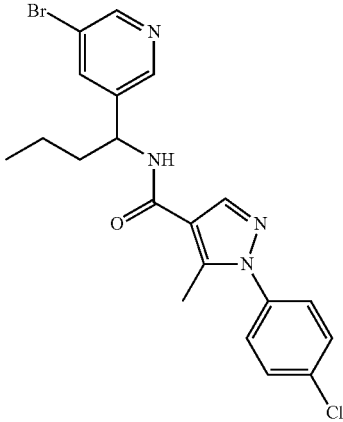 | 1-(4-Chloro-phenyl)-5-methyl-1H-pyrazole-4-carboxylic acid [1-(5-bromo-pyridin-3-yl)-butyl]-amide | 447, 449 |
| 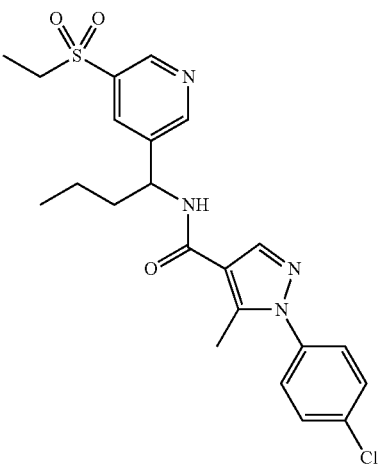 | 1-(4-Chloro-phenyl)-5-methyl-1H-pyrazole-4-carboxylic acid [1-(5-ethanesulfonyl-pyridin-3-yl)-butyl]-amide | 462 |

TABLE 1-continued

| STRUCTURE | Name | Observed mass ([M + H]) |
|---|---|---|
| 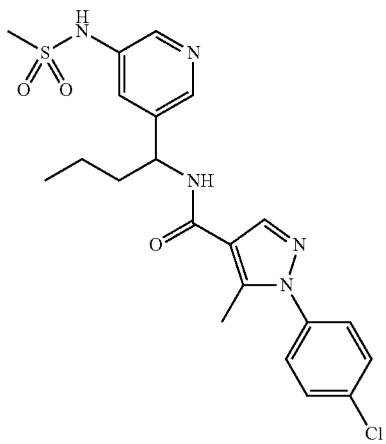 | 1-(4-Chloro-phenyl)-5-methyl-1H-pyrazole-4-carboxylic acid [1-(5-methanesulfonylamino-pyridin-3-yl)-butyl]-amide | 462 |
| 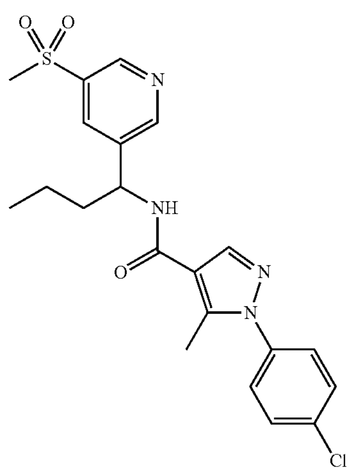 | 1-(4-Chloro-phenyl)-5-methyl-1H-pyrazole-4-carboxylic acid [1-(5-methanesulfonyl-pyridin-3-yl)-butyl]-amide | 447 |
| 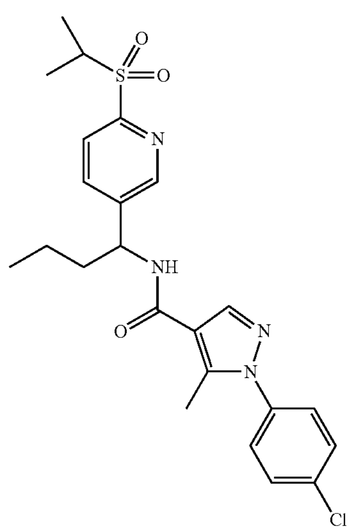 | 1-(4-Chloro-phenyl)-5-methyl-1H-pyrazole-4-carboxylic acid {1-[6-(propane-2-sulfonyl)-pyridin-3-yl]-butyl}-amide | 475 |

TABLE 1-continued

| STRUCTURE | Name | Observed mass ([M + H]) |
|---|---|---|
| 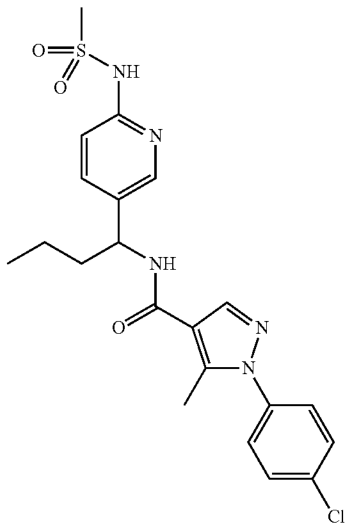 | 1-(4-Chloro-phenyl)-5-methyl-1H-pyrazole-4-carboxylic acid [1-(6-methanesulfonylamino-pyridin-3-yl)-butyl]-amide | 463 |
| 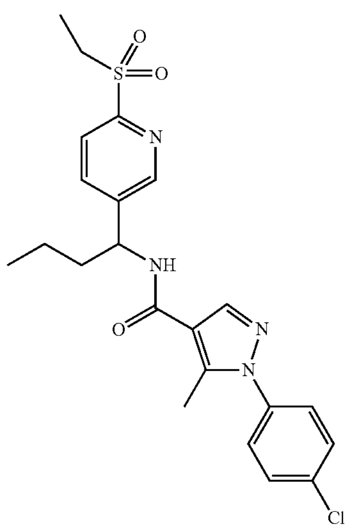 | 1-(4-Chloro-phenyl)-5-methyl-1H-pyrazole-4-carboxylic acid [1-(6-ethanesulfonyl-pyridin-3-yl)-butyl]-amide | 461 |
| 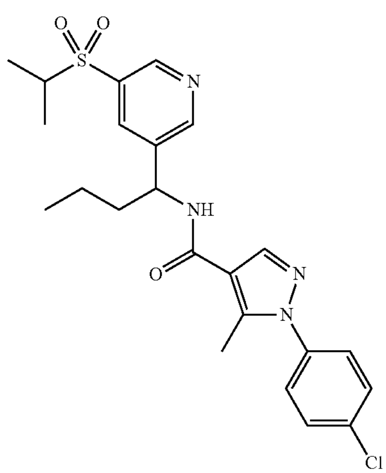 | 1-(4-Chloro-phenyl)-5-methyl-1H-pyrazole-4-carboxylic acid {1-[5-(propane-2-sulfonyl)-pyridin-3-yl]-butyl}-amide | 475 |

TABLE 1-continued

| STRUCTURE | Name | Observed mass ([M + H]) |
|---|---|---|
| 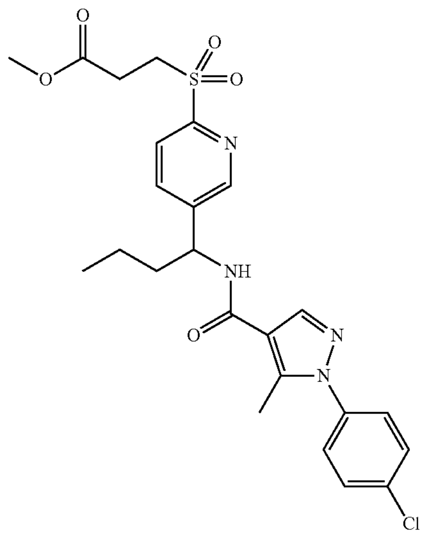 | 3-[5-(1-{[1-(4-Chloro-phenyl)-5-methyl-1H-pyrazole-4-carbonyl]-amino}-butyl)-pyridine-2-sulfonyl]-propionic acid methyl ester | 520 |
| 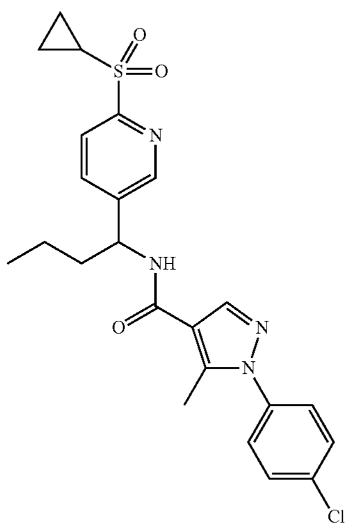 | 1-(4-Chloro-phenyl)-5-methyl-1H-pyrazole-4-carboxylic acid [1-(6-cyclopropanesulfonyl-pyridin-3-yl)-butyl]-amide | 474 |
| | 3-[5-(1-{[1-(4-Chloro-phenyl)-5-methyl-1H-pyrazole-4-carbonyl]-amino}-butyl)-pyridine-3-sulfonyl]-proponic acid methyl ester | 520 |

TABLE 1-continued

| STRUCTURE | Name | Observed mass ([M + H]) |
|---|---|---|
| 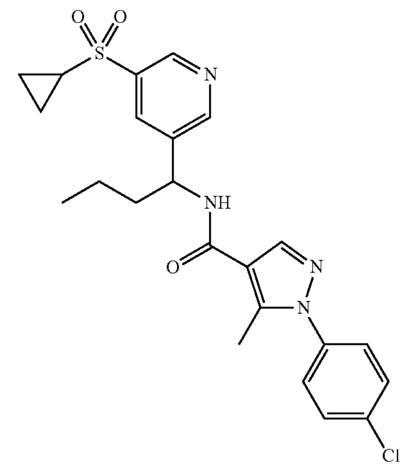 | 1-(4-Chloro-phenyl)-5-methyl-1H-pyrazole-4-carboxylic acid [1-(5-cyclopropanesulfonyl-pyridin-3-yl)-butyl]-amide | 474 |
| 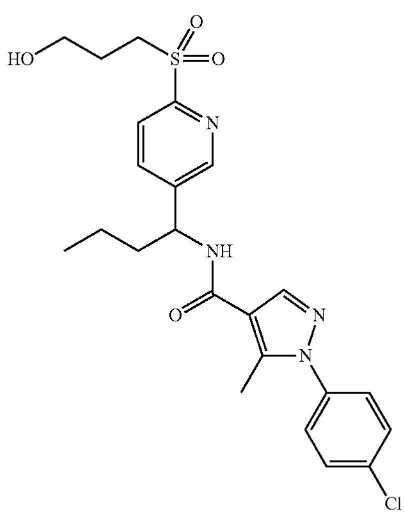 | 1-(4-Chloro-phenyl)-5-methyl-1H-pyrazole-4-carboxylic acid {1-[6-(3-hydroxy-propane-1-sulfonyl)-pyridin-3-yl]-butyl}-amide | 492 |
| 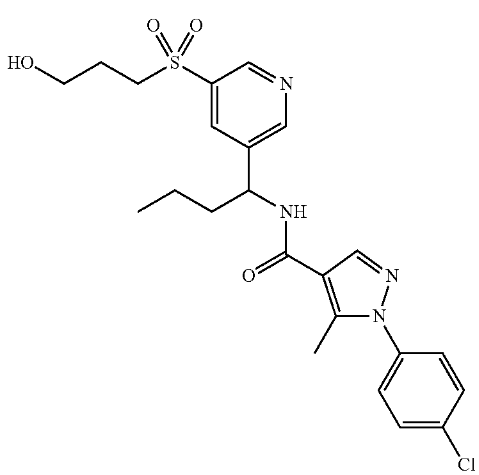 | 1-(4-Chloro-phenyl)-5-methyl-1H-pyrazole-4-carboxylic acid {1-[5-(3-hydroxy-propane-1-sulfonyl)-pyridin-3-yl]-butyl}-amide | 492 |

TABLE 1-continued

| STRUCTURE | Name | Observed mass ([M + H]) |
|---|---|---|
| 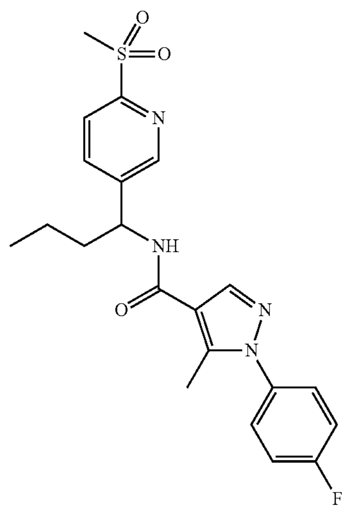 | 1-(4-Fluoro-phenyl)-5-methyl-1H-pyrazole-4-carboxylic acid [1-(6-methanesulfonyl-pyridin-3-yl)-butyl]-amide | 432 |
| 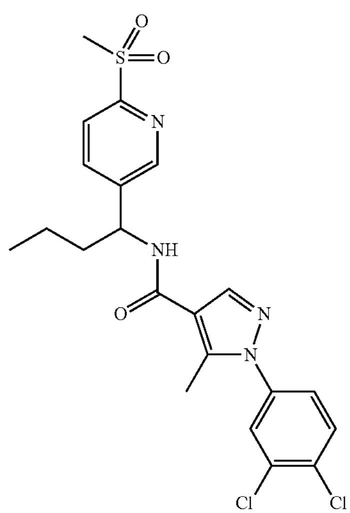 | 1-(3,4-Dichloro-phenyl)-5-methyl-1H-pyrazole-4-carboxylic acid [1-(6-methanesulfonyl-pyridin-3-yl)-butyl]-amide | 482 |
| 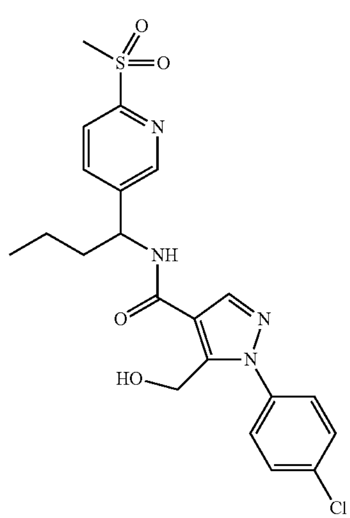 | 1-(4-Chloro-phenyl)-5-hydroxymethyl-1H-pyrazole-4-carboxylic acid [1-(6-methanesulfonyl-pyridin-3-yl)-butyl]-amide | 464 |

TABLE 1-continued

| STRUCTURE | Name | Observed mass ([M + H]) |
|---|---|---|
| 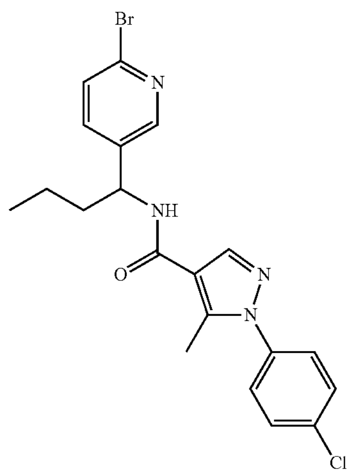 | 1-(4-Chloro-phenyl)-5-methyl-1H-pyrazole-4-carboxylic acid [1-(6-bromo-pyridin-3-yl)-butyl]-amide | 448, 450 |
| 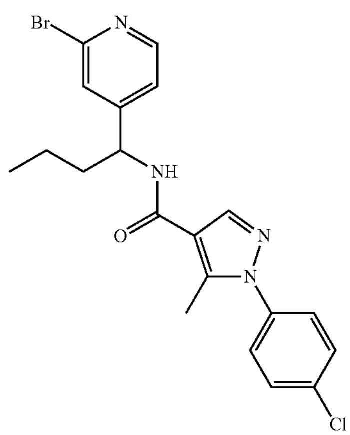 | 1-(4-Chloro-phenyl)-5-methyl-1H-pyrazole-4-carboxylic acid [1-(2-bromo-pyridin-4-yl)-butyl]-amide | 447, 449 |
| 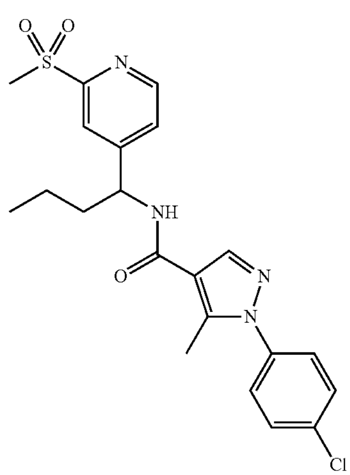 | 1-(4-Chloro-phenyl)-5-methyl-1H-pyrazole-4-carboxylic acid [1-(2-methanesulfonyl-pyridin-4-yl)-butyl]-amide | 447 |

TABLE 1-continued

| STRUCTURE | Name | Observed mass ([M + H]) |
|---|---|---|
| 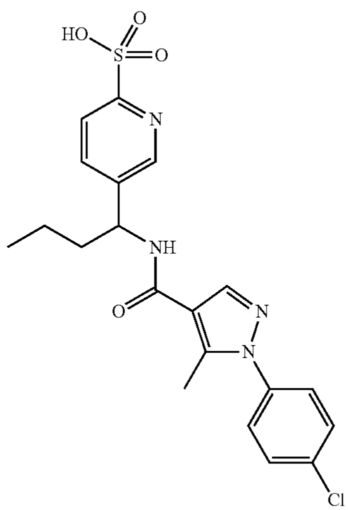 | 5-(1-{[1-(4-Chloro-phenyl)-5-methyl-1H-pyrazole-4-carbonyl]-amino}-butyl)-pyridine-2-sulfonic acid | 450 |
| 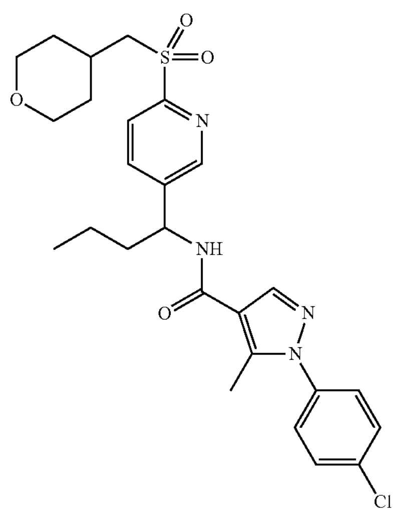 | 1-(4-Chloro-phenyl)-5-methyl-1H-pyrazole-4-carboxylic acid {1-[6-(tetrahydro-pyran-4-ylsulfamoyl)-pyridin-3-yl]-butyl}-amide | 533 |
| 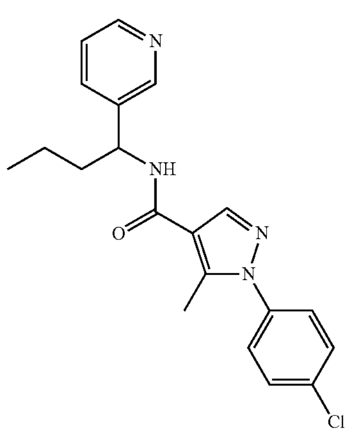 | 1-(4-Chloro-phenyl)-5-methyl-1H-pyrazole-4-carboxylic acid (1-pyridin-3-yl-butyl)-amide | 369 |

TABLE 1-continued

| STRUCTURE | Name | Observed mass ([M + H]) |
|---|---|---|
| 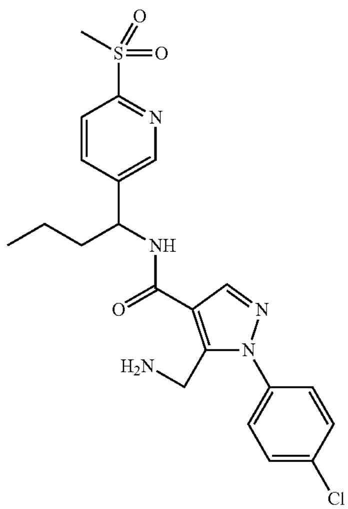 | 5-Aminomethyl-1-(4-chloro-phenyl)-1H-pyrazole-4-carboxylic acid [1-(6-methanesulfonyl-pyridin-3-yl)-butyl]-amide | 464 |
| 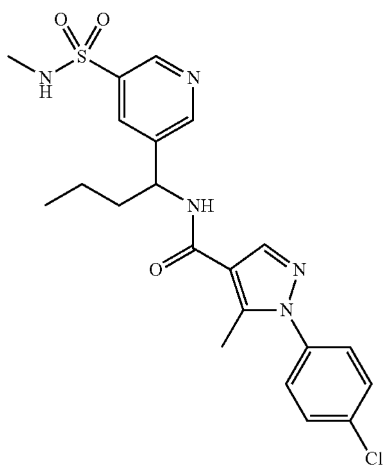 | 1-(4-Chloro-phenyl)-5-methyl-1H-pyrazole-4-carboxylic acid [1-(5-methylsulfamoyl-pyridin-3-yl)-butyl]-amide | 463 |
| 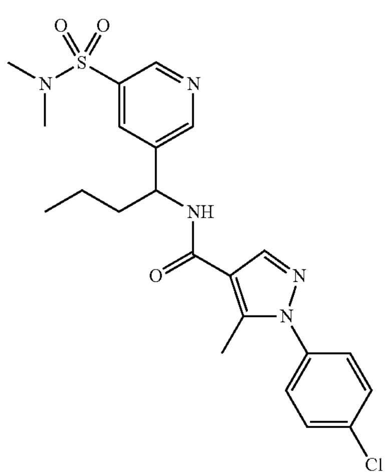 | 1-(4-Chloro-phenyl)-5-methyl-1H-pyrazole-4-carboxylic acid [1-(5-dimethylsulfamoyl-pyridin-3-yl)-butyl]-amide | 477 |

TABLE 1-continued

| STRUCTURE | Name | Observed mass ([M + H]) |
|---|---|---|
| 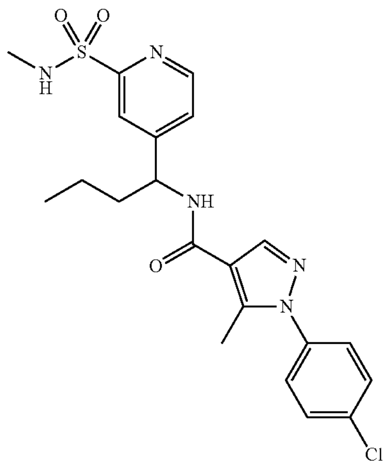 | 1-(4-Chloro-phenyl)-5-methyl-1H-pyrazole-4-carboxylic acid [1-(2-methylsulfamoyl-pyridin-4-yl)-butyl]-amide | 462 |
| 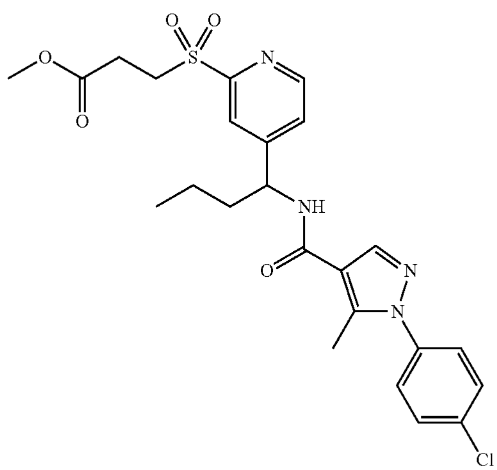 | 3-[4-(1-{[1-(4-Chloro-phenyl)-5-methyl-1H-pyrazole-4-carbonyl]-amino}-butyl)-pyridine-2-sulfonyl]-propionic acid methyl ester | 519 |
| 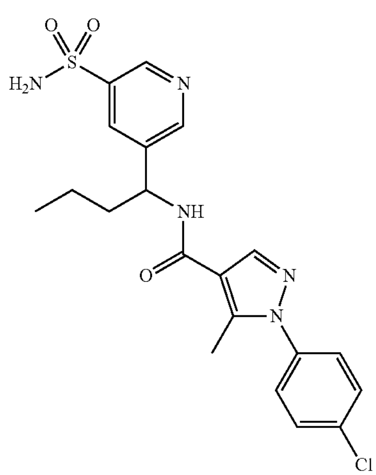 | 1-(4-Chloro-phenyl)-5-methyl-1H-pyrazole-4-carboxylic acid [1-(5-sulfamoyl-pyridin-3-yl)-butyl]-amide | 448 |

TABLE 1-continued

| STRUCTURE | Name | Observed mass ([M + H]) |
|---|---|---|
| 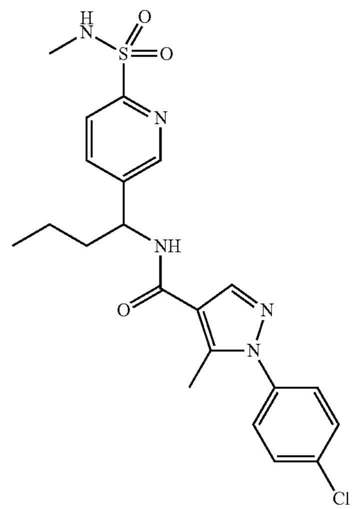 | 1-(4-Chloro-phenyl)-5-methyl-1H-pyrazole-4-carboxylic acid [1-(6-methylsufamoyl-pyridin-3-yl)-butyl]-amide | 463 |
| 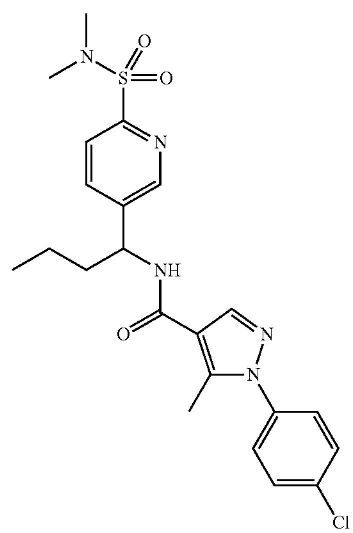 | 1-(4-Chloro-phenyl)-5-methyl-1H-pyrazole-4-carboxylic acid [1-(6-dimethylsulfamoyl-pyridin-3-yl)-butyl]-amide | 477 |
| 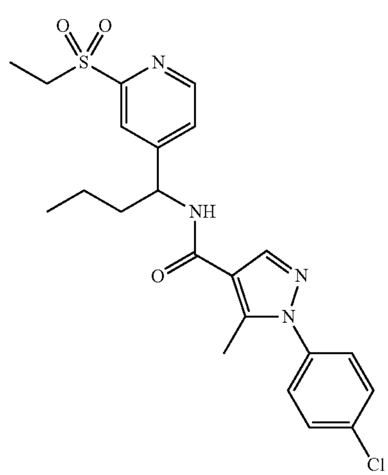 | 1-(4-Chloro-phenyl)-5-methyl-1H-pyrazole-4-carboxylic acid [1-(2-ethanesulfonyl-pyridin-4-yl)-butyl]-amide | 461 |

TABLE 1-continued

| STRUCTURE | Name | Observed mass ([M + H]) |
|---|---|---|
| 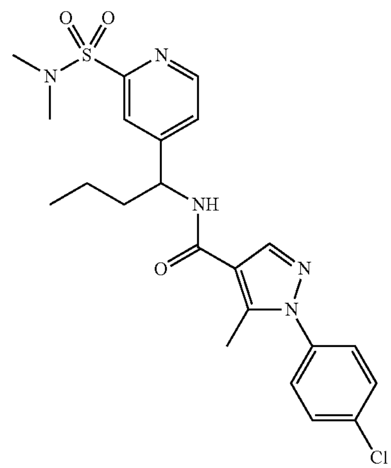 | 1-(4-Chloro-phenyl)-5-methyl-1H-pyrazole-4-carboxylic acid [1-(2-dimethylsulfamoyl-pyridin-4-yl)-butyl]-amide | 476 |
| 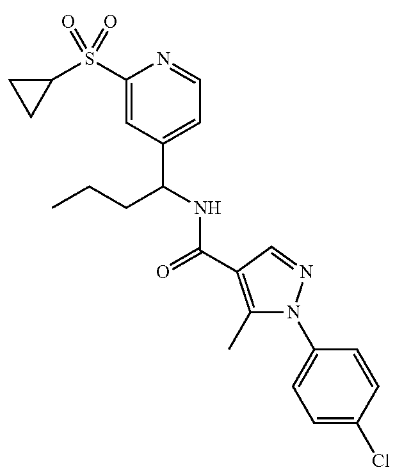 | 1-(4-Chloro-phenyl)-5-methyl-1H-pyrazole-4-carboxylic acid [1-(2-cyclopropanesulfonyl-pyridin-4-yl)-butyl]-amide | 473 |
| 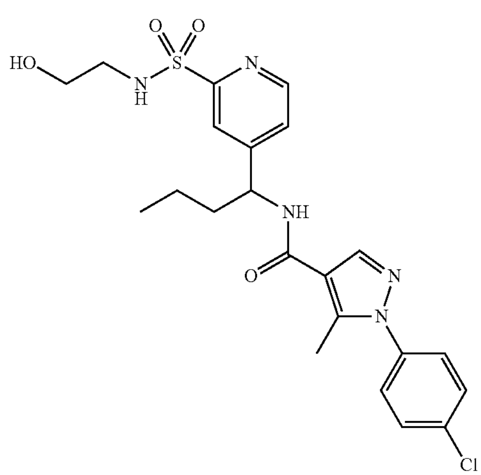 | 1-(4-Chloro-phenyl)-5-methyl-1H-pyrazole-4-carboxylic acid {1-[2-(2-hydroxy-ethylsulfamoyl)-pyridin-4-yl]-butyl}-amide | 492 |

TABLE 1-continued

| STRUCTURE | Name | Observed mass ([M + H]) |
|---|---|---|
| 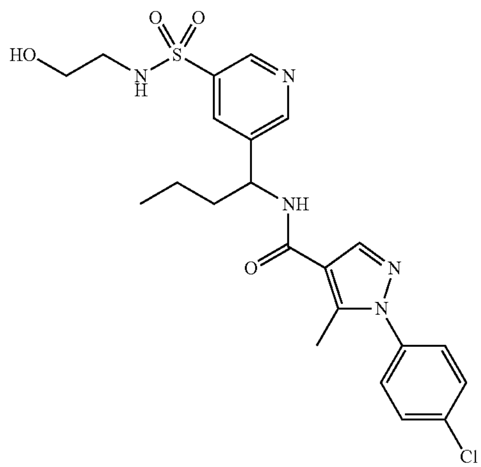 | 1-(4-Chloro-phenyl)-5-methyl-1H-pyrazole-4-carboxylic acid {1-[5-(2-hydroxy-ethylsulfamoyl)-pyridin-3-yl]-butyl}-amide | 493 |
| 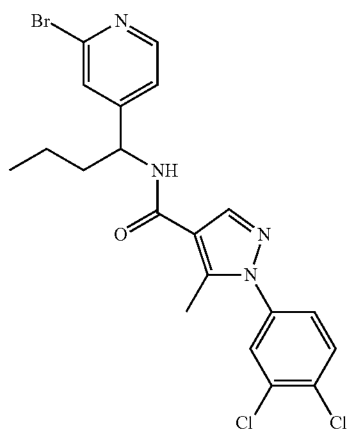 | 1-(3,4-Dichloro-phenyl)-5-methyl-1H-pyrazole-4-carboxylic acid [1-(2-bromo-pyridin-4-yl)-butyl]-amide | 481, 483 |
| 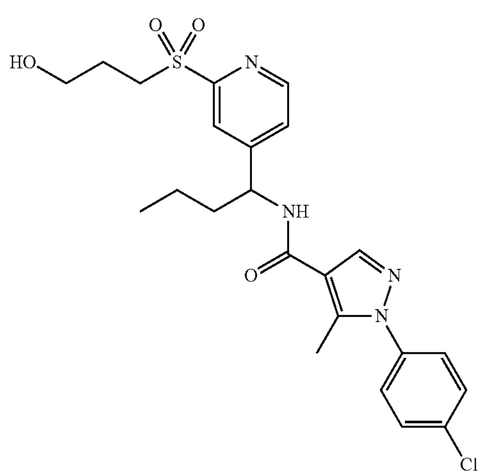 | 1-(4-Chloro-phenyl)-5-methyl-1H-pyrazole-4-carboxylic acid {1-[2-(3-hydroxy-propane-1-sulfonyl)-pyridin-4-yl]-butyl}-amide | 491 |

TABLE 1-continued

| STRUCTURE | Name | Observed mass ([M + H]) |
|---|---|---|
| 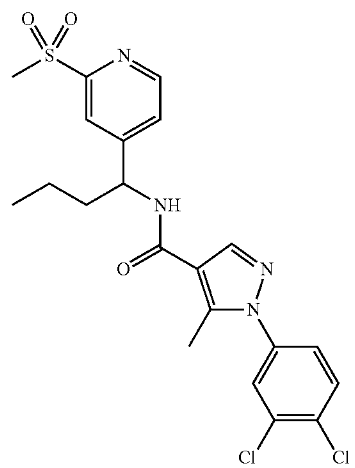 | 1-(3,4-Dichloro-phenyl)-5-methyl-1H-pyrazole-4-carboxylic acid [1-(2-methanesulfonyl-pyridin-4-yl)-butyl]-amide | 482 |
| 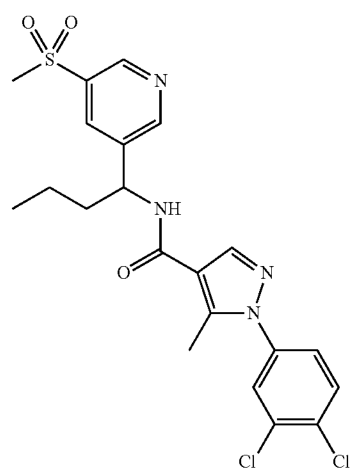 | 1-(3,4-Dichloro-phenyl)-5-methyl-1H-pyrazole-4-carboxylic acid [1-(5-methanesulfonyl-pyridin-3-yl)-butyl]-amide | 482 |
| 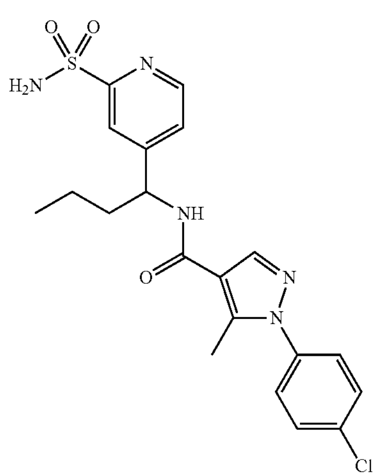 | 1-(4-Chloro-phenyl)-5-methyl-1H-pyrazole-4-carboxylic acid [1-(2-sulfamoyl-pyridin-4-yl)-butyl]-amide | 448 |

TABLE 1-continued

| STRUCTURE | Name | Observed mass ([M + H]) |
|---|---|---|
| 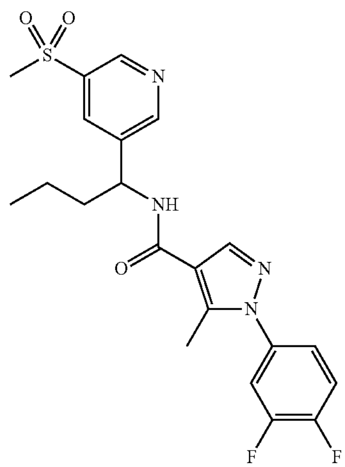 | 1-(3,4-Difluoro-phenyl)-5-methyl-1H-pyrazole-4-carboxylic acid [1-(5-methanesulfonyl-pyridin-3-yl)-butyl]-amide | 450 |
| 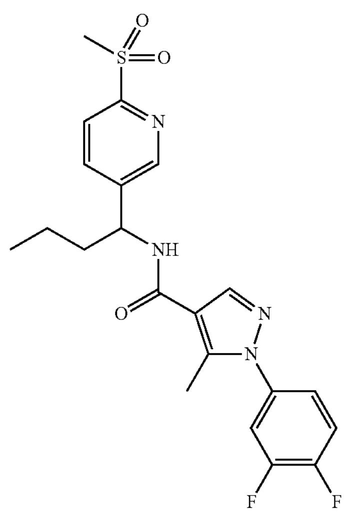 | 1-(3,4-Difluoro-phenyl)-5-methyl-1H-pyrazole-4-carboxylic acid [1-(6-methanesulfonyl-pyridin-3-yl)-butyl]-amide | 449 |
| 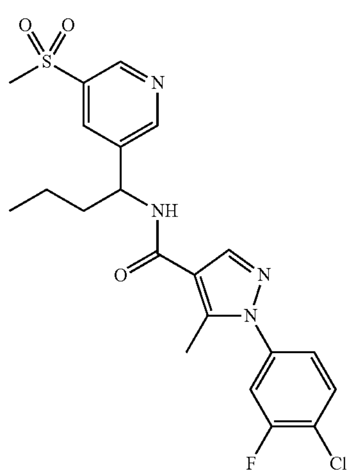 | 1-(4-Chloro-3-fluoro-phenyl)-5-methyl-1H-pyrazole-4-carboxylic acid [1-(5-methanesulfonyl-pyridin-3-yl)-butyl]-amide | 466 |

TABLE 1-continued

| STRUCTURE | Name | Observed mass ([M + H]) |
|---|---|---|
| 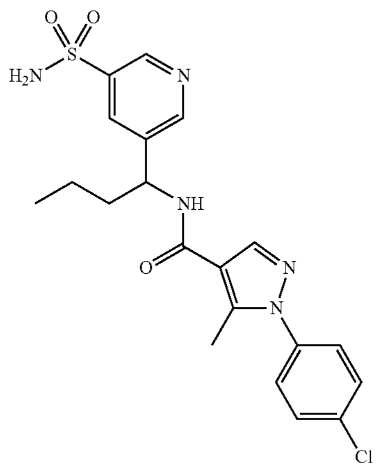 | 1-(4-Chloro-phenyl)-5-methyl-1H-pyrazole-4-carboxylic acid [1-(5-sulfamoyl-pyridin-3-yl)-butyl]-amide | 449 |
| 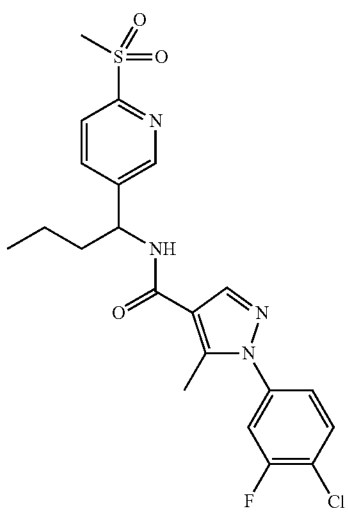 | 1-(4-Chloro-3-fluoro-phenyl)-5-methyl-1H-pyrazole-4-carboxylic acid [1-(6-methanesulfonyl-pyridin-3-yl)-butyl]-amide | 466 |
| 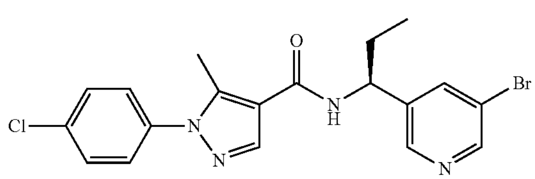 | 1-(4-Chloro-phenyl)-5-methyl-1H-pyrazole-4-carboxylic acid [(S)-1-(5-bromo-pyridin-3-yl)-propyl]-amide | 436, 438 |
| 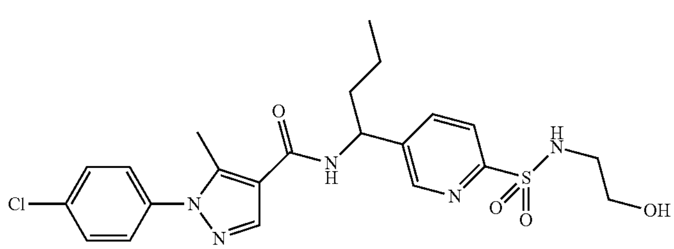 | 1-(4-Chloro-phenyl)-5-methyl-1H-pyrazole-4-carboxylic acid {1-[6-(2-hydroxy-ethylsulfamoyl)-pyridin-3-yl]-butyl}-amide | 493 |

TABLE 1-continued

| STRUCTURE | Name | Observed mass ([M + H]) |
|---|---|---|
| | 1-(4-Chloro-phenyl)-5-methoxymethyl-1H-pyrazole-4-carboxylic acid [1-(6-bromo-pyridin-3-yl)-butyl]-amide | 478, 480 |
| 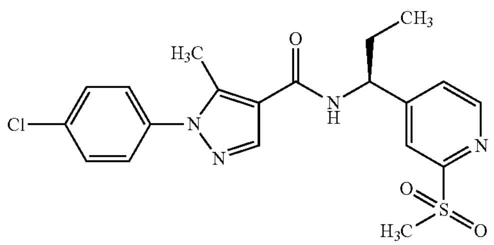 | 1-(4-Chloro-phenyl)-5-methyl-1H-pyrazole-4-carboxylic acid [(S)-1-(2-methanesulfonyl-pyridin-4-yl)-propyl]-amide | 434 |
| 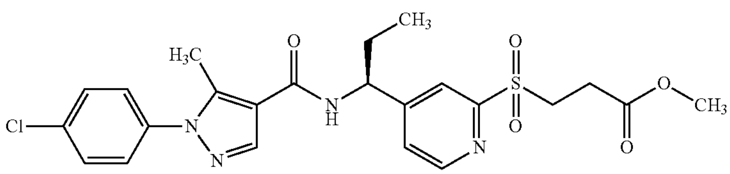 | 3-[4-((S)-1-{[1-(4-Chloro-phenyl)-5-methyl-1H-pyrazole-4-carbonyl]-amino}-propyl)-pyridine-2-sulfonyl]-propionic acid methyl ester | 506 |
| 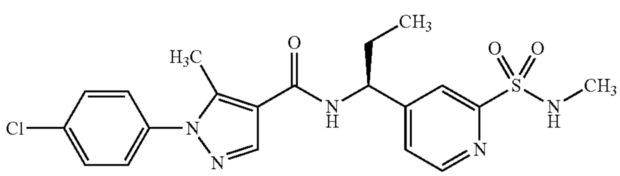 | 1-(4-Chloro-phenyl)-5-methyl-1H-pyrazole-4-carboxylic acid [(S)-1-(2-methylsulfamoyl-pyridin-4-yl)-propyl]-amide | 449 |
| 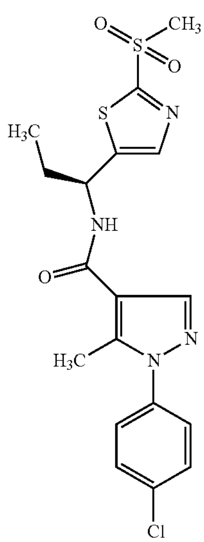 | 1-(4-Chloro-phenyl)-5-methyl-1H-pyrazole-4-carboxylic acid [(S)-1-(2-methanesulfonyl-thiazol-5-yl)-propyl]-amide | 440 |

TABLE 1-continued

| STRUCTURE | Name | Observed mass ([M + H]) |
|---|---|---|
| 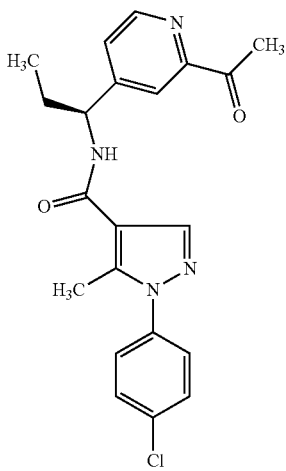 | 4-((S)-1-{[1-(4-Chloro-phenyl)-5-methyl-1H-pyrazole-4-carbonyl]-amino}-propyl)-pyridine-2-carboxylic acid amide | 399 | or a pharmaceutically acceptable salt thereof.

For all compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

In order for this invention to be more fully understood, the following representative examples are set forth. These examples are for the purpose of illustrating embodiments of this invention, and are not to be construed as limiting the scope of the invention in any way since, as recognized by one skilled in the art, particular reagents or conditions could be modified as needed for individual compounds. Starting materials used are either commercially available or easily prepared from commercially available materials by those skilled in the art. Reaction progress may be monitored by conventional methods such as thin layer chromatography (TLC) or liquid chromatography-mass spectroscopy (LC-MS). Intermediates and products may be purified by methods known in the art, including flash chromatography, high performance liquid chromatography (HPLC) or recrystallization. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carbocylic acid and an amine in the presence of 1-(3-dimethylaminopropyl)-3-ethylcarbodiimide (EDC) and 1-hydroxybenzotriazole. Racemic compounds of this invention may be prepared in enantiomerically pure or enriched form by methods known in the art, including separation using chiral HPLC, resolution using a chiral reagent or auxiliary, and other asymmetric methods reported in the chemical literature (for examples, see Liu, G. et al., *J. Am. Chem. Soc.* 1997, 119, 9913; Chelucci, G. et al., *Tetrahedron: Asymmetry* 2006, 17, 3163; Chelucci, G. et al., *Tetrahedron* 2006, 62, 619). Furthermore, if certain functional groups are incompatible under the reaction conditions, protection/deprotection of these groups may be carried out using reagents and conditions readily selected by one of ordinary skill in the art (see, for example, P. G. M. Wuts and T. W. Greene, *Greene's Protective Groups in Organic Synthesis* (John Wiley & Sons: 2006), which is hereby incorporated by reference in its entirety).

The methods described below and in the Synthetic Examples section may be used to prepare the compounds of formula I.

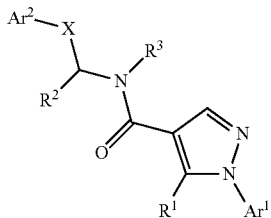

In the schemes below, $Ar_1$, $R^1$-$R^3$ and X shall have the meanings defined in the detailed description of formula I.

Compounds of formula I may be prepared as shown in Scheme 1.

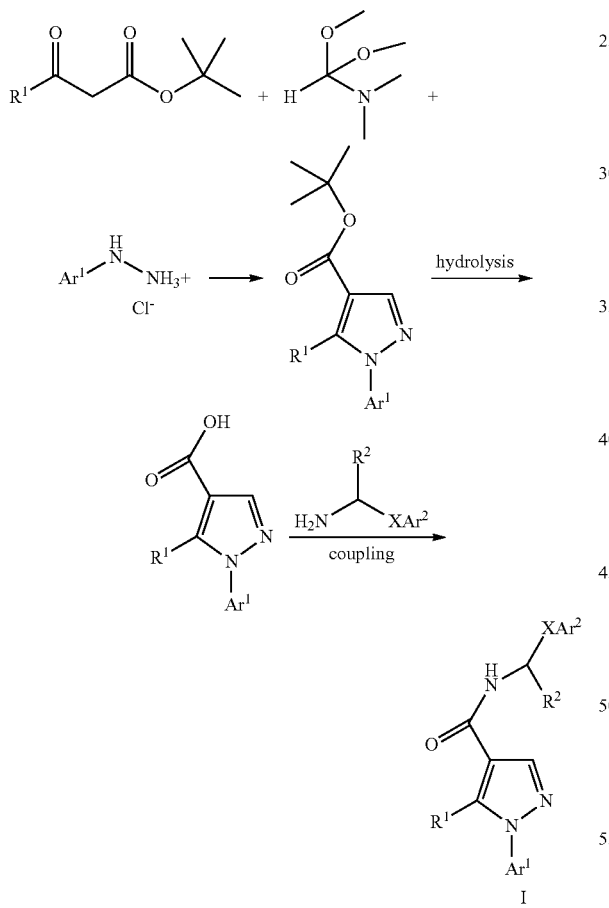

As illustrated above, the desired beta-ketoacetate substituted with $R^1$ with the acid protected, for example as the t-butyl ester, is heated with dimethylformamide dimethylacetal in the presence of a suitable acid such as p-TsOH, preferably in a microwave oven. The resulting intermediate is then reacted with a hydrazine salt bearing $Ar^1$, in the presence of a suitable base such as triethylamine to provide the pyrazole ester. The ester is converted to the acid by hydrolysis, or in the case of the t-butyl ester by treatment of HCl in dioxane, to provide the carboxylic acid. This is coupled with the desired amine using standard coupling conditions known in the art, for example by treatment with O-(7-azabenzotriazol-1-yl)-N,N,N',N'-tetramethyluronium hexafluorophosphate (HATU) in the presence of a suitable base such as morpholine to provide the desired compound of formula (I).

An alternate procedure is illustrated in Scheme 2. In this procedure, the desired beta-ketoacetate ester substituted with $R^1$ is heated with dimethylformamide dimethylacetal Followed by dilution with a suitable solvent such as EtOH and addition of hydrazine hydrate to provide the pyrazole ester substituted with R'. Conversion to the acid, for example by hydrolysis in aqueous base is then followed by coupling with the desired amine as described above. Reaction of the resulting pyrazole with $Ar^2I$ in the presence of CuI, a suitable base such as $K_2CO_3$, and suitable ligand such as trans-N,N'-dimethylcyclohexane-1,2-diamine in a solvent such as DMF provides the desired compound of formula (I).

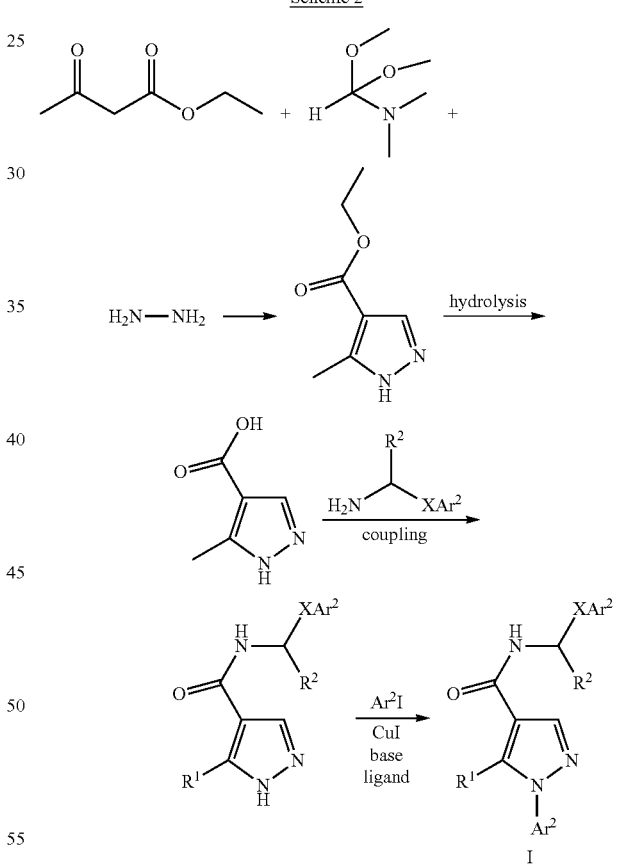

The products of formula (I) prepared as described in the schemes above may be further transformed by methods known in the art and described in the synthetic examples below to produce additional compounds of formula (I). Compounds prepared by the methods illustrated above and in the synthetic examples below are shown in Table 1 in the Detailed Description along with mass spectroscopy data obtained for the compounds.

SYNTHETIC EXAMPLES

Example 1

1-(3-Chloro-4-fluoro-phenyl)-5-methyl-1H-pyrazole-4-carboxylic acid

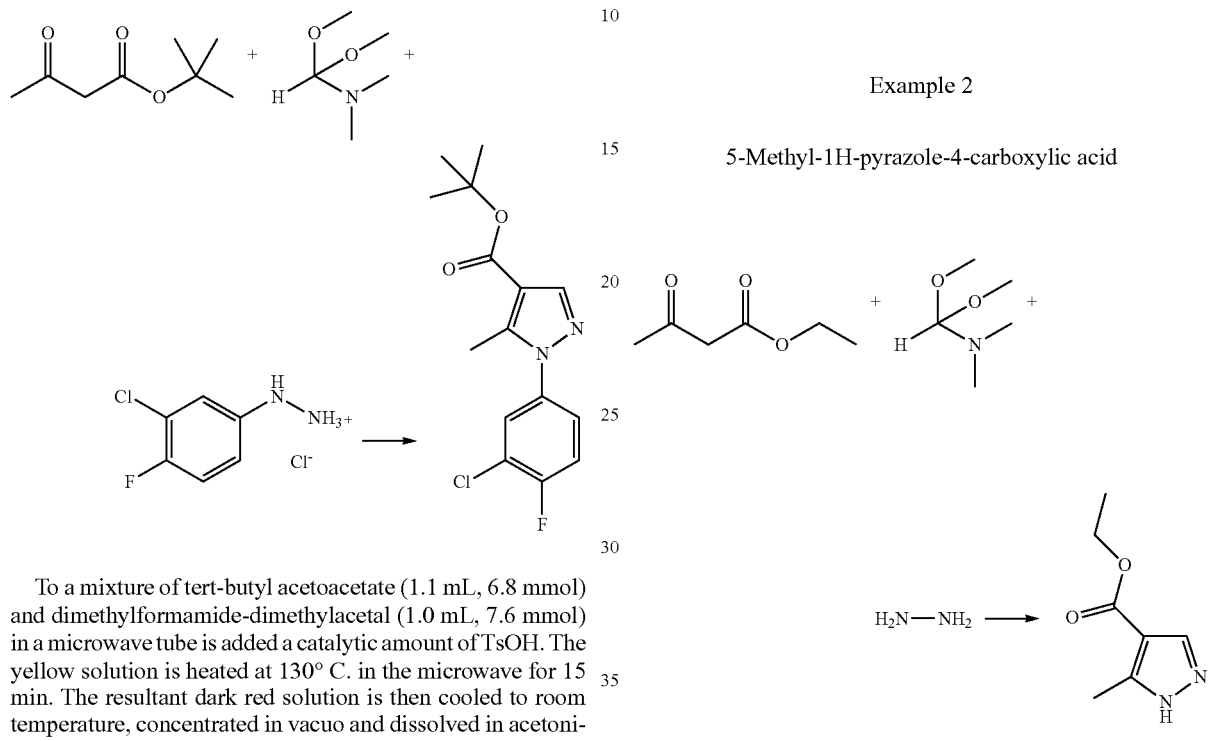

To a mixture of tert-butyl acetoacetate (1.1 mL, 6.8 mmol) and dimethylformamide-dimethylacetal (1.0 mL, 7.6 mmol) in a microwave tube is added a catalytic amount of TsOH. The yellow solution is heated at 130° C. in the microwave for 15 min. The resultant dark red solution is then cooled to room temperature, concentrated in vacuo and dissolved in acetonitrile (5.0 mL). Triethylamine (2.5 mL) is added followed by 3-chloro-4-fluorophenylhydrazine hydrochloride (1.3 g, 6.8 mmol). The dark reddish brown solution is stirred at room temperature for 16 hours. The reaction is diluted with EtOAc (75 mL) and washed with water (7×50 mL). The combined organic phases are dried over $MgSO_4$, filtered and concentrated in vacuo to afford 1-(3-chloro-4-fluoro-phenyl)-5-methyl-1H-pyrazole-4-carboxylic acid tert-butyl ester as a dark brown oil (2.1 g, 100%) which is used without further purification.

1-(3-Chloro-4-fluoro-phenyl)-5-methyl-1H-pyrazole-4-carboxylic acid tert-butyl ester (2.1 g, 6.8 mmol) is treated with cold HCl in dioxane (4.0 N solution, 10 mL, 40 mmol) and stirred for 16 hours at room temperature. The resultant precipitate is collected by filtration, washed with dioxane (2×1 mL) and dried to afford 1-(3-chloro-4-fluoro-phenyl)-5-methyl-1H-pyrazole-4-carboxylic acid as a tan solid (540 mg, 31%).

Example 2

5-Methyl-1H-pyrazole-4-carboxylic acid

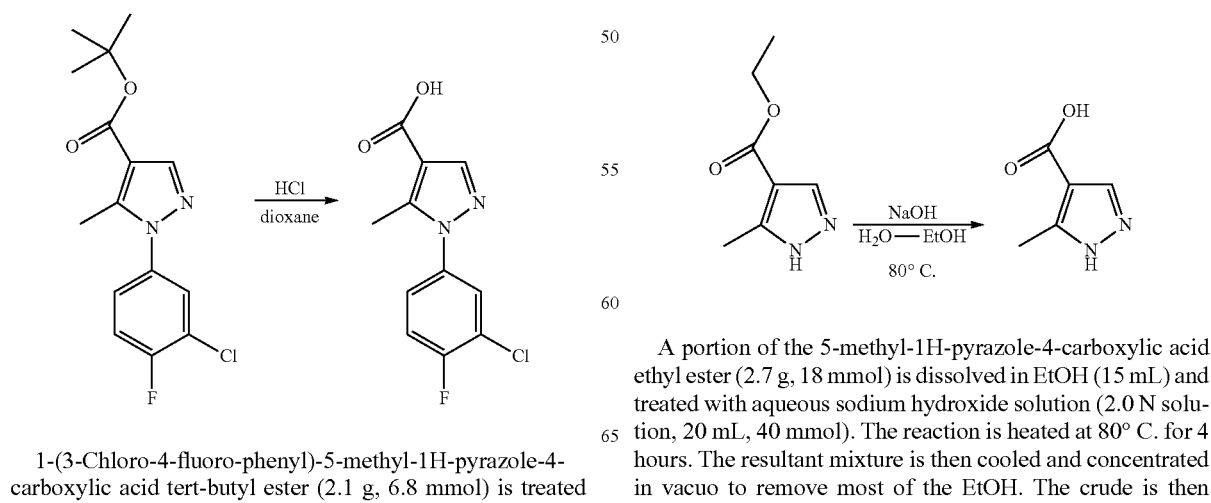

A mixture of ethyl acetoacetate (8.0 mL, 63 mmol) and dimethylformamide-dimethylacetal (8.3 mL, 63 mmol) is heated to reflux for 1 hour. The reaction mixture is cooled to room temperature and diluted with EtOH (70 mL). Hydrazine hydrate (3.0 mL, 63 mmol) is then added and the reaction is heated at 80° C. for 2 hours. The resultant solution is cooled to room temperature and concentrated in vacuo to afford crude 5-methyl-1H-pyrazole-4-carboxylic acid ethyl ester which is used without further purification.

A portion of the 5-methyl-1H-pyrazole-4-carboxylic acid ethyl ester (2.7 g, 18 mmol) is dissolved in EtOH (15 mL) and treated with aqueous sodium hydroxide solution (2.0 N solution, 20 mL, 40 mmol). The reaction is heated at 80° C. for 4 hours. The resultant mixture is then cooled and concentrated in vacuo to remove most of the EtOH. The crude is then acidified with 6N HCl until a precipitate is formed and filtered to afford 5-methyl-1H-pyrazole-4-carboxylic acid as a colorless solid (1.7 g, 74%).

Example 3

1-(4-Chloro-phenyl)-5-methoxymethyl-1H-pyrazole-4-carboxylic acid

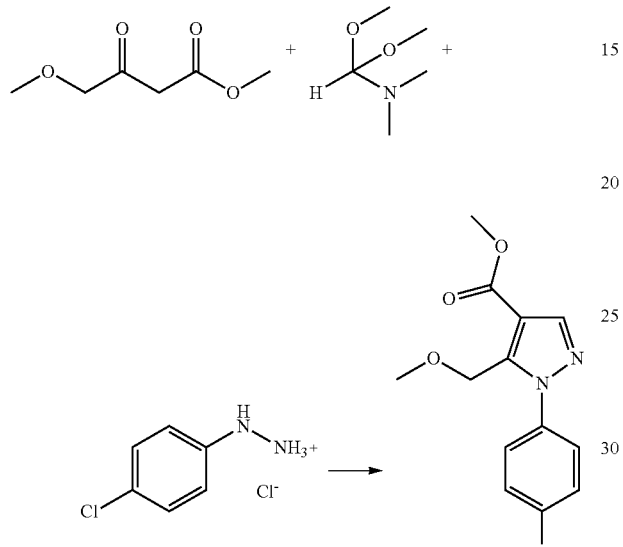

To a mixture of methyl 4-methoxyacetoacetate (5.0 g, 34 mmol) and dimethylformamide-dimethylacetal (6.1 g, 51 mmol) split evenly into two microwave tubes, is added a catalytic amounts of TsOH. The neat solution is heated at 130° C. in the microwave for 15 min. The combined crude is then cooled to room temperature, concentrated in vacuo, dissolved in triethylamine (12 mL) and added to a suspension of 4-chlorophenylhydrazine hydrochloride in acetonitrile (20 mL). After stirring overnight at room temperature, the reaction mixture is concentrated in vacuo and the resultant solid is triturated with MeOH and collected by filtration to afford 1-(4-chloro-phenyl)-5-methoxymethyl-1H-pyrazole-4-carboxylic acid methyl ester (6.0 g, 63%).

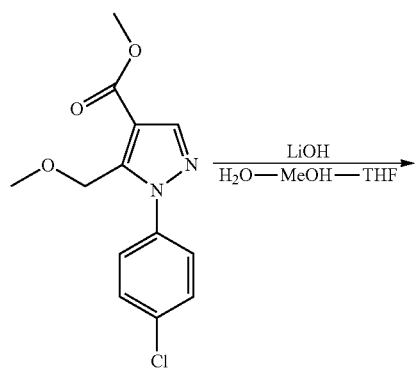

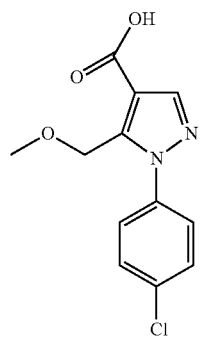

To a solution of 1-(4-chloro-phenyl)-5-methoxymethyl-1H-pyrazole-4-carboxylic acid methyl ester (6.0 g, 21 mmol) in H$_2$O-MeOH-THF (1:1:2) is added lithium hydroxide (620 mg, 26 mmol). After stiffing at room temperature for 18 h, the reaction mixture is concentrated in vacuo and purified by flash chromatography on silica gel (eluted with 15 to 100% EtOAc/hexanes) to afford 1-(4-chloro-phenyl)-5-methoxymethyl-1H-pyrazole-4-carboxylic acid as a white solid (3.8 g, 66%).

Example 4

(S)-1-(6-Trifluoromethyl-pyridin-2-yl)-butylamine hydrochloride

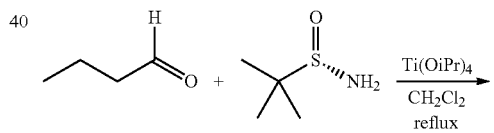

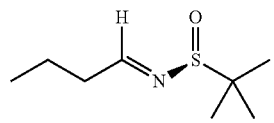

To a solution of (S)-2-methyl-propane-2-sulfinamide (6.7 g, 55 mmol) in dichloromethane (125 mL) is added butyraldehyde (4.0 g, 55 mmol) followed by titanium isopropoxide (32 g, 110 mmol). The reaction is then heated at reflux (bath temperature=60° C.) for 4 hours. The resultant mixture is cooled to room temperature and poured into a stirred mixture of diatomaceous earth (10 g) and water (100 mL). The slurry is stirred for 10 min and then filtered. The organic layer from the filtrate is concentrated in vacuo to afford a crude yellow oil which is purified by flash chromatography on silica gel (eluted with 5 to 30% dioxane/hexanes) to afford (S)-2-methyl-propane-2-sulfinic acid butylideneamide as a colorless oil (7.4 g, 77%).

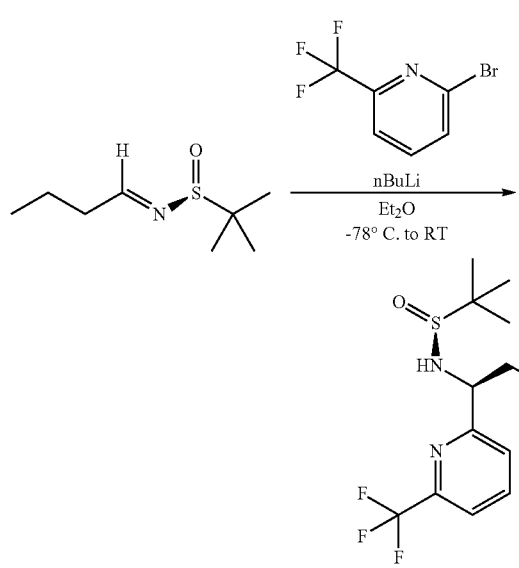

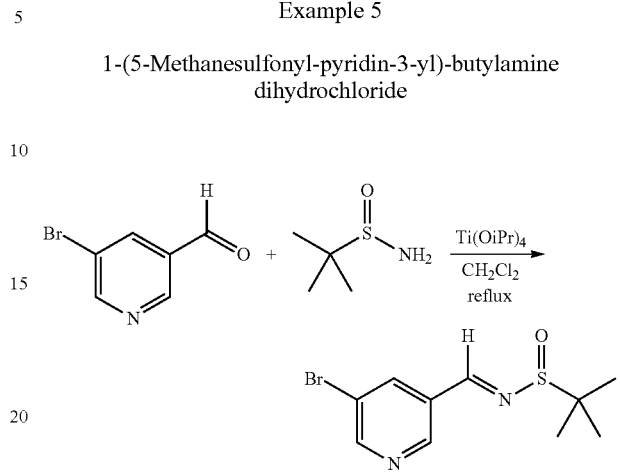

Example 5

1-(5-Methanesulfonyl-pyridin-3-yl)-butylamine dihydrochloride

To a solution of 2-bromo-6-trifluoromethyl-pyridine (480 mg, 2.2 mmol) in anhydrous diethyl ether (20 mL) at −78° C. is added n-butyllithium (1.6 M in hexanes, 1.5 mL, 2.4 mmol) dropwise over 20 min. After stirring at −78° C. for 30 min, (S)-2-methyl-propane-2-sulfinic acid butylideneamide is added. The resultant mixture is stirred at −78° C. for 30 min and is then allowed to warm gradually to room temperature overnight. The reaction mixture is poured into saturated aqueous ammonium chloride solution (30 mL) and extracted with EtOAc (3×30 mL). The combined organic phases are dried over magnesium sulfate, filtered and concentrated in vacuo to afford (S,S)-2-methyl-propane-2-sulfinic acid 1-(6-trifluoromethyl-pyridin-2-yl)-butylamide as a yellow oil (290 mg, 42%).

To a solution of 2-methyl-propane-2-sulfinamide (11 g, 91 mmol) and 5-bromo-3-pyridine-carboxaldehyde (14 g, 75 mmol) in dichloromethane (500 mL) is added titanium isopropoxide (43 g, 150 mmol). The reaction is then heated at reflux (bath temperature=60° C.) for 4 hours. The resultant mixture is cooled to room temperature and poured into a stirred mixture of diatomaceous earth (50 g) and water (150 mL). The slurry is stirred for 10 min and then filtered. The organic layer from the filtrate is washed with brine and dried over sodium sulfate. Filtration and concentration in vacuo affords 2-methyl-propane-2-sulfinic acid 1-(5-bromo-pyridin-3-yl)-methylideneamide as a yellow solid (22 g, 99%).

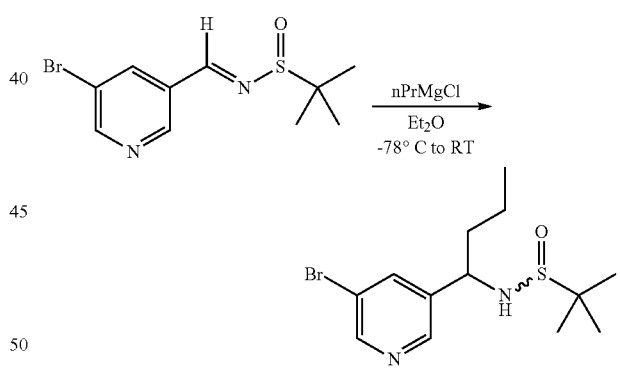

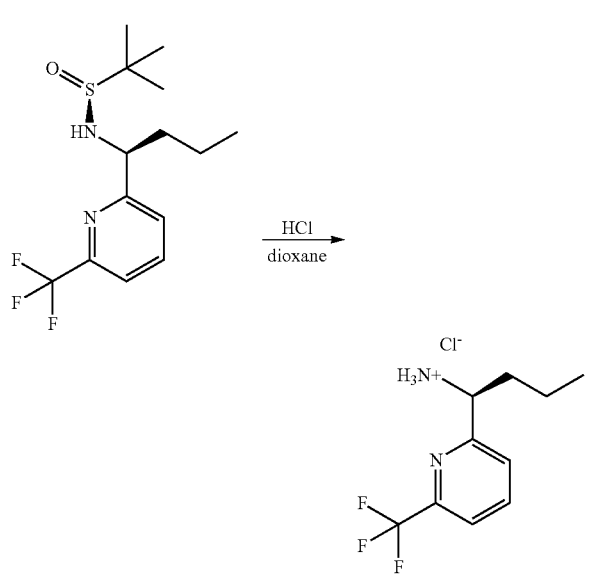

(S,S)-2-Methyl-propane-2-sulfinic acid 1-(6-trifluoromethyl-pyridin-2-yl)-butylamide (290 mg, 0.92 mmol) is treated with HCl in dioxane (4.0 N solution, 10 mL, 40 mmol) at room temperature and stirred for 30 min. The reaction mixture is concentrated in vacuo to afford (S)-1-(6-trifluoromethyl-pyridin-2-yl)-butylamine hydrochloride (200 mg, 88%) which is used without further purification [note: the enantiomeric purity (% ee) has not been determined].

To a solution of 2-methyl-propane-2-sulfinic acid 1-(5-bromo-pyridin-3-yl)-methylideneamide (22 g, 74 mmol) in anhydrous THF (750 mL) at −78° C. is added n-propylmagnesium chloride (2.0 N in ether, 89 mL, 180 mmol) dropwise over 15 min. After stirring at −78° C. for 3 hours, the reaction mixture is then allowed to warm gradually to room temperature overnight. The reaction mixture is quenched by slow addition of saturated aqueous ammonium chloride solution (100 mL) and extracted with EtOAc (2×300 mL). The combined organic phases are washed with brine, dried over sodium sulfate, filtered and concentrated in vacuo. The crude material is purified by flash chromatography on silica gel (eluted with 20 to 50% EtOAc/hexanes) to afford 2-methyl-propane-2-sulfinic acid 1-(5-bromo-pyridin-3-yl)-butylamide (16 g, 65%) as a yellow solid.

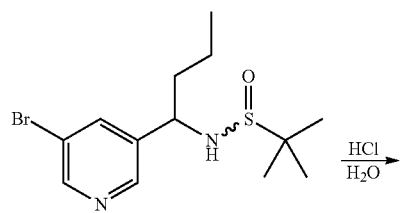

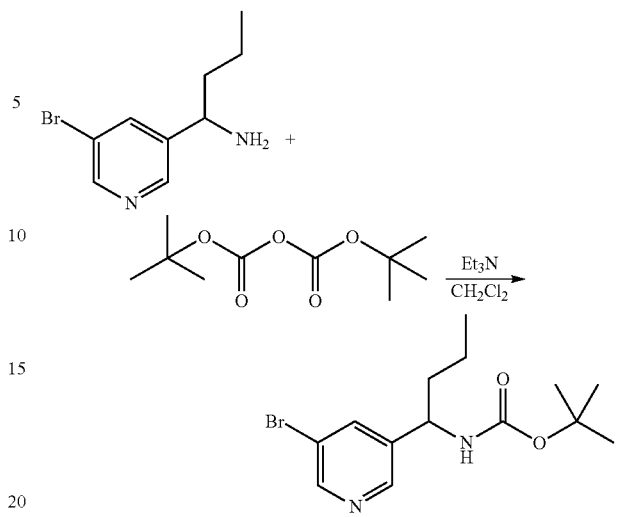

2-Methyl-propane-2-sulfinic acid 1-(5-bromo-pyridin-3-yl)-butylamide (16 g, 48 mmol) is treated with aqueous HCl (3.0 N solution, 400 mL, 1.2 mol) at room temperature and stirred for 5 hours. The reaction mixture is quenched by addition of saturated aqueous sodium carbonate solution until pH 8 and extracted with dichloromethane (3×300 mL). The combined organic phases are dried over $Na_2SO_4$, filtered, and concentrated to afford 1-(5-bromo-pyridin-3-yl)-butylamine (9.5 g, 86%) of as a light brown oil.

The following amines are synthesized in racemic form in an analogous manner:

1-(4-bromo-pyridin-3-yl)-butylamine,
1-(3-bromo-pyridin-4-yl)-butylamine,
1-(5-bromo-pyridin-3-yl)-propylamine.

The following amine is synthesized in enantio-enriched form using (R)-2-methyl-propane-2-sulfinamide in an analogous manner. The enantiopurity is determined to be >93% ee:

(S)-1-(4-fluoro-3-trifluoromethyl-phenyl)-ethylamine.

The following amines are synthesized in enantio-enriched form using (R)-2-methyl-propane-2-sulfinamide in an analogous manner. The enantiopurity has not been determined:

(S)-1-(4-fluoro-3-trifluoromethyl-phenyl)-propylamine,
(S)-1-(4-fluoro-3-trifluoromethyl-phenyl)-butylamine,
(S)-1-(4-fluoro-3-trifluoromethyl-phenyl)-allylamine,
(S)-1-(3-bromo-phenyl)-ethylamine,
(S)-1-(3-bromo-phenyl)-butylamine,
(S)-1-(3-bromo-phenyl)-allylamine,
(S)-1-(3-bromo-phenyl)-2-methyl-propylamine,
(S)-1-(3-bromo-phenyl)-3,3-dimethyl-butylamine,
(S)-1-(3-bromo-phenyl)-pentylamine,
(S)-1-(3-bromo-phenyl)-hexylamine,
(S)-(4-fluoro-3-trifluoromethyl-phenyl)-phenyl-methylamine,
(S)-(3-bromo-phenyl)-cyclopropyl-methylamine,
(S)-1-(3-bromo-phenyl)-but-3-enylamine,
(S)-1-(3-bromo-phenyl)-pent-4-enylamine,
(S)-2-(3-fluoro-phenyl)-1-methyl-ethylamine,
(S)-1-(3-trifluoromethyl-phenyl)-butylamine,
(S)-1-(3-trifluoromethyl-phenyl)-hex-5-enylamine,
(S)-1-(2-bromo-pyridin-4-yl)-propylamine.

To a solution of 1-(5-bromo-pyridin-3-yl)-butylamine (6.0 g, 26 mmol) in 250 mL of dichloromethane is added triethylamine (17 mL). After 5 min, di-tert-butyl carbonate (19 g, 86 mmol) is added in one portion. The resultant mixture is stirred at room temperature for 16 hours. The reaction is quenched by addition of saturated aqueous sodium bicarbonate solution until pH 8. The layers are separated. The aqueous layer is extracted with dichloromethane (3×50 mL). The combined organic layers are dried over sodium sulfate and concentrated in vacuo. The crude material is purified by flash chromatography on silica gel (eluted with 0 to 25% EtOAc/hexanes) to yield [1-(5-bromo-pyridin-3-yl)-butyl]-carbamic acid tert-butyl ester (6.5 g, 76%) as a colorless oil.

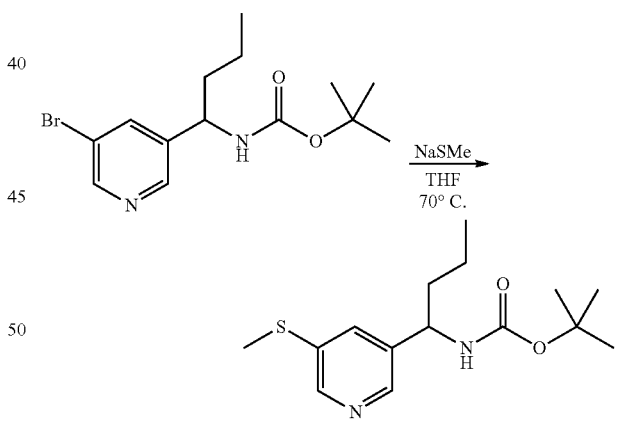

A solution of [1-(5-bromo-pyridin-3-yl)-butyl]-carbamic acid tert-butyl ester (6.3 g, 19 mmol) and sodium thiomethoxide (2.7 g, 38 mmol) in anhydrous THF (27 mL) is heated at 70° C. After 2 hours the reaction is cooled to room temperature and water (200 mL) is added. The resultant mixture is extracted with ethyl acetate (3×200 mL). The combined organic layers are combined, washed with brine, dried over sodium sulfate and concentrated in vacuo. The residue is purified by flash chromatography on silica gel (eluted with 0 to 60% EtOAc/hexanes) to afford [1-(5-methylsulfanyl-pyridin-3-yl)-butyl]-carbamic acid tert-butyl ester (3.9 g, 68%) as a thick light yellow oil.

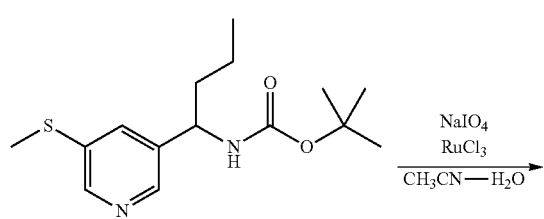

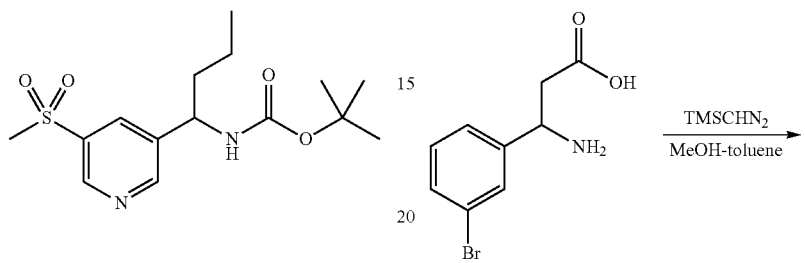

To a solution of [1-(5-methylsulfanyl-pyridin-3-yl)-butyl]-carbamic acid tert-butyl ester (3.9 g, 13 mmol) in acetonitrile (80 mL) and water (38 mL) is added sodium periodate (7.0 g, 33 mmol) and ruthenium (III) chloride (270 mg, 1.3 mmol). The resultant mixture is stirred at room temperature for 1.5 hour. The reaction is then diluted with water (50 mL) and extracted with dichloromethane (3×100 mL). The combined organic layers are filtered through Diatomaceous earth. The filtrate is dried over magnesium sulfate and concentrated in vacuo. The resultant black residue is purified by flash chromatography on silica gel (eluted with 0 to 70% EtOAc/hexanes). The combined product-containing fractions are decolorized with activated charcoal and filtered. Concentration in vacuo affords [1-(5-methanesulfonyl-pyridin-3-yl)-butyl]-carbamic acid tert-butyl ester (3.2 g, 74%) as a dark foam.

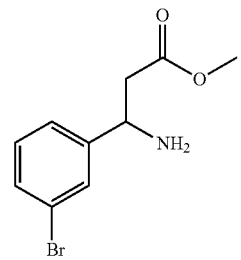

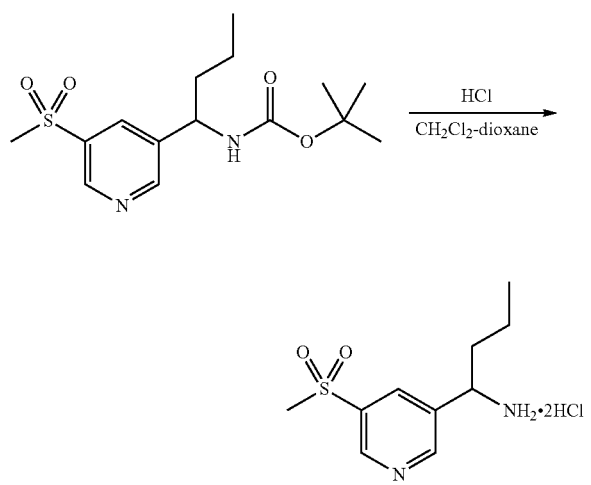

A suspension of [1-(5-methanesulfonyl-pyridin-3-yl)-butyl]-carbamic acid tert-butyl ester (3.2 g, 9.6 mmol) in dichloromethane (12 mL) is treated HCl in dioxane (4.0 N, 24 mL, 96 mmol) and stirred for 30 min. The solvent is then removed in vacuo. The resultant residue is triturated with anhydrous ethyl ether (50 mL) and filtered (note: the collected solids are hygroscopic and turn into a liquid when left exposed to air.) Methanol is added and the solution is concentrated in vacuo to yield 1-(5-methanesulfonyl-pyridin-3-yl)-butylamine dihydrochloride (2.8 g, 100%) as a dark brown solid.

Example 6

3-Amino-3-(3-bromo-phenyl)-propionic acid methyl ester

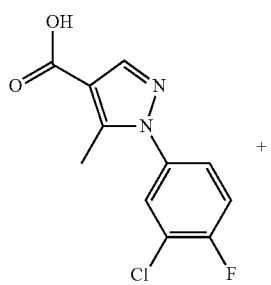

To a solution of 3-amino-3-(3-bromo-phenyl)-propionic acid (1.0 g, 4.1 mmol) in methanol-toluene (100 mL; 1:1 solution) at room temperature is added trimethylsilyl diazomethane (2.0 M solution in hexanes, 20 mL, 40 mmol). After 30 min, excess trimethylsilyl diazomethane is quenched by addition of glacial acetic acid (5 mL). Concentration in vacuo affords of 3-amino-3-(3-bromo-phenyl)-propionic acid methyl ester (1.0 g, 95%) as a colorless liquid which solidifies upon standing.

Example 7

1-(3-Chloro-4-fluoro-phenyl)-5-methyl-1H-pyrazole-4-carboxylic acid [1-(5-methanesulfonyl-pyridin-3-yl)-butyl]-amide -continued

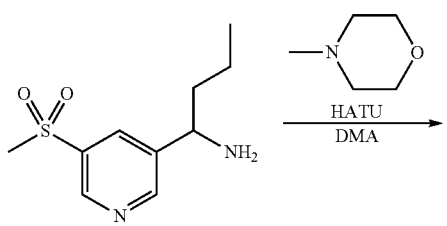

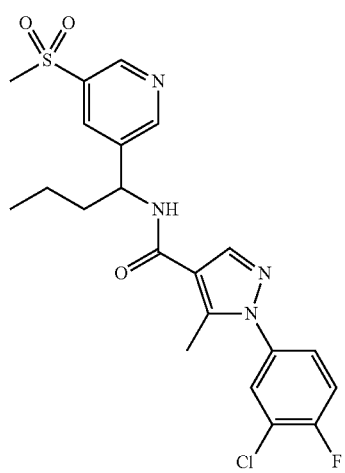

A solution of 1-(3-chloro-4-fluoro-phenyl)-5-methyl-1H-pyrazole-4-carboxylic acid (35 mg, 0.22 mmol) in 0.5 mL DMA is treated with O-(7-azabenzotriazol-1-yl)-N,N,N',N'-tetramethyluronium hexafluorophosphate (HATU) (56 mg, 0.22 mmol) and stirred for 15 min. Meanwhile a solution of 1-(5-methanesulfonyl-pyridin-3-yl)-butylamine (35 mg, 0.15 mmol) and N-methylmorpholine (66 µL, 0.60 mmol) in 0.5 mL DMA is prepared. The resultant pale yellow solution is stirred at room temperature for 5 min and added to the acid/HATU solution. After 16 hours, the reaction is evaporated to dryness and purified by reverse phase HPLC (eluted with 10 to 90% CH₃CN/H₂O and 0.1% TFA as additive) to afford 1-(3-chloro-4-fluoro-phenyl)-5-methyl-1H-pyrazole-4-carboxylic acid [1-(5-methanesulfonyl-pyridin-3-yl)-butyl]-amide (32 mg, 46%).

Example 8

1-(5-Chloro-pyridin-2-yl)-5-methyl-1H-pyrazole-4-carboxylic acid [(S)-1-(3-trifluoromethyl-phenyl)-ethyl]-amide -continued

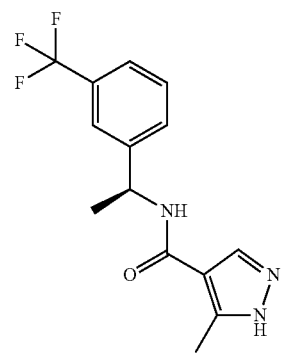

To 5-methyl-1H-pyrazole-4-carboxylic acid (390 mg, 3.1 mmol) in DMF (10 mL) is added triethylamine (1.2 mL, 9.4 mmol) and benzotriazole-1-yl-oxy-tris-(dimethylamino)-phosphonium hexafluorophosphate (PyBOP) (1.8 g, 3.5 mmol). After stirring for 5 min at room temperature, (S)-1-(3-trifluoromethyl-phenyl)-ethylamine (650 mg, 3.4 mmol) is added and the reaction is stirred at room temperature for 2 days. The mixture is then diluted with saturated ammonium chloride and extracted with EtOAc (4×15 mL). The combined organic layer is washed with saturated NaHCO₃ solution (20 mL) followed by brine (20 mL), dried over sodium sulfate, filtered and concentrated in vacuo. The crude material is purified by flash chromatography on silica gel (eluted with 0 to 60% EtOAc/hexanes) followed by recrystallization from ether/hexanes to provide 5-methyl-1H-pyrazole-4-carboxylic acid [(S)-1-(3-trifluoromethyl-phenyl)-ethyl]-amide as a colorless solid (770 mg, 84%).

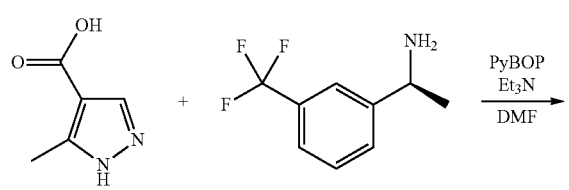

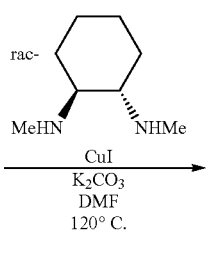

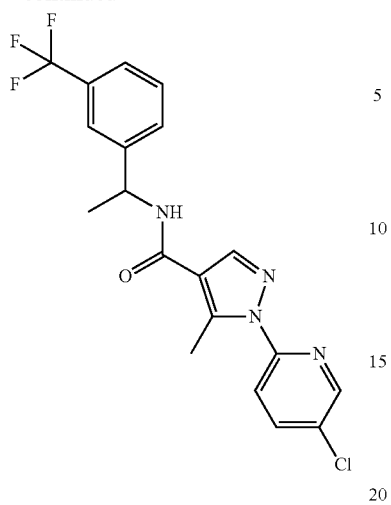

5-Methyl-1H-pyrazole-4-carboxylic acid [(S)-1-(3-trifluoromethyl-phenyl)-ethyl]-amide (70 mg, 0.24 mmol), copper(I) iodide (10 mg, 0.05 mmol), 5-chloro-2-iodopyridine (75 mg, 0.31 mmol) and potassium carbonate (75 mg, 0.54 mmol) are added to a reaction vial with a septum top which is then evacuated and filled with argon for 3 cycles. DMF (2 mL, degassed) and racemic trans-N,N'-dimethylcyclohexane-1,2-diamine (15 µL, 0.10 mmol) are added and the reaction is heated at 120° C. for 17 hours. The resultant mixture is cooled to room temperature, diluted with saturated aqueous ammonium chloride (15 mL) and extracted with EtOAc (3×20 mL). The combined organic layers is washed with saturated aqueous sodium bicarbonate (15 mL) followed by brine (15 mL), dried over sodium sulfate, filtered and concentrated in vacuo to provide a crude solid. Recrystallization from ether/hexanes provides 1-(5-chloro-pyridin-2-yl)-5-methyl-1H-pyrazole-4-carboxylic acid [(S)-1-(3-trifluoromethyl-phenyl)-ethyl]-amide as a colorless solid (38 mg, 40%). (For references, see Buchwald, et al., *J. Org. Chem.* 2004, 69, 5578; Buchwald, et al., *J. Am. Chem. Soc.* 2002, 124, 11684).

Example 9

1-(4-Chloro-phenyl)-5-methyl-1H-pyrazole-4-carboxylic acid [1-(5-bromo-pyridin-3-yl)-butyl]-amide

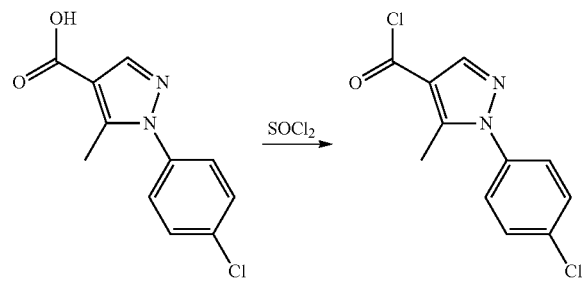

A solution of 1-(4-chloro-phenyl)-5-methyl-1H-pyrazole-4-carboxylic acid (1.5 g, 6.3 mmol) in thionyl chloride (18 mL) is warmed to reflux for 1 hour. After cooling to room temperature, the reaction mixture is concentrated in vacuo to afford 1-(4-chloro-phenyl)-5-methyl-1H-pyrazole-4-carbonyl chloride as a tan solid (1.6 g, 100%) which is used without further purification.

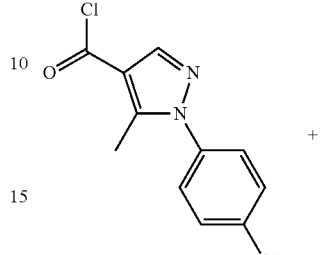

+

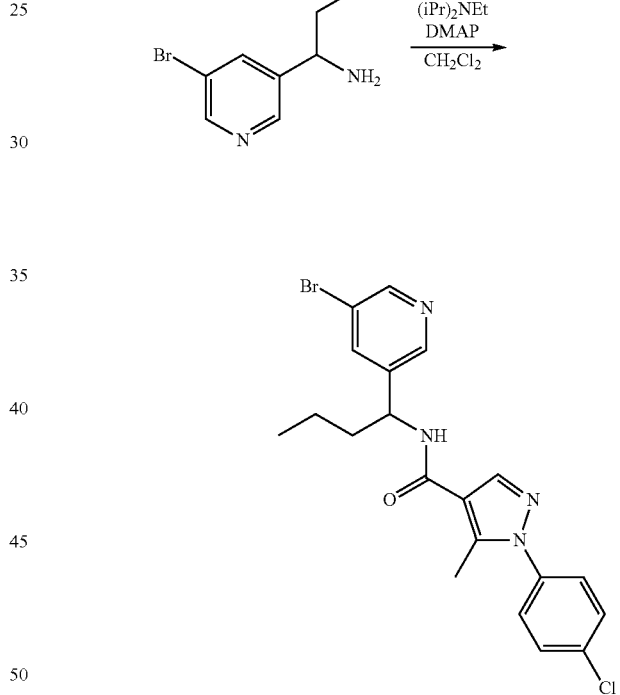

A solution of 1-(5-bromo-pyridin-3-yl)-butylamine (470 mg, 2.0 mmol), diisopropylethylamine (0.82 mL, 4.7 mmol) and DMAP (19 mg, 0.16 mmol) in CH₂Cl₂ (20 mL) is treated with 1-(4-chloro-phenyl)-5-methyl-1H-pyrazole-4-carbonyl chloride (400 mg, 1.6 mmol) and stirred for 15 hours. The reaction mixture is then diluted with CH₂Cl₂ (50 mL), washed with saturated aqueous ammonium chloride (2×50 mL) and brine (50 mL), dried over magnesium sulfate, filtered and concentrated in vacuo. The crude material is purified by flash chromatography on silica gel (eluted with 20 to 50% EtOAc/hexanes) to provide 1-(4-chloro-phenyl)-5-methyl-1H-pyrazole-4-carboxylic acid [1-(5-bromo-pyridin-3-yl)-butyl] amide as a colorless foam-solid (540 mg, 78%).

Example 10

1-(3,4-Dichloro-phenyl)-5-methyl-1H-pyrazole-4-carboxylic acid [1-(3-bromo-phenyl)-2-diethylcarbamoyl-ethyl]-amide

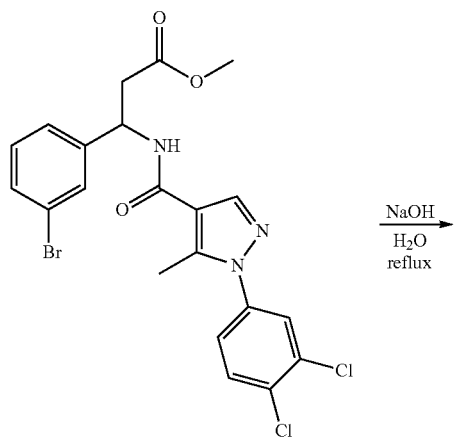

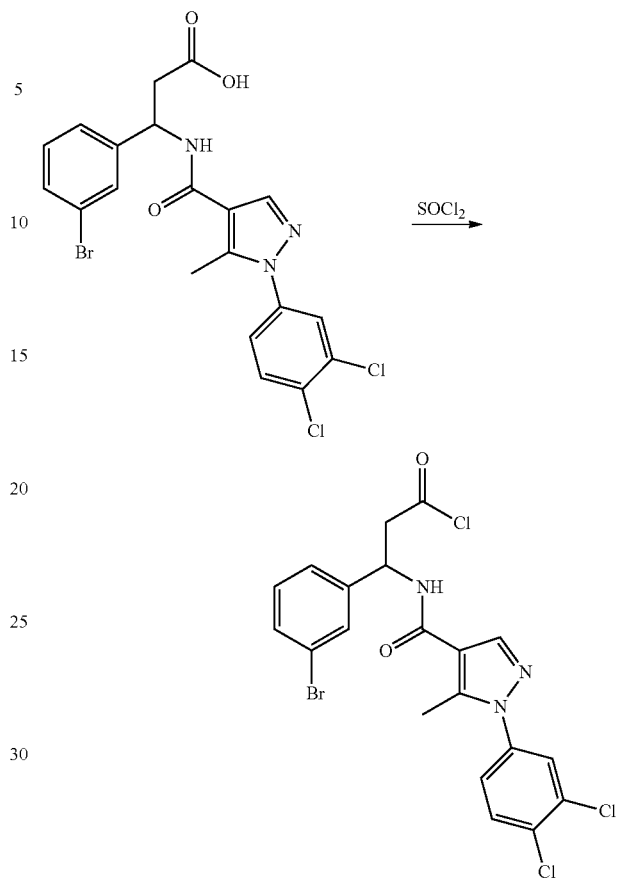

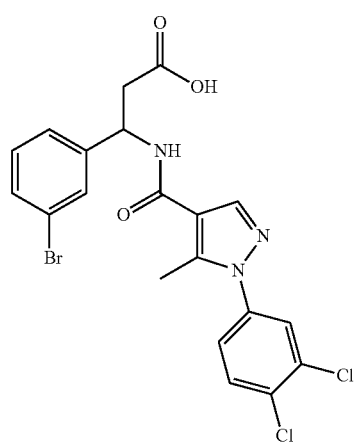

3-(3-Bromo-phenyl)-3-{[1-(3,4-dichloro-phenyl)-5-methyl-1H-pyrazole-4-carbonyl]-amino}-propionic acid methyl ester (1.5 g, 2.9 mmol) is treated with aqueous NaOH (1.0 N solution, 60 mL, 60 mmol) and stirred at reflux for 1 hour. After cooling to room temperature, the reaction mixture is acidified with aqueous 1N HCl. The resultant precipitate is collected by filtration and dried in vacuo to afford 3-(3-bromo-phenyl)-3-{[1-(3,4-dichloro-phenyl)-5-methyl-1H-pyrazole-4-carbonyl]-amino}-propionic acid as a off-white solid (870 mg, 60%).

A solution of 3-(3-bromo-phenyl)-3-{[1-(3,4-dichloro-phenyl)-5-methyl-1H-pyrazole-4-carbonyl]-amino}-propionic acid (870 mg, 1.8 mmol) in thionyl chloride (40 mL) is heated at reflux for 1 hour. After cooling to room temperature, the reaction mixture is concentrated in vacuo to afford 3-(3-bromo-phenyl)-3-{[1-(3,4-dichloro-phenyl)-5-methyl-1H-pyrazole-4-carbonyl]-amino}-propionyl chloride as an off-white solid (880 mg, 98%) which is used without further purification.

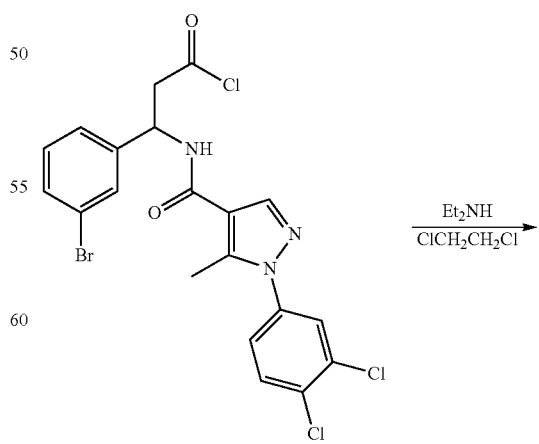

-continued

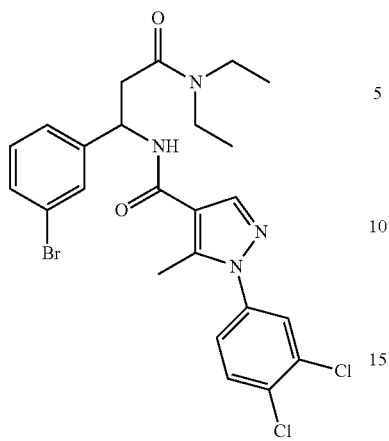

A solution 3-(3-bromo-phenyl)-3-{[1-(3,4-dichloro-phenyl)-5-methyl-1H-pyrazole-4-carbonyl]-amino}-propionyl chloride (100 mg, 0.19 mmol) in 1,2-dichloroethane (3 mL) is treated with diethylamine (28 mg, 0.38 mmol) in one portion and stirred at room temperature for 2 hours. The reaction mixture is concentrated in vacuo and purified by flash chromatography on silica gel (eluted with 1 to 4% MeOH/CH₂Cl₂) to afford 1-(3,4-dichloro-phenyl)-5-methyl-1H-pyrazole-4-carboxylic acid [1-(3-bromo-phenyl)-2-diethylcarbamoyl-ethyl]-amide as a white foam (6.0 mg, 6.0%).

Example 11

1-(4-Chloro-phenyl)-5-methyl-1H-pyrazole-4-carboxylic acid [(S)-3-hydroxy-1-(3-trifluoromethyl-phenyl)-propyl]-amide

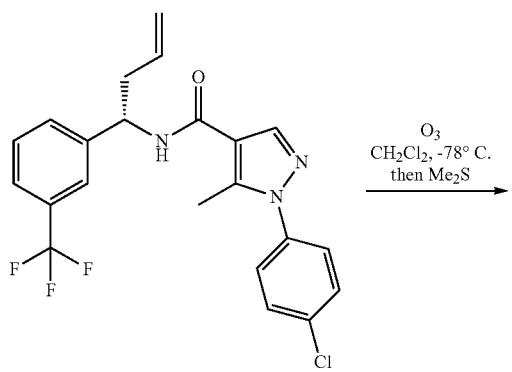

-continued

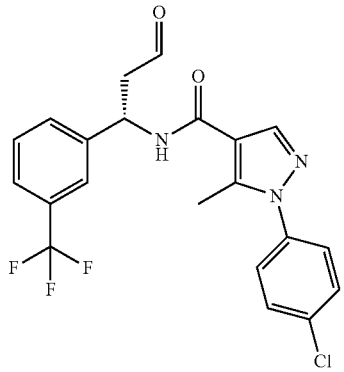

A solution of 1-(4-chloro-phenyl)-5-methyl-1H-pyrazole-4-carboxylic acid [(S)-1-(3-trifluoromethyl-phenyl)-but-3-enyl]-amide (400 mg, 0.92 mmol) in CH₂Cl₂ (25 mL) at −78° C. is treated with ozone gas by bubbling for 30 min until a blue color is sustained. After stiffing for an additional hour at −78° C., dimethylsulfide (4.2 mL) is added. The reaction mixture is warmed to room temperature and concentrated in vacuo to afford 1-(4-chloro-phenyl)-5-methyl-1H-pyrazole-4-carboxylic acid [(S)-3-oxo-1-(3-trifluoromethyl-phenyl)-propyl]-amide (390 mg, 98%) which is used without further purification.

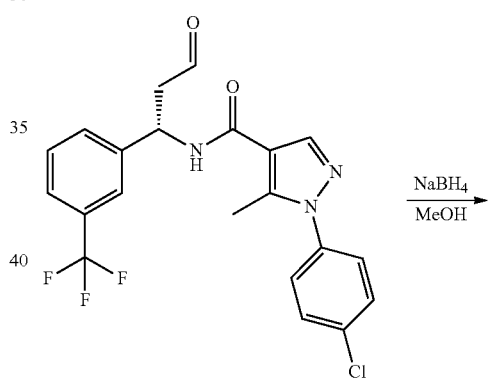

To a solution of 1-(4-chloro-phenyl)-5-methyl-1H-pyrazole-4-carboxylic acid [(S)-3-oxo-1-(3-trifluoromethyl-phenyl)-propyl]-amide (80 mg, 0.18 mmol) in methanol (3 mL) is added sodium borohydride (50 mg, 1.3 mmol). After 16 hours, the crude reaction mixture is purified directly by flash chromatography on silica gel (eluted with 4 to 10% MeOH/CH₂Cl₂) to afford 1-(4-chloro-phenyl)-5-methyl-1H-pyrazole-4-carboxylic acid [(S)-3-hydroxy-1-(3-trifluoromethyl-phenyl)-propyl]-amide as a white solid (36 mg, 45%).

Example 12

1-(4-Chloro-phenyl)-5-methyl-1H-pyrazole-4-carboxylic acid [(S)-5-(4-methyl-piperidin-1-yl)-5-oxo-1-(3-trifluoromethyl-phenyl)-pentyl]-amide

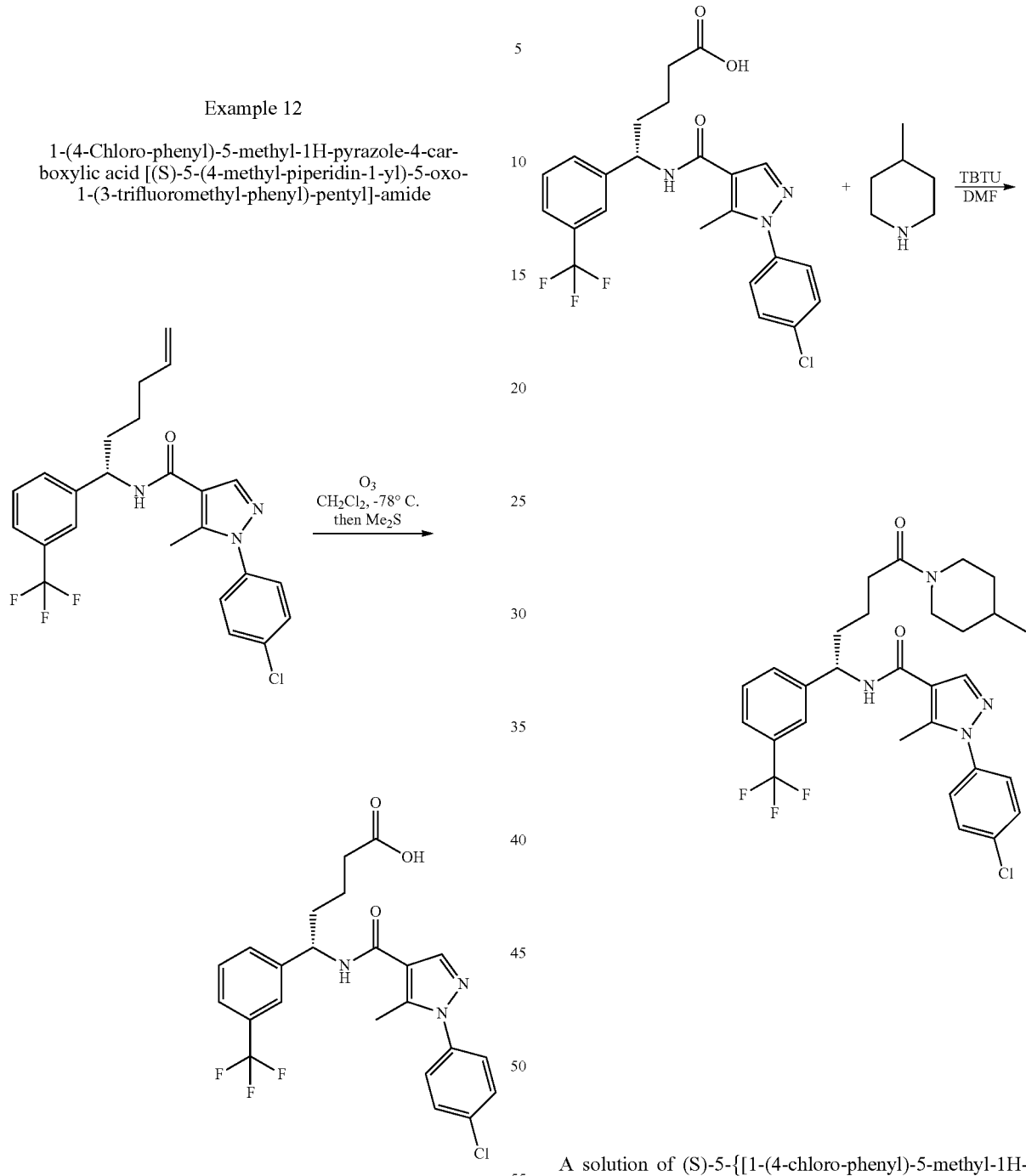

A solution of 1-(4-chloro-phenyl)-5-methyl-1H-pyrazole-4-carboxylic acid [(S)-1-(3-trifluoromethyl-phenyl)-hex-5-enyl]-amide (60 mg, 0.13 mmol) in $CH_2Cl_2$ (10 mL) at −78° C. is treated with ozone gas by bubbling until a blue color is sustained. After stirring for an additional 1 hour at −78° C., dimethylsulfide (1.0 mL) is added. The reaction mixture is allowed to warm to room temperature and stirred overnight. Concentration in vacuo gives (S)-5-{[1-(4-chloro-phenyl)-5-methyl-1H-pyrazole-4-carbonyl]-amino}-5-(3-trifluoromethyl-phenyl)-pentanoic acid which is used without further purification.

A solution of (S)-5-{[1-(4-chloro-phenyl)-5-methyl-1H-pyrazole-4-carbonyl]-amino}-5-(3-trifluoromethyl-phenyl)-pentanoic acid (60 mg, 0.13 mmol) and 4-methylpiperidine (40 mg, 0.40 mmol) in DMF (3 mL) is treated with O-(1H-benzotriazol-1-yl)-1,1,3,3-tetramethyl-uronium tetrafluoroborate (TBTU) (64 mg, 0.20 mmol). The reaction mixture is stirred at room temperature for 16 hours. The crude reaction mixture is purified directly by preparative reverse phase HPLC (eluted with 10 to 90% $CH_3CN/H_2O$ and 0.1% TFA as additive) to afford 1-(4-chloro-phenyl)-5-methyl-1H-pyrazole-4-carboxylic acid [(S)-5-(4-methyl-piperidin-1-yl)-5-oxo-1-(3-trifluoromethyl-phenyl)-pentyl]-amide (21 mg, 30% over 2 steps).

Example 13

1-(4-Chloro-phenyl)-5-methyl-1H-pyrazole-4-carboxylic acid [(S)-5-(pyridin-3-ylamino)-1-(3-trifluoromethyl-phenyl)-pentyl]-amide

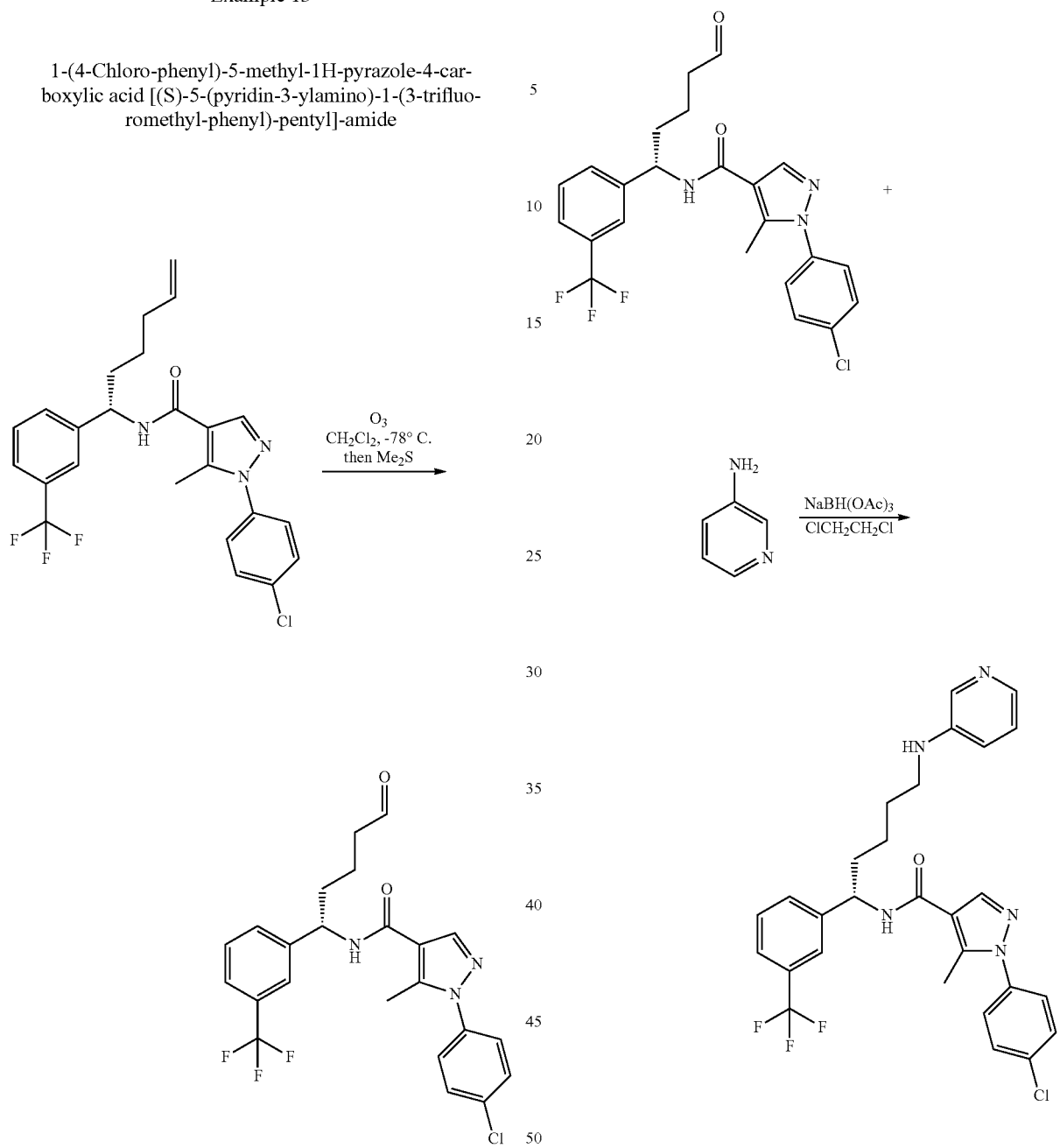

A solution of 1-(4-chloro-phenyl)-5-methyl-1H-pyrazole-4-carboxylic acid [(S)-1-(3-trifluoromethyl-phenyl)-hex-5-enyl]-amide (800 mg, 1.7 mmol) in $CH_2Cl_2$ (25 mL) at −78° C. is treated with ozone gas by bubbling for 30 min until a blue color is sustained. After stirring for an additional hour at −78° C., dimethylsulfide (10 mL) is added. The reaction mixture is warmed to room temperature and concentrated in vacuo to afford 1-(4-chloro-phenyl)-5-methyl-1H-pyrazole-4-carboxylic acid [(S)-5-oxo-1-(3-trifluoromethyl-phenyl)-pentyl]-amide which is used without further purification.

To a solution of (S)-5-{[1-(4-chloro-phenyl)-5-methyl-1H-pyrazole-4-carbonyl]-amino}-5-(3-trifluoromethyl-phenyl)-pentanionaldehyde (60 mg, 0.13 mmol) and 3-aminopyridine (40 mg, 0.43 mmol) in 1,2-dichloroethane (3 mL) is added sodium triacetoxyborohydride (50 mg, 0.24 mmol). After stiffing at room temperature for 16 hours, the reaction mixture is filtered with the aid of 5 mL of 1,2-dichloroethane and concentrated in vacuo. The crude material is purified by preparative reverse phase HPLC (eluted with 10 to 90% $CH_3CN/H_2O$ and 0.1% TFA as additive) to afford 1-(4-chloro-phenyl)-5-methyl-1H-pyrazole-4-carboxylic acid [(S)-5-(pyridin-3-ylamino)-1-(3-trifluoromethyl-phenyl)-pentyl]-amide (18 mg, 25%).

Example 14

5-Aminomethyl-1-(4-chloro-phenyl)-1H-pyrazole-4-carboxylic acid [(S)-1-(3-trifluoromethyl-phenyl)-butyl]-amide

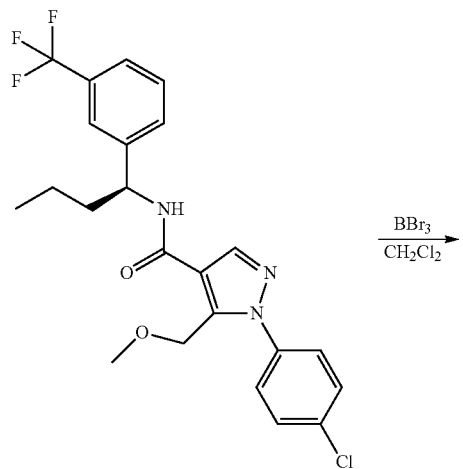

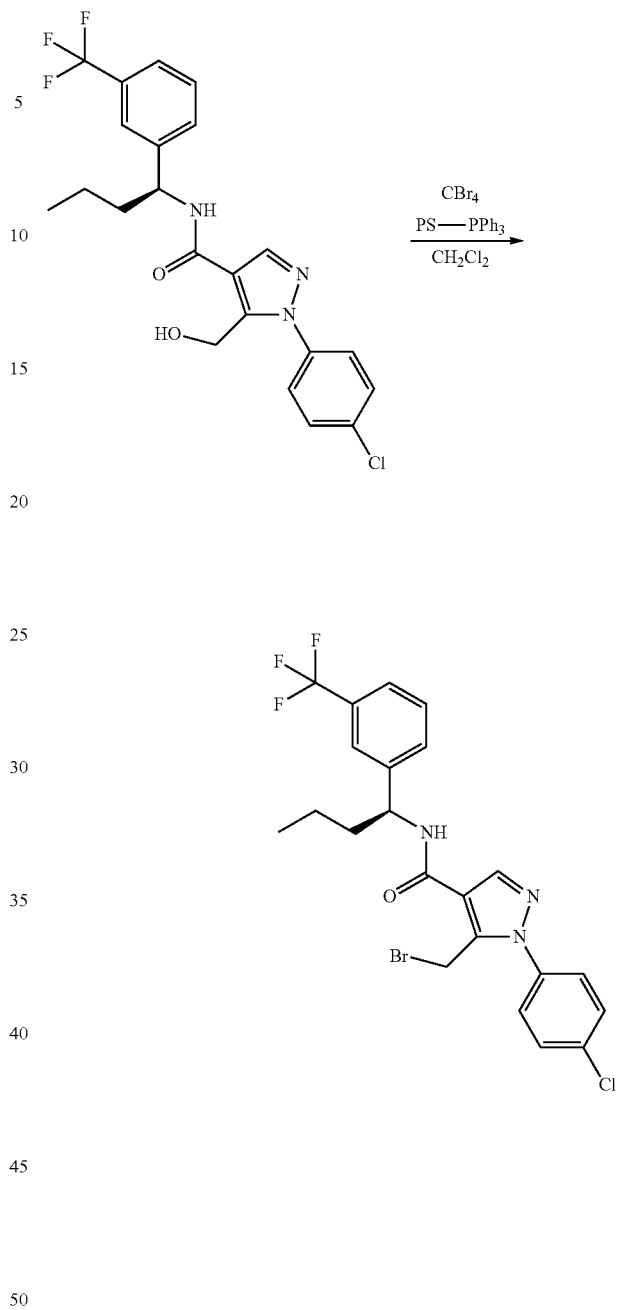

To a solution of 1-(4-chloro-phenyl)-5-methoxymethyl-1H-pyrazole-4-carboxylic acid [(S)-1-(3-trifluoromethyl-phenyl)-butyl]-amide (510 mg, 1.1 mmol) in CH$_2$Cl$_2$ (10 mL) is added BBr$_3$ (1.0 M in CH$_2$Cl$_2$, 1.6 mL, 1.6 mmol) dropwise. After stiffing at room temperature for 1 hour, the reaction mixture is quenched with methanol (25 mL) and concentrated in vacuo. The crude material is purified by flash chromatography on silica gel (eluted with 20 to 60% EtOAc/hexanes) to afford 1-(4-chloro-phenyl)-5-hydroxymethyl-1H-pyrazole-4-carboxylic acid [(S)-1-(3-trifluoromethyl-phenyl)-butyl]-amide (510 mg, >99%).

To a solution of 1-(4-chloro-phenyl)-5-hydroxymethyl-1H-pyrazole-4-carboxylic acid [(S)-1-(3-trifluoromethyl-phenyl)-butyl]-amide (500 mg, 1.1 mmol) in CH$_2$Cl$_2$ (10 mL) is added carbon tetrabromide (400 mg, 1.2 mmol) followed by polystyrene-bound triphenylphosphine (2.8 mmol). The reaction is stirred with an orbital shaker at room temperature for 16 hours. The resultant mixture is filtered and concentrated in vacuo. The crude 5-bromomethyl-1-(4-chloro-phenyl)-1H-pyrazole-4-carboxylic acid [(S)-1-(3-trifluoromethyl-phenyl)-butyl]-amide (490 mg, 86%) is used without further purification.

103

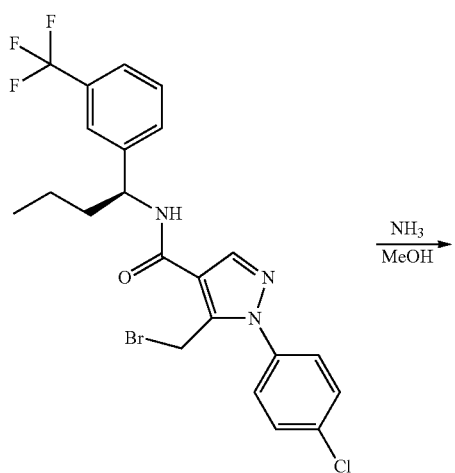

104

Example 15

5-Aminomethyl-1-(4-chloro-phenyl)-1H-pyrazole-4-carboxylic acid [(S)-1-(3-trifluoromethyl-phenyl)-butyl]-amide

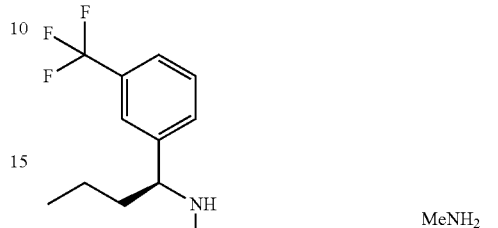

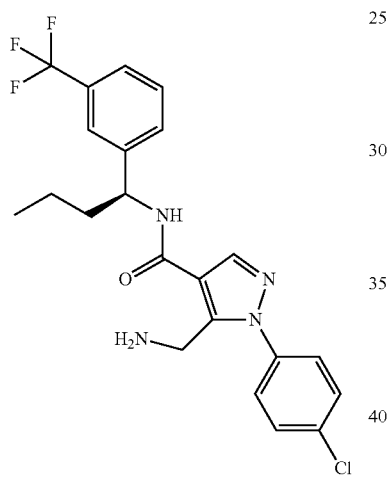

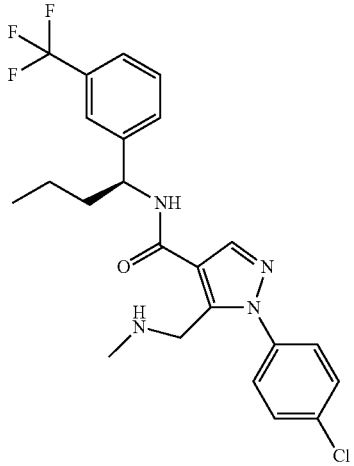

5-Bromomethyl-1-(4-chloro-phenyl)-1H-pyrazole-4-carboxylic acid [(S)-1-(3-trifluoromethyl-phenyl)-butyl]-amide (47 mg, 0.091 mmol) is treated with ammonia in methanol (7.0 N solution, 2.0 mL, 14 mmol) and the resultant solution is heated in a microwave at 120° C. for 3 min. The crude reaction mixture is concentrated in vacuo and purified by preparative reverse phase HPLC (eluted with 10 to 90% $CH_3CN/H_2O$ and 0.1% TFA as additive) to afford 5-aminomethyl-1-(4-chloro-phenyl)-1H-pyrazole-4-carboxylic acid [(S)-1-(3-trifluoromethyl-phenyl)-butyl]-amide (25 mg, 61%).

A solution of 5-bromomethyl-1-(4-chloro-phenyl)-1H-pyrazole-4-carboxylic acid [(S)-1-(3-trifluoromethyl-phenyl)-butyl]-amide (50 mg, 0.091 mmol) in DMF (2 mL) is treated with methylamine in THF (2.0 N solution, 49 µL, 0.091 mmol) and the resultant solution is heated in a microwave at 125° C. for 5 min. The crude reaction mixture is concentrated in vacuo and purified by preparative reverse phase HPLC (eluted with 10 to 90% $CH_3CN/H_2O$ and 0.1% TFA as additive) to afford 5-aminomethyl-1-(4-chloro-phenyl)-1H-pyrazole-4-carboxylic acid [(S)-1-(3-trifluoromethyl-phenyl)-butyl]-amide (20 mg, 44%).

Example 16

1-(4-Chloro-phenyl)-5-methyl-1H-pyrazole-4-carboxylic acid [1-(5-methanesulfonyl-pyridin-3-yl)-butyl]-amide

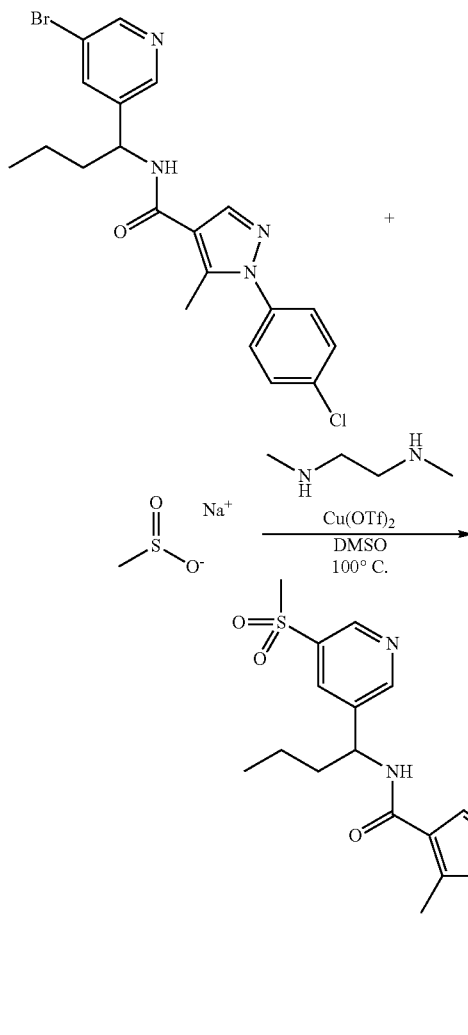

1-(4-Chloro-phenyl)-5-methyl-1H-pyrazole-4-carboxylic acid [1-(5-bromo-pyridin-3-yl)-butyl]-amide (100 mg, 0.22 mmol), copper(II) triflate (81 mg, 0.22 mmol), sodium methylsulfinate (80 mg, 0.67 mmol) are added to a reaction vial with a septum top which is then evacuated and filled with nitrogen for 3 cycles. DMSO (1 mL) and N,N'-dimethylethylenediamine (71 µL, 0.67 mmol) are added and the reaction is heated at 100° C. for 30 hours. The resultant mixture is cooled to room temperature, diluted with EtOAc (50 mL), and washed with saturated aqueous ammonium chloride (2×25 mL), saturated aqueous sodium bicarbonate (25 mL) and brine (25 mL). The combined organic layers are dried over magnesium sulfate, filtered and concentrated in vacuo. The crude material is purified by preparative reverse phase HPLC (eluted with 10 to 95% CH$_3$CN/H$_2$O and 0.1% TFA as additive) to afford 1-(4-chloro-phenyl)-5-methyl-1H-pyrazole-4-carboxylic acid [1-(5-methanesulfonyl-pyridin-3-yl)-butyl]-amide as a colorless foam (30 mg, 30%).

Example 17

1-(4-Chloro-phenyl)-5-methyl-1H-pyrazole-4-carboxylic acid (1-pyridin-3-yl-butyl)-amide and 3-[5-(1-{[1-(4-chloro-phenyl)-5-methyl-1H-pyrazole-4-carbonyl]-amino}-butyl)-pyridine-3-sulfonyl]-propionic acid methyl ester

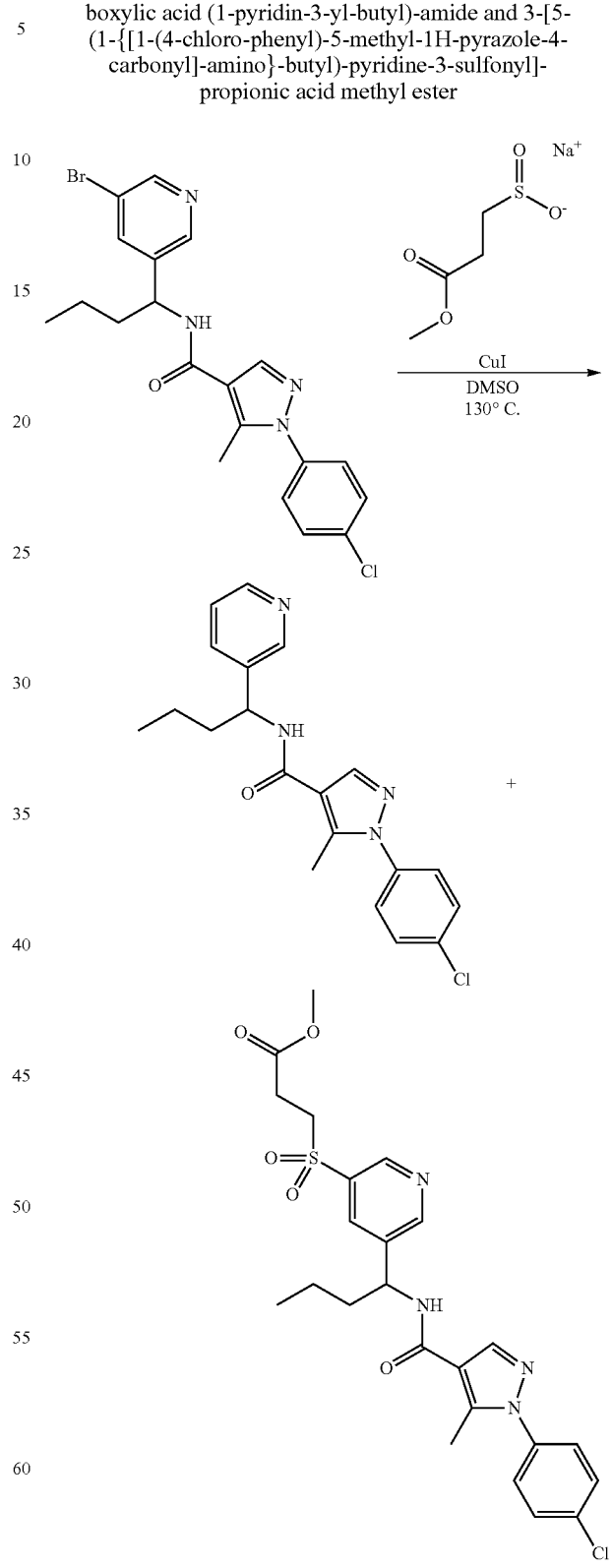

A solution of 1-(4-chloro-phenyl)-5-methyl-1H-pyrazole-4-carboxylic acid [1-(5-bromo-pyridin-3-yl)-butyl]-amide (1.1 g, 2.5 mmol), copper(I) iodide (1.4 g, 7.4 mmol), sodium 3-methoxy-3-oxopropane-1-sulfinate (1.3 g, 7.4 mmol) in DMSO (10 mL) is heated at 130° C. for 1.5 hour. After cooling to room temperature, saturated aqueous sodium ammonium chloride (10 mL) is added and the resultant mixture is stirred for 1 hour. The crude mixture is poured into saturated aqueous sodium bicarbonate (250 mL) and extracted with EtOAc (1×250 mL, 2×100 mL). The combined organic layers are washed with brine (100 mL), dried over sodium sulfate, filtered and concentrated in vacuo. Purification by flash chromatography on silica gel (eluted with 25 to 75% EtOAc/hexanes) affords 1-(4-chloro-phenyl)-5-methyl-1H-pyrazole-4-carboxylic acid (1-pyridin-3-yl-butyl)-amide (159 mg, 16%) and 3-[5-(1-{[1-(4-chloro-phenyl)-5-methyl-1H-pyrazole-4-carbonyl]-amino}-butyl)-pyridine-3-sulfonyl]-propionic acid methyl ester (540 mg, 42%).

Example 18

1-(4-Chloro-phenyl)-5-methyl-1H-pyrazole-4-carboxylic acid {1-[5-(3-hydroxy-propane-1-sulfonyl)-pyridin-3-yl]-butyl}-amide A solution of 3-[5-(1-{[1-(4-chloro-phenyl)-5-methyl-1H-pyrazole-4-carbonyl]-amino}-butyl)-pyridine-3-sulfonyl]-propionic acid methyl ester (51 mg, 0.10 mmol) in THF (2.5 mL) is treated lithium borohydride (13 mg, 0.59 mmol) and heated at 70° C. for 1 hour. After cooling to room temperature, the reaction is quenched by slow addition of 10 mL of water and extracted with EtOAc (2×25 mL). The combined organic layers are washed with brine (50 mL), dried over magnesium sulfate, filtered and concentrated in vacuo. Purification by flash chromatography on silica gel (eluted with 50 to 100% EtOAc/hexanes) followed by preparative reverse phase HPLC (eluted with 5 to 95% $CH_3CN/H_2O$ and 0.1% TFA as additive) affords 1-(4-chloro-phenyl)-5-methyl-1H-pyrazole-4-carboxylic acid {1-[5-(3-hydroxy-propane-1-sulfonyl)-pyridin-3-yl]-butyl}-amide (8.0 mg, 17%).

Example 19

1-(4-Chloro-phenyl)-5-methyl-1H-pyrazole-4-carboxylic acid [1-(5-methanesulfonylamino-pyridin-3-yl)-butyl]-amide

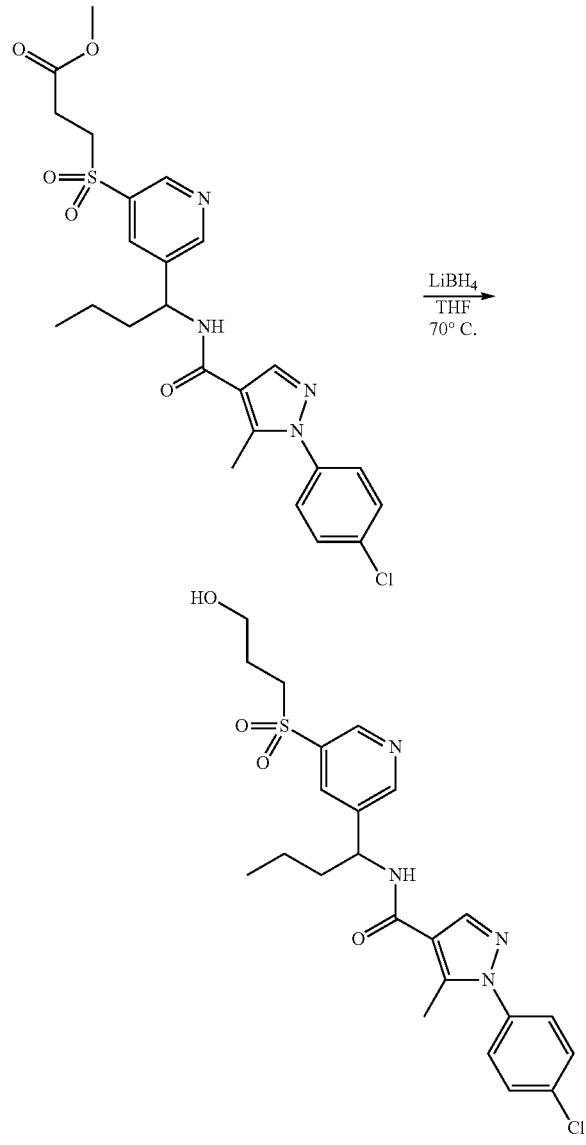

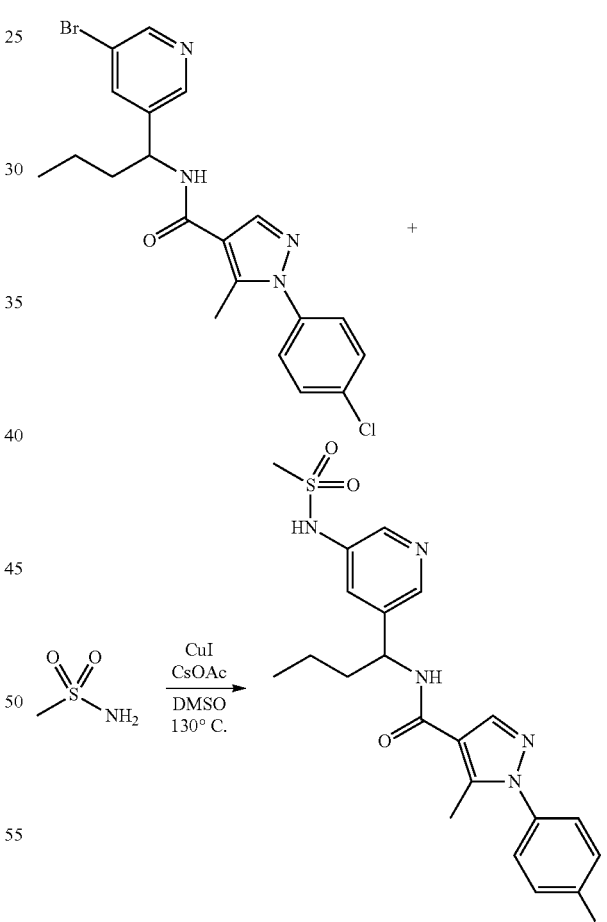

A solution of 1-(4-chloro-phenyl)-5-methyl-1H-pyrazole-4-carboxylic acid [1-(5-bromo-pyridin-3-yl)-butyl]-amide (100 mg, 0.22 mmol), methanesulfonamide (85 mg, 0.89 mmol), copper(I) iodide (210 mg, 1.1 mmol) and cesium acetate (260 mg, 1.3 mmol) in DMSO (3 mL) is heated at 130° C. for 18 hours. After cooling to room temperature, saturated aqueous sodium ammonium chloride (2 mL) and saturated aqueous sodium bicarbonate (1 mL) are added and the resultant mixture is stirred for 30 min. The crude mixture is diluted with EtOAc (50 mL) and washed with saturated aqueous sodium ammonium chloride (25 mL), saturated aqueous sodium bicarbonate (25 mL) and brine (25 mL). The combined organic layers are dried over magnesium sulfate, filtered and concentrated in vacuo. Purification by flash chromatography on silica gel (eluted with 0 to 6% MeOH/CH$_2$Cl$_2$) affords 1-(4-chloro-phenyl)-5-methyl-1H-pyrazole-4-carboxylic acid [1-(5-methanesulfonylamino-pyridin-3-yl)-butyl]-amide as an off-white solid (38 mg, 36%).

Example 20

1-(4-Chloro-phenyl)-5-methyl-1H-pyrazole-4-carboxylic acid [1-(2-methylsulfamoyl-pyridin-4-yl)-butyl]-amide

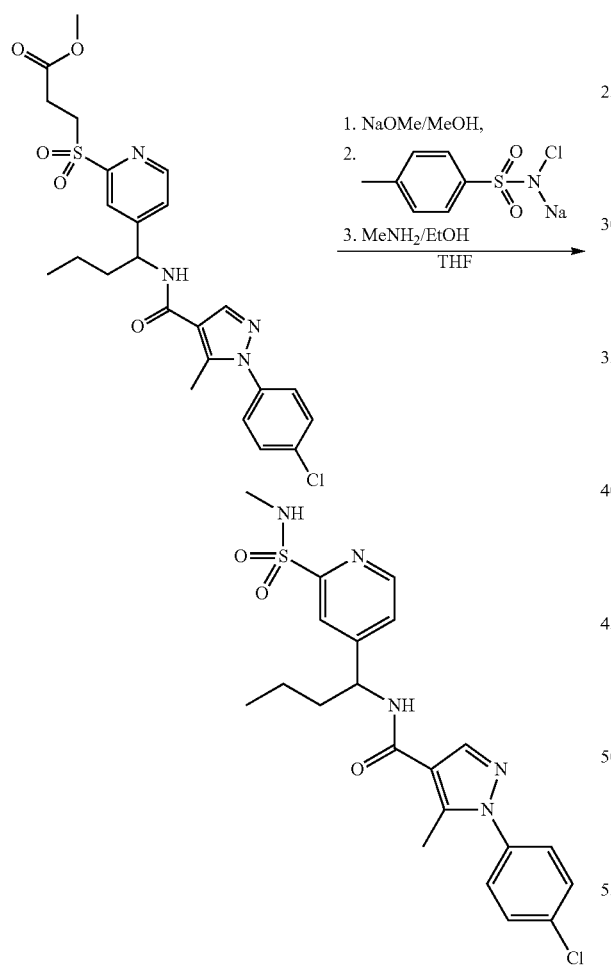

added and the concentration process is repeated. The resultant residue is dried under high vacuum for 5 min, dissolved in THF (10 mL) and treated with chloramine T (180 mg, 0.77 mmol). The reaction mixture is stirred at room temperature for 15 min and then treated with methyl amine in ethanol (33% solution in ethanol, 0.48 mL, 3.9 mmol) in one portion. After 20 min the reaction mixture is diluted with saturated aqueous sodium bicarbonate (20 mL) and water (8 mL), and extracted with EtOAc (2×35 mL). The combined organic layers are washed with brine (10 mL), dried over sodium sulfate, filtered and concentrated in vacuo. The residue is purified by preparative reverse phase HPLC (eluted with 10 to 90% CH$_3$CN/H$_2$O and 0.1% TFA as additive) to afford 1-(4-chloro-phenyl)-5-methyl-1H-pyrazole-4-carboxylic acid [1-(2-methylsulfamoyl-pyridin-4-yl)-butyl]-amide (160 mg, 90%).

Example 21

1-(4-Chloro-phenyl)-5-methyl-1H-pyrazole-4-carboxylic acid [1-(2-sulfamoyl-pyridin-4-yl)-butyl]-amide

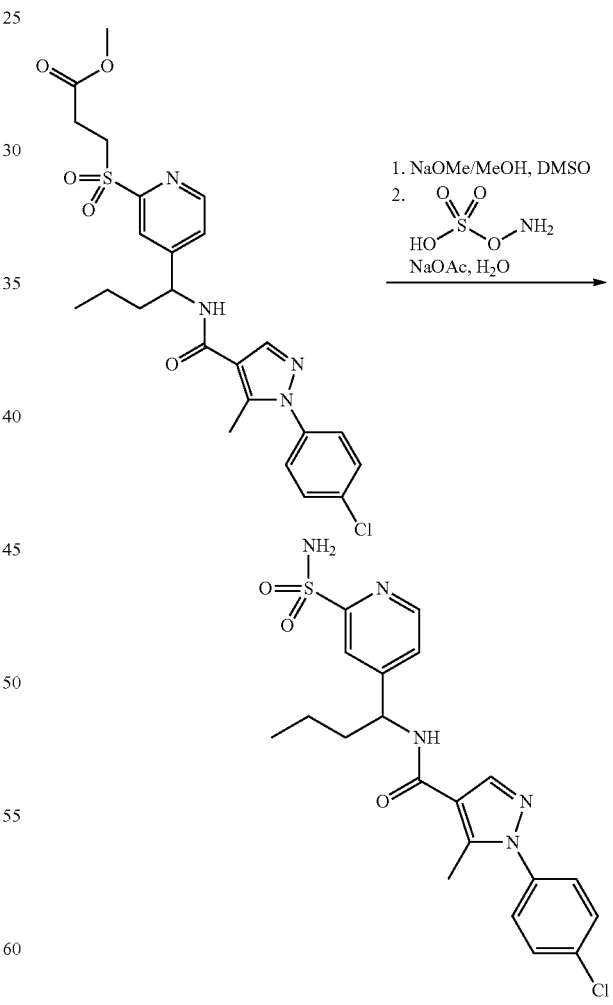

To a solution of 3-[4-(1-{[1-(4-chloro-phenyl)-5-methyl-1H-pyrazole-4-carbonyl]-amino}-butyl)-pyridine-2-sulfonyl]-propionic acid methyl ester (200 mg, 0.39 mmol) in anhydrous THF (10 mL) is added sodium methoxide in methanol (2.6 M solution freshly prepared by dissolving 140 mg of sodium in 2.4 mL of methanol, 0.15 mL, 0.39 mmol). After stirring at room temperature for 10 min, the reaction mixture is concentrated in vacuo. Anhydrous THF (10 mL) is To a solution of 3-[4-(1-{[1-(4-chloro-phenyl)-5-methyl-1H-pyrazole-4-carbonyl]-amino}-butyl)-pyridine-2-sulfonyl]-propionic acid methyl ester (60 mg, 0.12 mmol) in anhydrous DMSO (1.5 mL) is added sodium methoxide in methanol (2.7 M solution freshly prepared by dissolving 250 mg of sodium in 4.0 mL of methanol, 44 µL, 0.12 mmol). After stirring at room temperature for 15 min, the reaction mixture is cooled to 0° C. and treated with a solution of hydroxylamine-O-sulfonic acid (260 mg, 2.3 mmol) and sodium acetate (150 mg, 1.9 mmol) in water (6 mL). The resultant mixture is warmed to room temperature and stirred overnight for 18 hours. EtOAc (100 mL) is added and the phases are separated. The organic layer is washed with water (4×15 mL, until pH of water layer is ~5), dried over magnesium sulfate, filtered and concentrated in vacuo. The residue is purified by preparative reverse phase HPLC (eluted with 10 to 65% CH$_3$CN/H$_2$O and 0.1% TFA as additive) to afford 1-(4-chloro-phenyl)-5-methyl-1H-pyrazole-4-carboxylic acid [1-(2-sulfamoyl-pyridin-4-yl)-butyl]-amide (39 mg, 75%).

Example 22

1-(4-Chloro-phenyl)-5-methyl-1H-pyrazole-4-carboxylic acid {1-[6-(tetrahydro-pyran-4-ylsulfamoyl)-pyridin-3-yl]-butyl}-amide and 5-(1-{[1-(4-chlorophenyl)-5-methyl-1H-pyrazole-4-carbonyl]-amino}-butyl)-pyridine-2-sulfonic acid

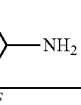
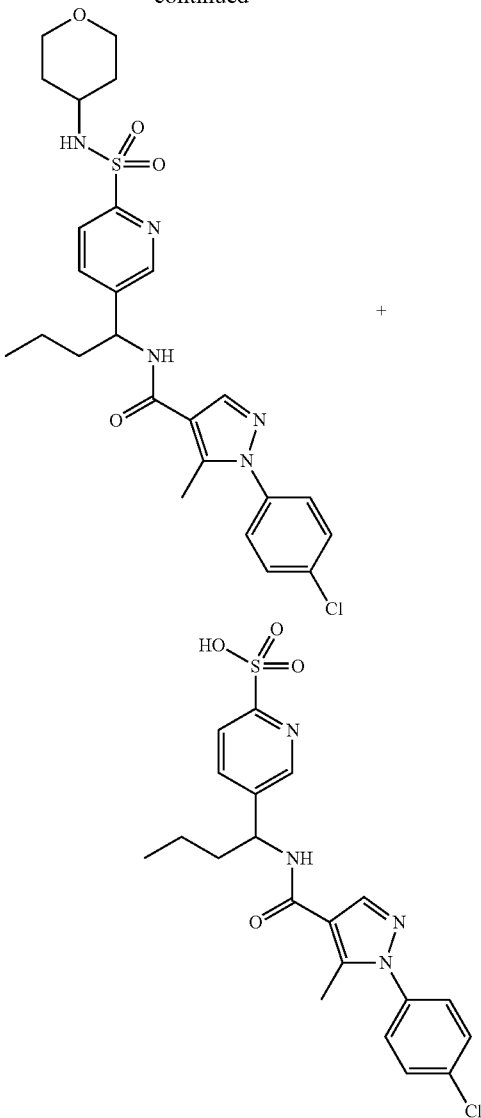

To a solution of 3-[5-(1-{[1-(4-chloro-phenyl)-5-methyl-1H-pyrazole-4-carbonyl]-amino}-butyl)-pyridine-2-sulfonyl]-propionic acid methyl ester (150 mg, 0.29 mmol) in anhydrous THF (15 mL) is added sodium methoxide in methanol (2.6 M solution freshly prepared by dissolving 120 mg of sodium in 2.0 mL of methanol, 0.12 mL, 0.32 mmol). After stirring at room temperature for 15 min, the reaction mixture is concentrated in vacuo. Anhydrous THF (10 mL) is added and the concentration process is repeated. The resultant residue is dried under high vacuum for 5 min, dissolved in THF (15 mL) and treated with N-chlorosuccinimide (77 mg, 0.58 mmol). The reaction mixture is stirred at room temperature for 15 min and then tetrahydro-pyran-4-ylamine (130 mg, 1.3 mmol) is added in one portion. After 20 min the reaction mixture is concentrated in vacuo and purified directly by preparative reverse phase HPLC (eluted with 10 to 90% CH$_3$CN/H$_2$O and 0.1% TFA as additive) followed preparative TLC (eluted with 70% EtOAc/hexanes) to afford 1-(4-chloro-phenyl)-5-methyl-1H-pyrazole-4-carboxylic acid {1-[6-(tetrahydro-pyran-4-ylsulfamoyl)-pyridin-3-yl]- butyl}-amide (14 mg, 9%) and 5-(1-{[1-(4-chloro-phenyl)-5-methyl-1H-pyrazole-4-carbonyl]-amino}-butyl)-pyridine-2-sulfonic acid (15 mg, 12%).

Example 23

1-(4-Chloro-phenyl)-5-methoxymethyl-1H-pyrazole-4-carboxylic acid methyl ester

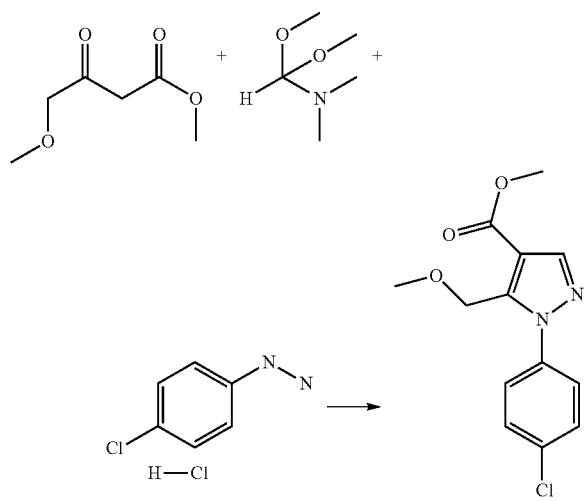

4-Methoxy-3-oxobutyric acid methyl ester (1.50 g, 10.3 mmol) was mixed with dimethylformamide dimethylacetal (1.83 g, 15.4 mmol) and a catalytic amount of para-toluene sulfonic acid and heated in the microwave for 15 min at 130° C. The mixture was cooled to room temp. and then concentrated in vacuo to afford a red oil. In a second flask para-chlorophenylhydrazine hydrochloride (1.84 g, 10.3 mmol) was placed in acetonitrile (10 mL) and then treated with the above red oil in triethylamine (6 mL). The mixture was stirred for 14 h, concentrated in vacuo and purified by silica chromatography (5% ethylacetate in hexanes) to afford 1-(4-Chloro-phenyl)-5-methoxymethyl-1H-pyrazole-4-carboxylic acid methyl ester (1.90 g, 66%).

Example 24

4-((S)-1-Amino-propyl)-pyridine-2-carboxylic acid amide

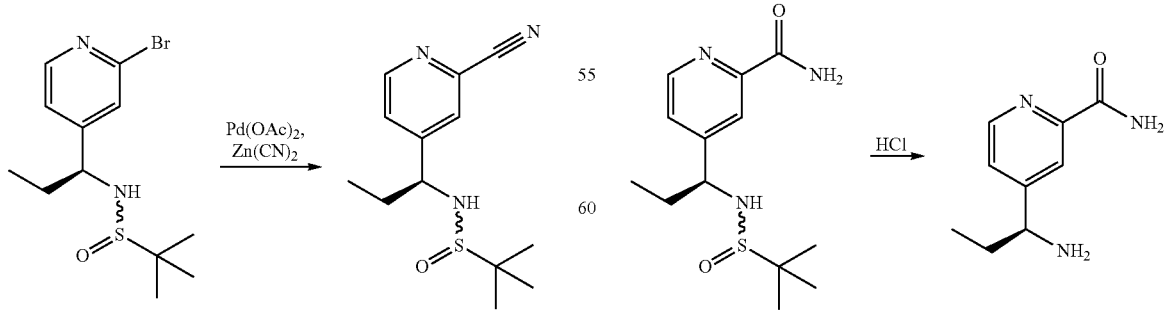

Triphenylphosphine (PS-resin bound, 287 mg) and palladium acetate (70 mg, 0.31 mmol) were combined in a pressure vial. Dimethylformamide (3 mL) was added. The vial was flushed with nitrogen and a septa was affixed. The mixture was stirred at room temp. for 1 h, then the septa was removed and zinc cyanide (367 mg, 3.13 mmol) was added, followed by 2-methylpropane 2-sulfinic acid [(S)-1-(2-bromo-pyridin-4-yl)-propyl]-amide (1.00 g, 3.13 mmol) in dimethylformamide (7 mL). The vial was again flushed with nitrogen and sealed. The reaction was allowed to heat at 140° C. in an oil bath for 1 h. The solids are filtered of using a glass frit and rinsed with diethylether. The filtrate was diluted with diethylether and extracted with water (2×40 mL) and with brine (40 mL). The organic phase was dried with sodium sulfate and concentrated. The residue was purified by prepHPLC (eluted with 15-85% acetonitrile in water, with 0.1% TFA). Fractions were concentrated to remove acetonitrile, basified by sat. sodium bicarbonate solution, extracted with ethyl acetate, washed with brine, dried over sodium sulfate, filtered, and concentrated to yield 2-methyl-propane-2-sulfinic acid [(S)-1-(2-cyano-pyridin-4-yl)-propyl]-amide as a colorless oil (460 mg, 55%).

To a rapidly stirred solution of 2-Methyl-propane-2-sulfinic acid [(S)-1-(2-cyano-pyridin-4-yl)-propyl]-amide (4.40 g, 16.6 mmol) in DMSO (70 mL) at 10° C. was added potassium carbonate (3.00 g, 21.7 mmol) portionwise and hydrogen peroxide (30 wt. % in water, 6.16 mL, 54.4 mmol) dropwise. The reaction was stirred at room temp. for 3.5 h. The reaction was cooled to 5° C., diluted with ethyl acetate (100 mL) and quenched with sodium thiosulfate solution (10% in water, 25 mL), stirred at 5° C. for 1 h. The organic phase was separated, the aqueous phase was extracted with ethyl acetate (4×100 mL), the combined organic extracts were washed with water (3×50 mL), brine, dried over sodium sulfate, filtered and concentrated to give 4-[(S)-1-(2-Methyl-propane-2-sulfinylamino)-propyl]-pyridine-2-carboxylic acid amide (5.50 g, 99%) as a thick oil.

To a solution of 4-[(S)-1-(2-Methyl-propane-2-sulfinylamino)-propyl]-pyridine-2-carboxylic acid amide (5.50 g) in methanol (50 mL) was added hydrochloric acid (4 N in dioxane, 4.3 mL, 17.3 mmol) and the mixture was stirred for 2 h. Additional hydrochloric acid (4 N in dioxane, 0.5 mL, 2.0 mmol) was added. The mixture was stirred for another 1.5 h. The mixture was concentrated to remove methanol and then diluted with ethyl acetate (400 mL), washed with sat. sodium bicarbonate solution, The aqueous layer was extracted with ethyl acetate (4×100 mL). the combined organic extracts were washed with brine, dried over sodium sulfate, filtered and concentrated to give 4-((S)-1-Amino-propyl)-pyridine-2-carboxylic acid amide (3.50 g, 100%)

Example 25

(S)-1-(2-Methanesulfonyl-thiazol-5-yl)-propylamine hydrochloride

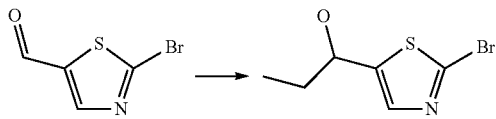

2-Bromo-thiazole-5-carbaldehyde (1.00 g, 5.21 mmol) was dissolved in THF (10 ml). A solution of ethylmagnesium bromide (3 M in diethylether, 5.00 mL, 15.0 mmol) was added. The mixture was stirred for 18 h. The reaction was poured into sat. ammonium chloride solution/ice (100 mL) and diluted with ethyl acetate (100 ml). The organic phase was separated, washed with sodium bicarbonate solution (100 mL), dried over sodium sulfate, filtered and concentrated. Purification by silica gel chromatography eluting with a gradient of 0-100% ethyl acetate in hexanes provided 1-(2-bromo-thiazol-5-yl)-propan-1-ol (480 mg, 42%). Unreacted 2-Bromo-thiazole-5-carbaldehyde (465 mg, 46%) was also obtained.

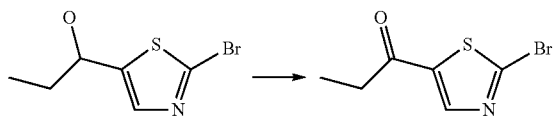

To a solution of 1-(2-Bromo-thiazol-5-yl)-propan-1-ol (175 mg, 0.79 mmol) in dichloromethane (10 mL) was added Dess-Martin periodinane (334 mg, 0.79 mmol). The reaction was stirred for 2 h, then diluted with dichloromethane (50 mL), washed with sat. sodium bicarbonate solution (50 mL) and brine (50 mL), dried over sodium sulfate, filtered and concentrated. Purification by silica gel chromatography eluting with a gradient of 0-100% ethyl acetate in hexanes gave 1-(2-bromo-thiazol-5-yl)-propan-1-one (75 mg, 43%).

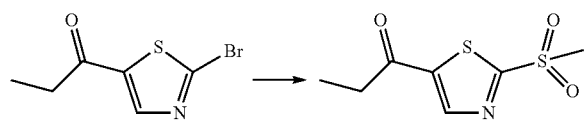

To a solution of 1-(2-bromo-thiazol-5-yl)-propan-1-one (75 mg, 0.34 mmol) in dimethyl sulfoxide (3 mL) was added the sodium methylsulfinate (41 mg, 0.34 mmol) followed by copper iodide (65 mg, 0.34 mmol). The mixture was heated in a microwave at 120° C. for 1 h. The reaction was diluted with ethyl acetate (20 mL) and washed with sat. sodium bicarbonate solution (120 ml) and brine (10 ml). The aqueous phase was extracted with ethyl acetate (2×10 mL). The combined organic extracts were dried over magnesium sulfate, filtered and concentrated to give 1-(2-methanesulfonyl-thiazol-5-yl)-propan-1-one (42 mg, 56%) that was used without further purification.

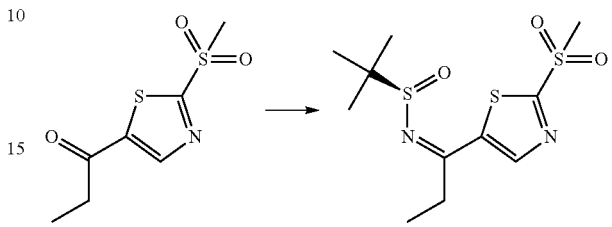

A mixture of crude 1-(2-methanesulfonyl-thiazol-5-yl)-propan-1-one (110 mg, 0.50 mmol), (R)-2-methyl-2-propanesulfinamide (70 mg, 0.55 mmol) and titanium isopropoxide (0.29 mL, 1.00 mmol) in tetrahydrofuran (10 mL) was warmed to reflux for 18 h. The mixture was cooled to room temperature and diluted with diethylether (100 mL) and water (6 mL). The mixture was stirred for 10 min and then dried over sodium sulfate, filtered and concentrated. The crude product was purified by silica gel chromatography, eluting with a gradient of 0-100% ethyl acetate in hexanes to give 2-methyl-propane-2-sulfinic acid [1-(2-methanesulfonyl-thiazol-5-yl)-prop-(Z)-ylidene]-amide (93 mg, 58%). Unreacted 1-(2-Methanesulfonyl-thiazol-5-yl)-propan-1-one (43 mg, 39%) was also isolated.

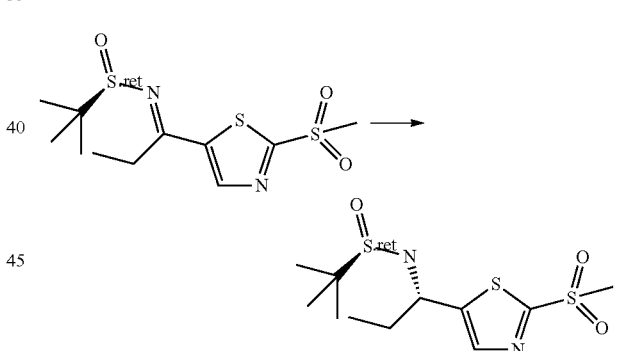

To a solution of 2-methyl-propane-2-sulfinic acid [1-(2-methanesulfonyl-thiazol-5-yl)-prop-(Z)-ylidene]-amide (93 mg, 0.29 mmol) in tetrahydrofuran (5 mL) was added L-selectride (1 M in THF, 0.58 mL, 0.58 mmol) dropwise at −78° C. The reaction was stirred for 2.5 h at −78° C. The reaction mixture was quenched with sat. ammonium chloride solution (100 mL), and the layers were separated. The aqueous layer was extracted with ethyl acetate (2×10 ml). The organic layers were combined, washed with brine (10 ml), dried over sodium sulfate, filtered and concentrated. The residue was purified by silica gel chromatography eluting with a gradient of 0-100% ethyl acetate in hexanes to yield 2-methyl-propane-2-sulfinic acid [(S)-1-(2-methanesulfonyl-thiazol-5-yl)-propyl]-amide (80 mg, 86%) as an oil. Major diastereomer was 96.4% de by HPLC.

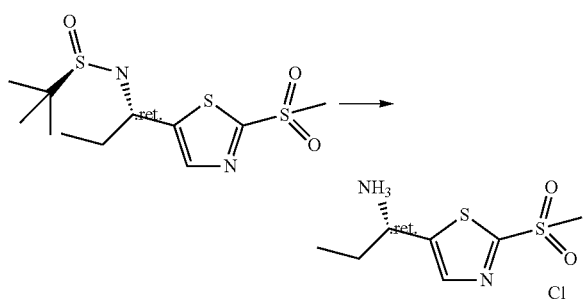

A solution of 2-methyl-propane-2-sulfinic acid [(S)-1-(2-methanesulfonyl-thiazol-5-yl)-propyl]-amide (80 mg, 0.25 mmol) in methanol (5 mL) was treated with hydrochloric acid (4 N in dioxane, 1 mL, 4 mmol). The mixture was stirred at room temp. for 1 h and then concentrated. The residue was taken up in dichloromethane (2 mL) and diluted with hexanes (10 mL). Concentration gave (S)-1-(2-Methanesulfonyl-thiazol-5-yl)-propylamine hydrochloride (62 mg, 98%) as a yellow hygroscopic solid, that was used without further purification.

Assessment of Biological Properties

Compounds are assessed for the ability to block the interaction of CCR1 and its ligands in a functional cellular assay measuring calcium flux in response to MIP1α in CCR1-transfected cells.

Method A: Non-adherent cells purchased from Chemicon Corporation (HTS005C), stably expressing recombinant CCR1 and G-alpha-16 are grown in RPMI 1640 medium (Mediatech 10-080-CM) supplemented with 10% heat-inactivated FBS, 0.4 mg/mL Geneticin and penicillin/streptomycin. On the day of the assay, the cells are transferred to a beaker and dye-loaded in bulk using a Fluo-4 NW Calcium Assay Kit with probenecid (Invitrogen F36205) at 0.8E6 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 3-fold with 10 doses total). The final concentration of DMSO is 1%. The buffer is HBSS (Invitrogen 14025) with 20 mM HEPES at pH 7.4. The cells are allowed to incubate 1 hour in the dark at room temperature. The plates are transferred to the FLIPR TETRA where MIP-1alpha in 1% BSA is added at the EC80 final concentration. Wells +/−MIP-1alpha containing diluted DMSO instead of compound serve as the controls. Intracellular calcium flux is recorded on the FLIPR TETRA, using excitation at 470/495 nm and emission at 515/575 nm. Data are analyzed using Activity Base software.

Method B: Non-adherent cells purchased from Chemicon Corporation (HTS005C), stably expressing recombinant CCR1 and G-alpha-16 are grown in RPMI 1640 medium (Mediatech 10-080-CM) supplemented with 10% FBS, 0.4 mg/mL Geneticin and penicillin/streptomycin. On the day of the assay, the cells are loaded with Calcium 4 dye (Molecular Devices R7448) with Probenecid (Invitrogen P346400) at 8E5 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells incubate 30 minutes at 37 C and then 30 minutes at room temperature. The plates are transferred to the HAMAMATSU FDSS6000 where MIP-1alpha in 1% BSA is added at the EC80 final concentration. All plates must be read within 4 hours of the start of dye-loading. Wells +/−MIP-1alpha containing diluted DMSO instead of compound serve as the controls. Data are analyzed using Activity Base software.

Representative compounds of the invention have been tested in one of the aforementioned assays and have shown activity as CCR1 antagonists. Preferred compounds will have $IC_{50}$'s of less than 100 nM. The following are examples of preferred compounds:

TABLE II

| Name | Method A or Method B IC50 (nM) |
|---|---|
| 1-(4-Bromo-phenyl)-5-methyl-1H-pyrazole-4-carboxylic acid [1-(5-methanesulfonyl-pyridin-3-yl)-butyl]-amide | 9.3 |
| 1-(3-Chloro-4-fluoro-phenyl)-5-methyl-1H-pyrazole-4-carboxylic acid [1-(5-methanesulfonyl-pyridin-3-yl)-butyl]-amide | 5.9 |
| 1-(3-Chloro-4-fluoro-phenyl)-5-methyl-1H-pyrazole-4-carboxylic acid [1-(6-methanesulfonyl-pyridin-3-yl)-butyl]-amide | 71 |
| 1-(3,4-Dichloro-phenyl)-5-methyl-1H-pyrazole-4-carboxylic acid ((S)-1-naphthalen-1-yl-ethyl)-amide | 54 |
| 1-(3,4-Dichloro-phenyl)-5-methyl-1H-pyrazole-4-carboxylic acid [(S)-1-(3-bromo-phenyl)-propyl]-amide | 16 |
| 1-(3,4-Dichloro-phenyl)-5-methyl-1H-pyrazole-4-carboxylic acid [(S)-1-(4-fluoro-3-trifluoromethyl-phenyl)-ethyl]-amide | 28 |
| 1-(4-Chloro-phenyl)-5-methyl-1H-pyrazole-4-carboxylic acid [(S)-1-(4-fluoro-3-trifluoromethyl-phenyl)-propyl]-amide | 13 |
| 1-(4-Chloro-phenyl)-5-methyl-1H-pyrazole-4-carboxylic acid [(S)-1-(4-fluoro-3-trifluoromethyl-phenyl)-butyl]-amide | 10 |
| 1-(4-Chloro-phenyl)-5-methyl-1H-pyrazole-4-carboxylic acid [(S)-1-(3-bromo-phenyl)-butyl]-amide | 28 |
| 1-(3,4-Dichloro-phenyl)-5-methyl-1H-pyrazole-4-carboxylic acid [(S)-1-(3-bromo-phenyl)-pent-4-enyl]-amide | 41 |
| 1-(4-Chloro-phenyl)-5-hydroxymethyl-1H-pyrazole-4-carboxylic acid [(S)-1-(3-bromo-phenyl)-butyl]-amide | 16 |
| 1-(4-Chloro-phenyl)-5-hydroxymethyl-1H-pyrazole-4-carboxylic acid [(S)-1-(3-trifluoromethyl-phenyl)-butyl]-amide | 6.5 |
| 1-(4-Chloro-phenyl)-5-methyl-1H-pyrazole-4-carboxylic acid [(S)-1-(3-trifluoromethyl-phenyl)-hex-5-enyl]-amide | 30 |

TABLE II-continued

| Name | Method A or Method B IC50 (nM) |
|---|---|
| 5-Aminomethyl-1-(4-chloro-phenyl)-1H-pyrazole-4-carboxylic acid [(S)-1-(3-trifluoromethyl-phenyl)-butyl]-amide | 12 |
| 1-(4-Chloro-phenyl)-5-methylaminomethyl-1H-pyrazole-4-carboxylic acid [(S)-1-(3-trifluoromethyl-phenyl)-butyl]-amide | 98 |
| 1-(4-Chloro-phenyl)-5-methyl-1H-pyrazole-4-carboxylic acid [1-(6-methanesulfonyl-pyridin-3-yl)-butyl]-amide | 35 |
| 1-(4-Chloro-phenyl)-5-methyl-1H-pyrazole-4-carboxylic acid [1-(5-bromo-pyridin-3-yl)-butyl]-amide | 4.1 |
| 1-(4-Chloro-phenyl)-5-methyl-1H-pyrazole-4-carboxylic acid [1-(5-ethanesulfonyl-pyridin-3-yl)-butyl]-amide | 94 |
| 1-(4-Chloro-phenyl)-5-methyl-1H-pyrazole-4-carboxylic acid [1-(5-methanesulfonyl-pyridin-3-yl)-butyl]-amide | 15 |
| 1-(4-Chloro-phenyl)-5-methyl-1H-pyrazole-4-carboxylic acid [1-(6-ethanesulfonyl-pyridin-3-yl)-butyl]-amide | 60 |
| 1-(4-Chloro-phenyl)-5-methyl-1H-pyrazole-4-carboxylic acid {1-[5-(propane-2-sulfonyl)-pyridin-3-yl]-butyl}-amide | 72 |
| 1-(4-Chloro-phenyl)-5-methyl-1H-pyrazole-4-carboxylic acid [1-(6-cyclopropanesulfonyl-pyridin-3-yl)-butyl]-amide | 53 |
| 1-(4-Chloro-phenyl)-5-methyl-1H-pyrazole-4-carboxylic acid [1-(5-cyclopropanesulfonyl-pyridin-3-yl)-butyl]-amide | 85 |
| 1-(4-Chloro-phenyl)-5-methyl-1H-pyrazole-4-carboxylic acid {1-[6-(3-hydroxy-propane-1-sulfonyl)-pyridin-3-yl]-butyl}-amide | 86 |
| 1-(3,4-Dichloro-phenyl)-5-methyl-1H-pyrazole-4-carboxylic acid [1-(6-methanesulfonyl-pyridin-3-yl)-butyl]-amide | 5.3 |
| 1-(4-Chloro-phenyl)-5-methyl-1H-pyrazole-4-carboxylic acid [1-(2-bromo-pyridin-4-yl)-butyl]-amide | 1.1 |
| 1-(4-Chloro-phenyl)-5-methyl-1H-pyrazole-4-carboxylic acid [1-(2-methanesulfonyl-pyridin-4-yl)-butyl]-amide | 2.3 |
| 1-(4-Chloro-phenyl)-5-methyl-1H-pyrazole-4-carboxylic acid {1-[6-(tetrahydro-pyran-4-ylsulfamoyl)-pyridin-3-yl]-butyl}-amide | 41 |
| 1-(4-Chloro-phenyl)-5-methyl-1H-pyrazole-4-carboxylic acid [1-(5-methylsulfamoyl-pyridin-3-yl)-butyl]-amide | 4.1 |
| 1-(4-Chloro-phenyl)-5-methyl-1H-pyrazole-4-carboxylic acid [1-(5-dimethylsulfamoyl-pyridin-3-yl)-butyl]-amide | 4.9 |
| 1-(4-Chloro-phenyl)-5-methyl-1H-pyrazole-4-carboxylic acid [1-(2-methylsulfamoyl-pyridin-4-yl)-butyl]-amide | 2.9 |
| 3-[4-(1-{[1-(4-Chloro-phenyl)-5-methyl-1H-pyrazole-4-carbonyl]-amino}-butyl)-pyridine-2-sulfonyl]-propionic acid methyl ester | 80 |
| 1-(4-Chloro-phenyl)-5-methyl-1H-pyrazole-4-carboxylic acid [1-(5-sulfamoyl-pyridin-3-yl)-butyl]-amide | 31 |
| 1-(4-Chloro-phenyl)-5-methyl-1H-pyrazole-4-carboxylic acid [1-(6-methylsulfamoyl-pyridin-3-yl)-butyl]-amide | 6.3 |
| 1-(4-Chloro-phenyl)-5-methyl-1H-pyrazole-4-carboxylic acid [1-(6-dimethylsulfamoyl-pyridin-3-yl)-butyl]-amide | 12 |
| 1-(4-Chloro-phenyl)-5-methyl-1H-pyrazole-4-carboxylic acid [1-(2-ethanesulfonyl-pyridin-4-yl)-butyl]-amide | 5.7 |
| 1-(4-Chloro-phenyl)-5-methyl-1H-pyrazole-4-carboxylic acid [1-(2-dimethylsulfamoyl-pyridin-4-yl)-butyl]-amide | 4.5 |
| 1-(4-Chloro-phenyl)-5-methyl-1H-pyrazole-4-carboxylic acid [1-(2-cyclopropanesulfonyl-pyridin-4-yl)-butyl]-amide | 12 |
| 1-(3,4-Dichloro-phenyl)-5-methyl-1H-pyrazole-4-carboxylic acid [1-(2-bromo-pyridin-4-yl)-butyl]-amide | 0.6 |
| 1-(3,4-Dichloro-phenyl)-5-methyl-1H-pyrazole-4-carboxylic acid [1-(2-methanesulfonyl-pyridin-4-yl)-butyl]-amide | 0.3 |
| 1-(3,4-Dichloro-phenyl)-5-methyl-1H-pyrazole-4-carboxylic acid [1-(5-methanesulfonyl-pyridin-3-yl)-butyl]-amide | 1.0 |
| 1-(4-Chloro-phenyl)-5-methyl-1H-pyrazole-4-carboxylic acid [1-(2-sulfamoyl-pyridin-4-yl)-butyl]-amide | 51 |
| 1-(4-Chloro-3-fluoro-phenyl)-5-methyl-1H-pyrazole-4-carboxylic acid [1-(5-methanesulfonyl-pyridin-3-yl)-butyl]-amide | 37 |
| 1-(4-Chloro-phenyl)-5-methyl-1H-pyrazole-4-carboxylic acid [1-(5-sulfamoyl-pyridin-3-yl)-butyl]-amide | 35 |
| 1-(4-Chloro-3-fluoro-phenyl)-5-methyl-1H-pyrazole-4-carboxylic acid [1-(6-methanesulfonyl-pyridin-3-yl)-butyl]-amide | 91 |
| 1-(4-Chloro-phenyl)-5-methyl-1H-pyrazole-4-carboxylic acid [(S)-1-(5-bromo-pyridin-3-yl)-propyl]-amide | 20 |
| 1-(4-Chloro-phenyl)-5-methyl-1H-pyrazole-4-carboxylic acid {1-[6-(2-hydroxy-ethylsulfamoyl)-pyridin-3-yl]-butyl}-amide | 97 |
| 1-(4-Chloro-phenyl)-5-methyl-1H-pyrazole-4-carboxylic acid [(S)-1-(2-methanesulfonyl-pyridin-4-yl)-propyl]-amide | 29 |
| 1-(4-Chloro-phenyl)-5-methyl-1H-pyrazole-4-carboxylic acid [(S)-1-(2-methylsulfamoyl-pyridin-4-yl)-propyl]-amide | 19 |
| 1-(4-Chloro-phenyl)-5-methyl-1H-pyrazole-4-carboxylic acid [(S)-1-(2-methanesulfonyl-thiazol-5-yl)-propyl]-amide | 57 |

Methods of Therapeutic Use

The compounds of the invention are effective antagonists of the interactions between CCR1 and its chemokine ligands and thus antagonize CCR1-mediated activity. Therefore, in one embodiment of the invention, there is provided methods of treating autoimmune disorders using compounds of the invention. In another embodiment, there is provided methods of treating inflammatory disorders using compounds of the invention.

Without wishing to be bound by theory, by antagonizing the interactions between CCR1 and its chemokine ligands, the compounds block chemotaxis of pro-inflammatory cells including monocytes, macrophages dendritic cells, eosinophils, and T cells (TH1) cells and other CCR1 positive cells to inflamed tissues and thereby ameliorate the chronic inflammation associated with autoimmune diseases. Thus, the antagonism of CCR1 activity is an attractive means for preventing and treating a variety of autoimmune disorders, including inflammatory diseases, autoimmune diseases, organ (Horuk et al. (2001) JBC 276 p. 4199) and bone marrow transplant rejection and other disorders associated with an influx of pro-inflammatory cells. For example, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection), Alzheimer's disease (Halks-Miller et al. (2003) Ann Neurol 54 p. 638), Asthma (Jouber et al. (2008) J. Immun 180 p. 1268) chronic kidney disease (Topham et al. (1999) J. Clin. Invest. 104 p. 1549), sepsis (He et al. (2007) Am J. Physio 292 p. G1173), autoimmune myocarditis (Futamats et al. (2006) J Mol Cell Cardiology 40 p. 853) and systemic lupus erythematosus. In particular, the compounds may be used to prevent or treat rheumatoid arthritis and multiple sclerosis. Other disorders associated with the trafficking of pro-inflammatory cells will be evident to those of ordinary skill in the art and can also be treated with the compounds and compositions of this invention.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A compound of the formula (I)

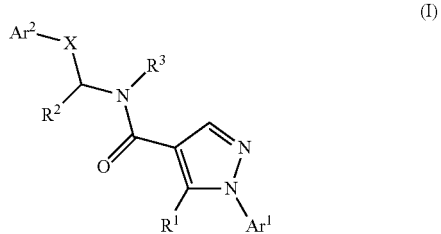

wherein
$Ar^1$ is phenyl, naphthyl or pyridyl each optionally substituted by one to three $R^a$;
X is —$(CH_2)_n$—;
$Ar^2$ is phenyl, naphthyl or pyridyl each optionally substituted by one to three $R^b$;
$R^1$ is hydrogen or $R^a$, with the proviso that $R^1$ is not aryl, $CF_3$ or n-Pr;
$R^2$ is $C_{1-6}$ alkyl, $C_{2-6}$alkenyl or $C_{3-6}$cycloalkyl, each optionally substituted by $R^a$;
$R^3$ is hydrogen, $C_{1-6}$ alkyl or $C_{1-6}$alkoxy$C_{1-6}$alkyl;
$R^a$ is $C_{1-6}$ alkyl, $C_{1-6}$alkenyl, $C_{3-10}$ cycloalkyl, $C_{1-6}$ alkoxy$C_{1-6}$alkyl, $C_{1-6}$ alkylthio, $C_{1-6}$ alkylsulfonyl, $C_{1-6}$ alkoxycarbonyl, hydroxyC$_{1-6}$alkyl, amino, mono-or di-C$_{1-6}$ alkylamino, aminoC$_{1-6}$alkyl, mono-or di-C$_{1-6}$ alkylaminoC$_{1-6}$alkyl, C$_{3-6}$ cycloalkylamino, C$_{1-6}$ alkylaminocarbonyl, C$_{1-6}$ acyl, C$_{1-6}$ acylamino, C$_{1-6}$ dialkylaminocarbonyl, hydroxyl, halogen, cyano, nitro, oxo, R$^4$—S(O)$_m$—NH—, R$^4$—NH—S(O)$_m$—, aryl, carboxyl, aryl (CH$_2$)$_{0-1}$amino, heteroaryl(CH$_2$)$_{0-1}$amino or heterocyclylcarbonyl wherein said heterocycle is optionally substituted with C$_{1-6}$alkyl, each substituent on R$^a$ where possible is optionally halogenated;

R$^b$ is hydroxyl, carboxyl, halogen, —(CH$_2$)$_n$—CN, nitro, oxo, C$_{1-6}$ alkyl, C$_{2-6}$ alkenyl, C$_{2-6}$ alkynyl, C$_{3-10}$ cycloalkyl, C$_{1-6}$ alkoxy, C$_{1-6}$ alkoxycarbonyl, —(CH$_2$)$_n$—NR$^c$R$^d$, R$_4$—S(O)$_m$—, R$^4$—S(O)$_m$—NR$^e$—, R$^4$—NR$^e$—S(O)$_m$—, —NR$^f$—C(O)—R$^e$, —(CH$_2$)$_x$—C(O)—(CH$_2$)$_n$—NR$^c$R$^d$, heterocyclyl, aryl or heteroaryl, each substituent on R$_b$ where possible is optionally halogenated or substituted with 1 to 3 C$_{1-6}$ alkyl, C$_{1-6}$ acyl, C$_{1-6}$ alkoxycarbonyl, C$_{1-6}$ alkyl-S(O)$_m$—, aryl or carboxyl;

each R$^c$, R$^d$ are independently hydrogen, C$_{1-6}$ alkyl, C$_{1-6}$ acyl, C$_{3-10}$ cycloalkyl, C$_{1-6}$ alkoxy, hydroxyC$_{1-6}$ alkyl, C$_{1-6}$ alkylC$_{1-6}$ alkoxy, C$_{1-6}$ alkylsulfonyl, C$_{1-6}$ alkoxycarbonyl or —(CH$_2$)$_n$—NR$^e$R$^f$;

each R$^e$, R$^f$ are independently hydrogen, C$_{1-6}$ alkyl, C$_{3-10}$ cycloalkyl, C$_{1-6}$ alkoxy, hydroxyC$_{1-6}$ alkyl or C$_{1-6}$ acyl;

R$^4$ is hydrogen, C$_{1-6}$ alkyl, C$_{3-10}$ cycloalkyl, heterocyclyl, aryl or heteroaryl each optionally substituted with C$_{1-6}$ alkyl, C$_{1-6}$ alkoxy, halogen, hydroxyl, amino, mono-or di-C$_{1-6}$ alkylamino, C$_{1-6}$ alkoxycarbonyl or C$_{1-6}$ acylamino;

each n, x are independently 0-3;

each m is independently 0-2;

or a pharmaceutically acceptable salt thereof.

2. The compound according to claim 1 wherein:

Ar$^1$ is phenyl optionally substituted by one to three groups selected from C$_{1-6}$alkyl, halogen and C$_{1-6}$alkylSO$_2$—;

X is —(CH$_2$)$_n$—;

Ar$_2$ is phenyl, naphthyl or pyridyl each optionally substituted by one to three R$^b$;

R$^1$ is C$_{1-2}$alkyl, C$_{1-2}$alkoxyC$_{1-2}$alkyl, hydroxyC$_{1-2}$alkyl, aminoC$_{1-2}$alkyl or mono-or di-C$_{1-3}$ alkylaminoC$_{1-2}$ alkyl;

R$^2$ is C$_{1-6}$ alkyl, C$_{2-6}$alkenyl, C$_{3-6}$cycloalkyl, C$_{1-6}$ alkoxycarbonylmethyl, hydroxyC$_{2-4}$alkyl, C$_{1-6}$ alkylaminocarbonylmethyl, C$_{1-6}$ dialkylaminocarbonylmethyl, 4-methylpiperidin-1-ylcarbonylC$_{2-4}$alkyl, phenyl(CH$_2$)$_{0-1}$ alkylaminoC$_{4-5}$alkyl or pyridyl(CH$_2$)$_{0-1}$alkylaminoC$_{4-5}$ alkyl;

R$^3$ is hydrogen;

R$^b$ is hydroxyl, halogen, CF$_3$, C$_{1-6}$ alkyl, C$_{1-6}$ alkoxy, R$^4$—S(O)$_m$—, R$^4$—S(O)$_m$—NR$^e$—, R$^4$—NR$^e$—S(O)$_m$—, —NR$^f$—C(O)—R$^e$ or —C(O)—NR$^c$R$^d$;

each R$^c$, R$^d$, R$^e$, R$^f$ are independently hydrogen, C$_{1-6}$ alkyl, C$_{3-10}$ cycloalkyl, hydroxyC$_{1-6}$ alkyl or C$_{1-6}$ acyl;

R$^4$ is hydrogen, tertrahydropyranyl or C$_{1-6}$ alkyl optionally substituted with C$_{1-6}$ alkoxy, C$_{3-6}$ cycloalkyl, halogen, hydroxyl, amino, mono-or di-C$_{1-6}$ alkylamino, C$_{1-6}$ alkoxycarbonyl or C$_{1-6}$ acylamino;

n is 0-1;

each m is independently 0-2.

3. The compound according to claim 2 wherein:

Ar$^1$ is phenyl optionally substituted by one to three groups selected from methyl, Br, Cl, F, and C$_{1-3}$alkylSO$_2$—;

X is a bond;

Ar$^2$ is phenyl, naphthyl or pyridyl each optionally substituted by one to three R$^b$;

R$^1$ is —CH$_3$, —CH$_2$OH, —CH$_2$NH$_2$ or —CH$_2$NHCH$_3$;

R$^2$ is C$_{1-3}$ alkyl, C$_{2-6}$alkenyl, cyclopropyl, C$_{1-3}$ alkoxycarbonylmethyl, hydroxyC$_{2-4}$alkyl, C$_{1-3}$alkylaminocarbonylmethyl, C$_{1-3}$dialkylaminocarbonylmethyl, 4-methylpiperidin-1-ylcarbonylC$_{2-4}$alkyl, phenyl(CH$_2$)$_{0-1}$ alkylaminoC$_{4-5}$alkyl or pyridyl(CH$_2$)$_{0-1}$alkylaminoC$_{4-5}$ alkyl;

R$^3$ is hydrogen;

R$^b$ is Br, Cl, F, CF$_3$, C$_{1-6}$ alkyl, C$_{1-6}$ alkoxy, —NHSO$_2$C$_{1-3}$ alkyl, —SO$_2$C$_{1-3}$alkyl, —SO$_2$(CH$_2$)$_{1-3}$OH, —SO$_2$(CH$_2$)$_{1-3}$CO$_2$C$_{1-3}$alkyl, —SO$_2$NH$_2$, —SO$_2$NHC$_{1-3}$ alkyl, —SO$_2$N(diC$_{1-3}$alkyl), —SO$_2$NH(tetrahydropyran-4-yl) or —SO$_2$NH(CH$_2$)$_{2-3}$OH.

4. The compound according to claim 3 wherein:

Ar$^1$ is phenyl optionally substituted by one to three groups selected from methyl, Br, Cl, F, and CH$_3$SO$_2$—;

X is a bond;

Ar$^2$ is phenyl or pyridyl each optionally substituted by one to three R$^b$;

R$^1$ is —CH$_3$;

R$^2$ is methyl, ethyl or n-propyl;

R$^3$ is hydrogen;

R$^b$ is Br, Cl, F, CF$_3$, —NHSO$_2$C$_{1-3}$alkyl, —SO$_2$C$_{1-3}$alkyl, —SO$_2$(CH$_2$)$_{1-3}$OH, —SO$_2$(CH$_2$)$_{1-3}$CO$_2$C$_{1-3}$alkyl, —SO$_2$NH$_2$, —SO$_2$NHC$_{1-3}$alkyl, —SO$_2$N(diC$_{1-3}$alkyl), —SO$_2$NH(tetrahydropyran-4-yl) or —SO$_2$NH(CH$_2$)$_{2-3}$OH.

5. A compound chosen from

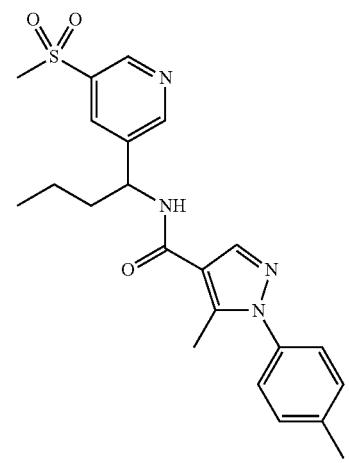

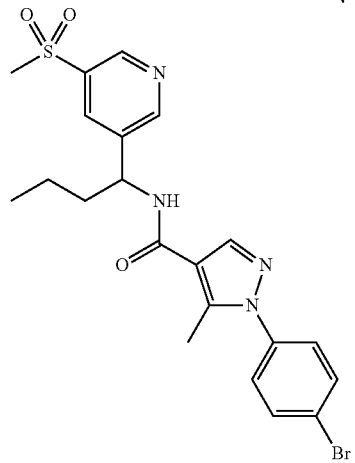

125
-continued
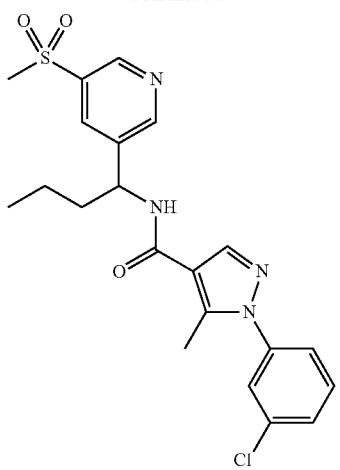
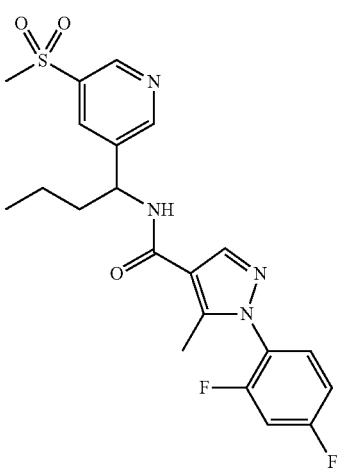
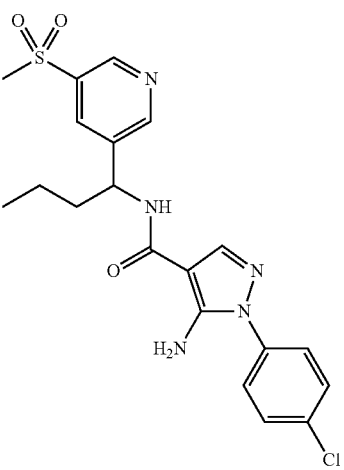
126
-continued
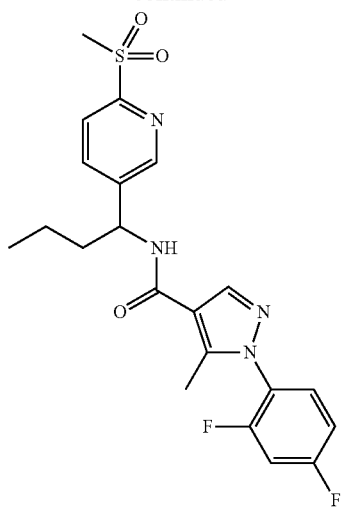
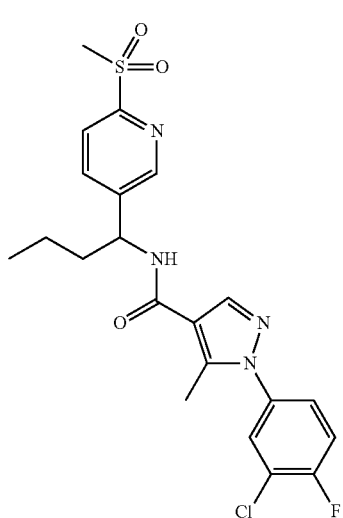
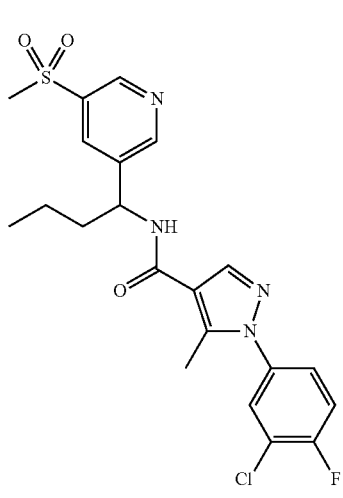

127
-continued
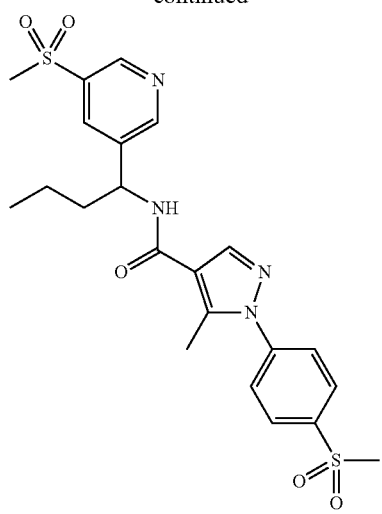
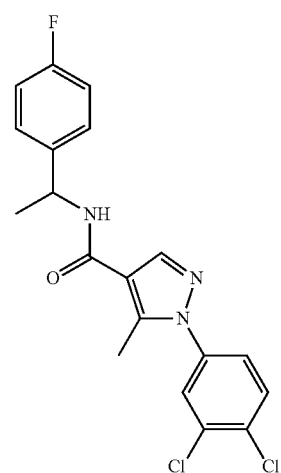
128
-continued
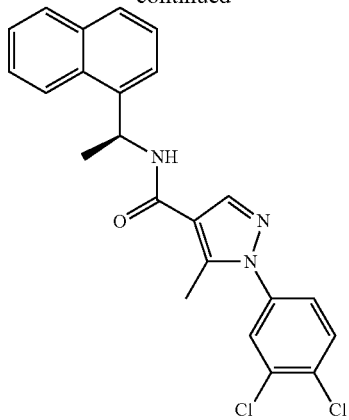
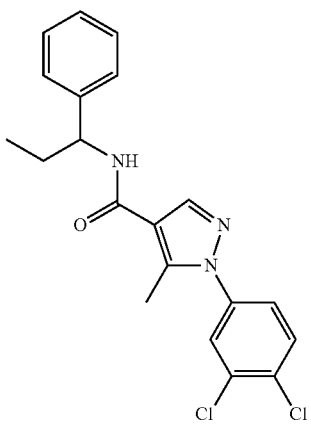
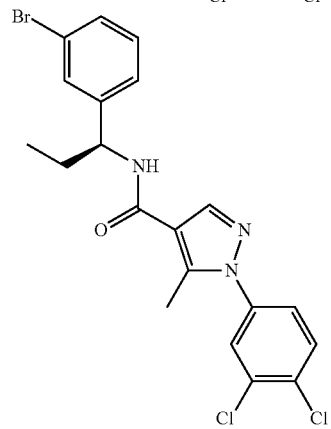
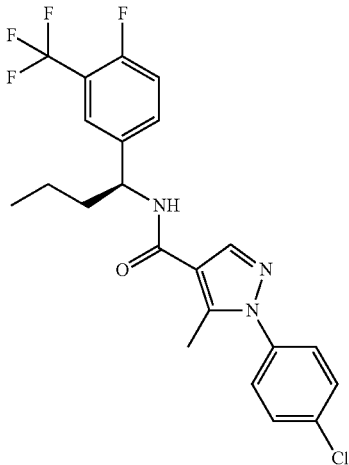

129
-continued
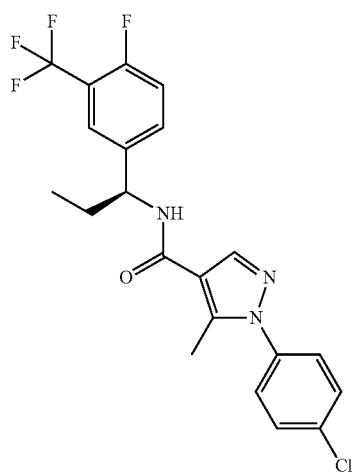
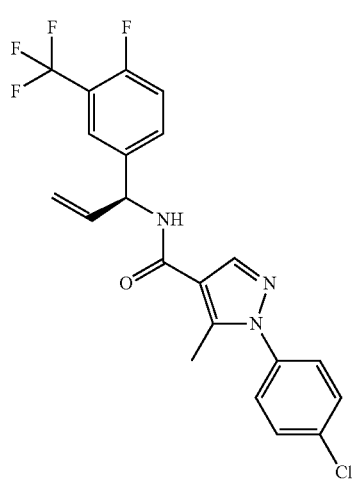
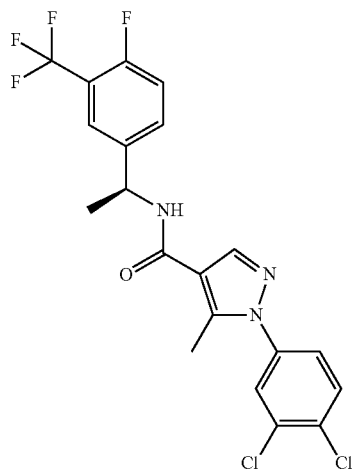
130
-continued
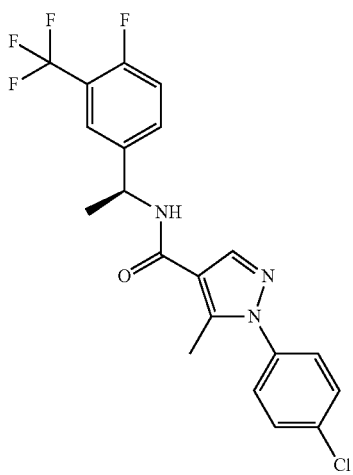
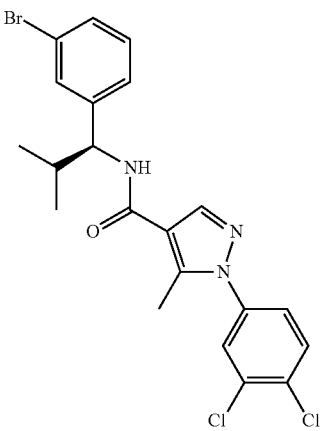
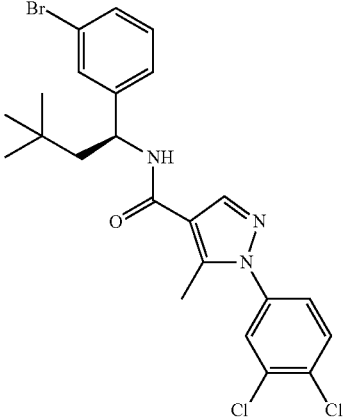

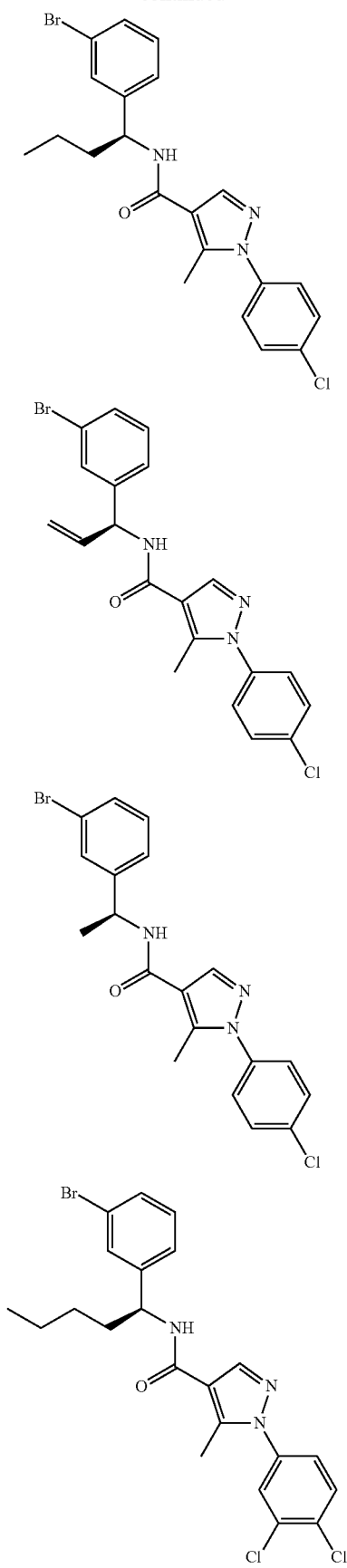
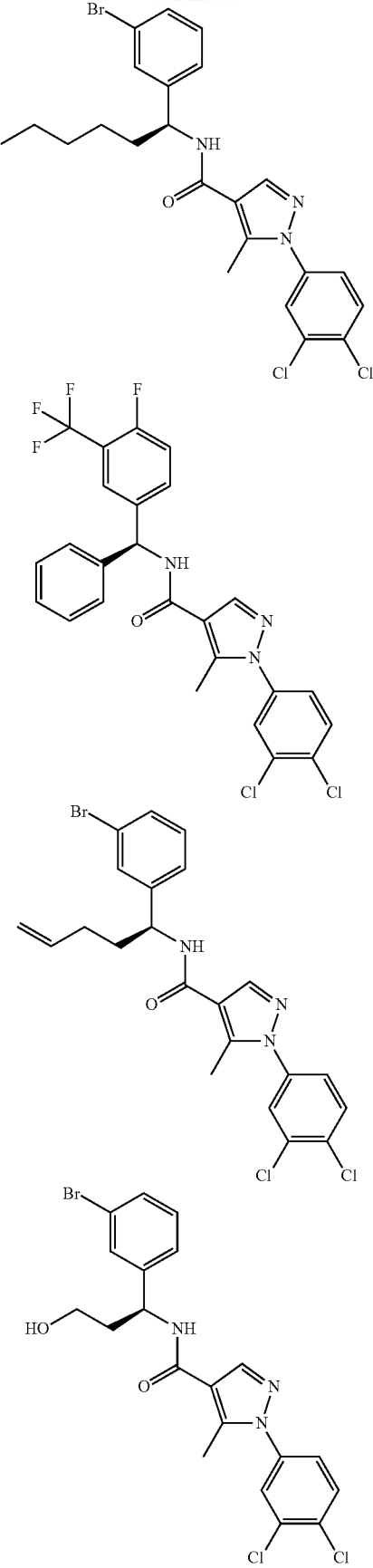

133
-continued
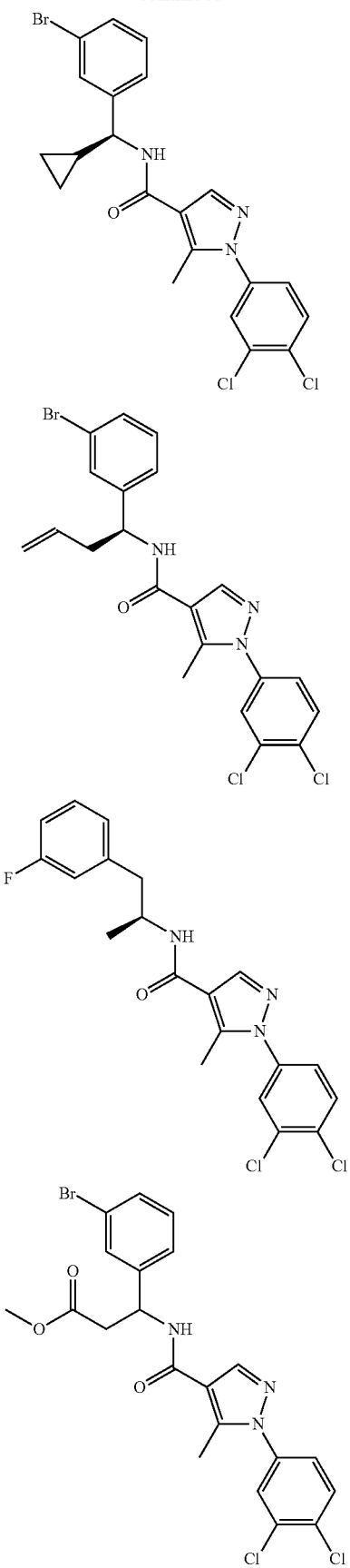
134
-continued
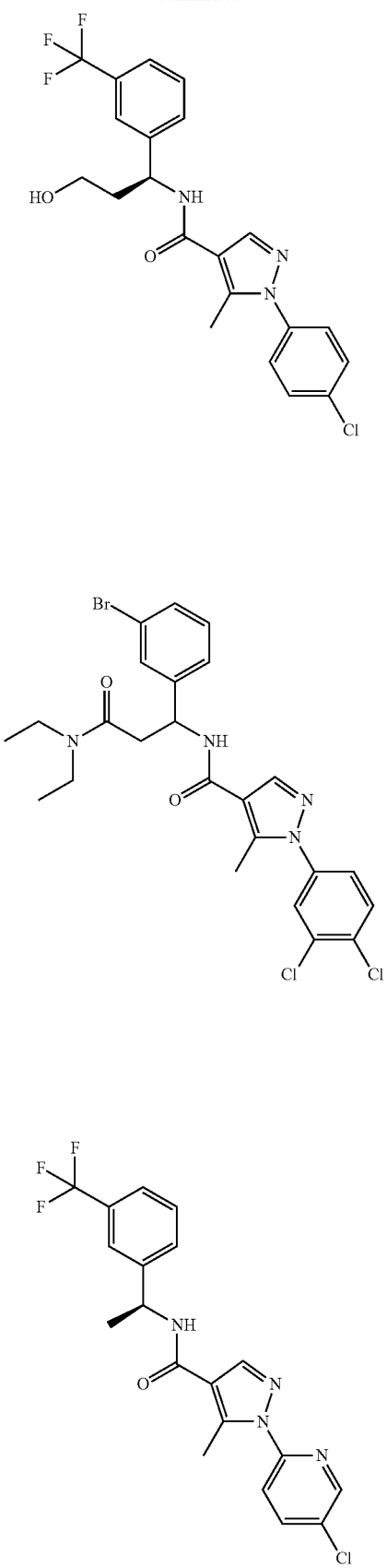

135
-continued
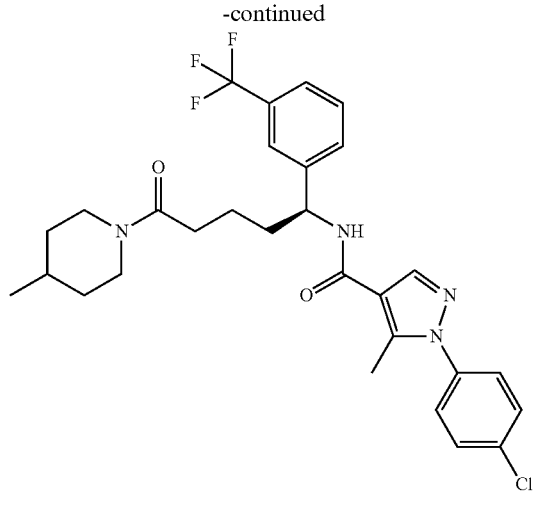
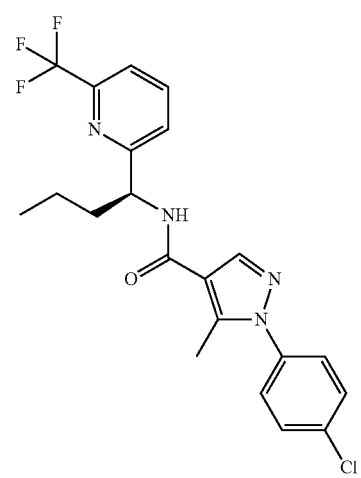
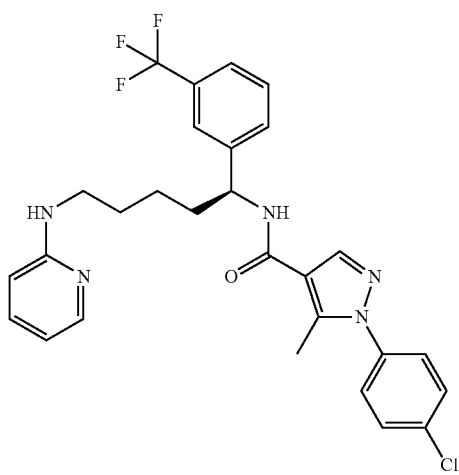
136
-continued
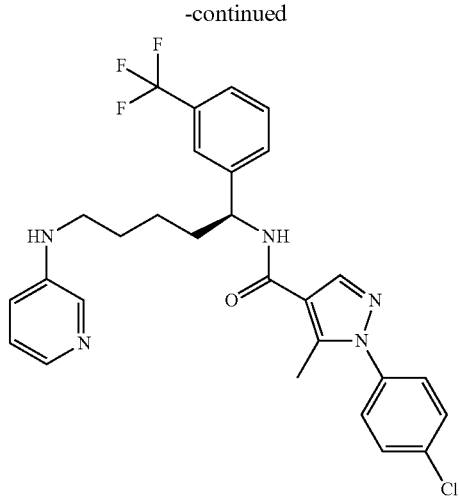
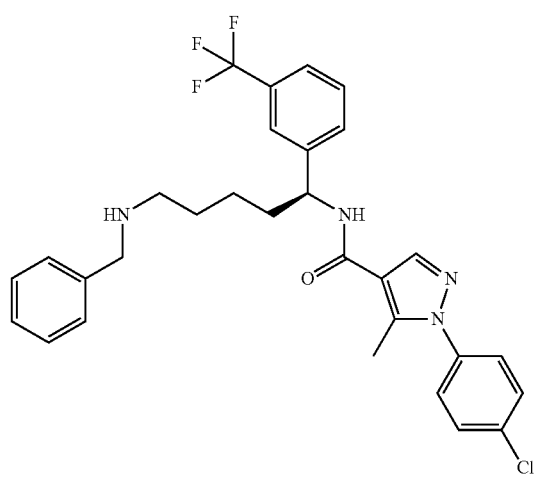
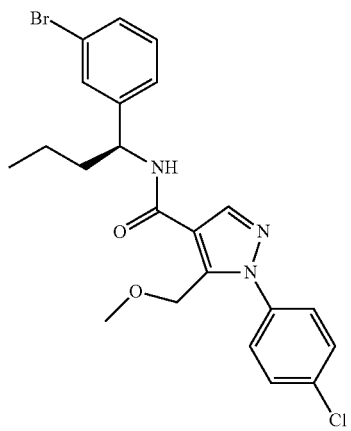

137
-continued
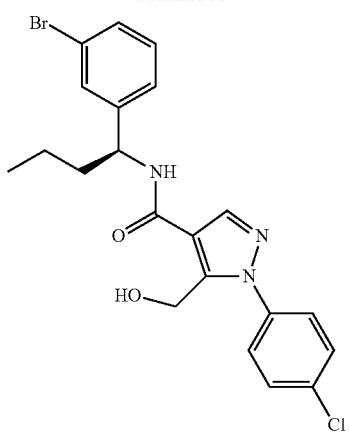
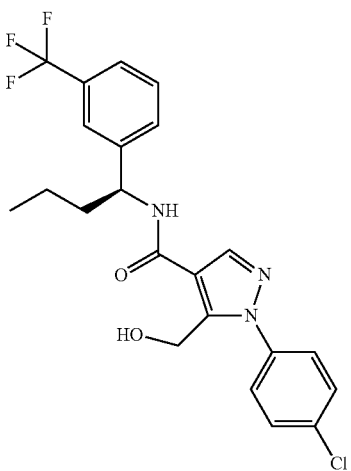
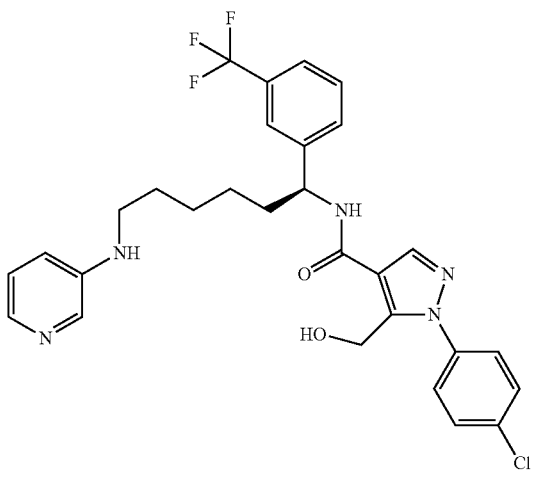
138
-continued
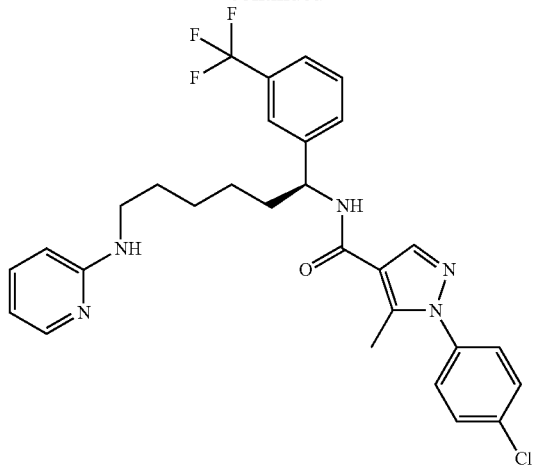
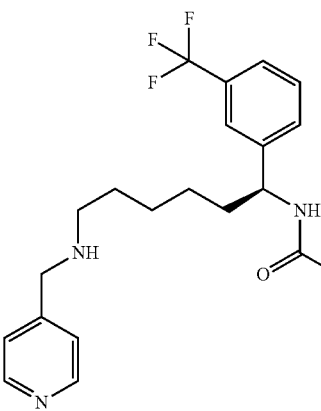
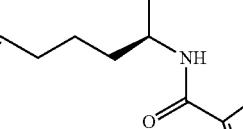

139
-continued
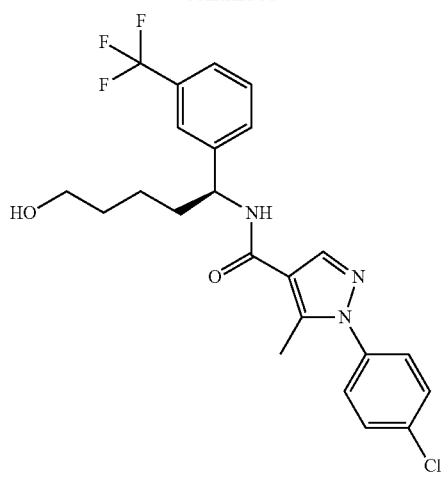
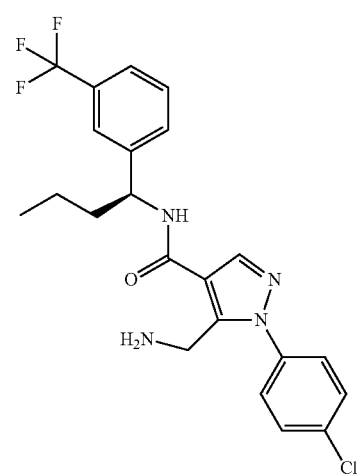
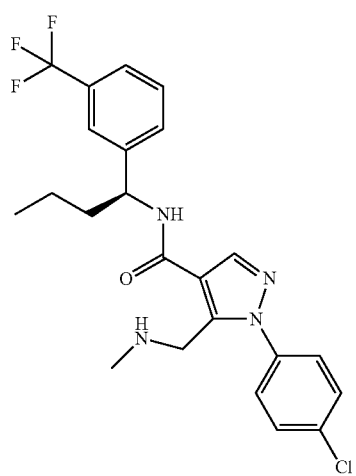
140
-continued
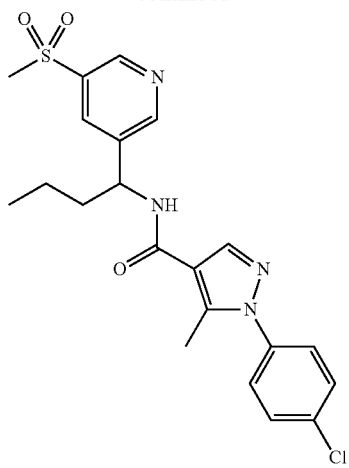
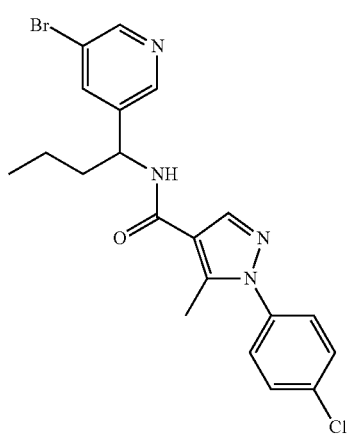
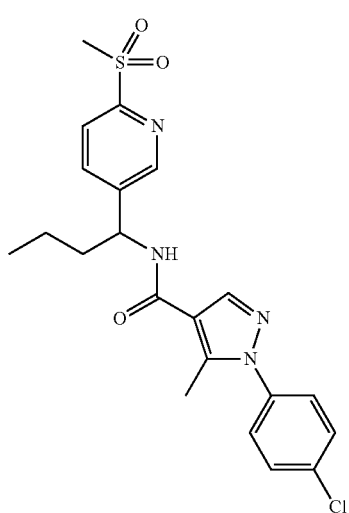

141
-continued
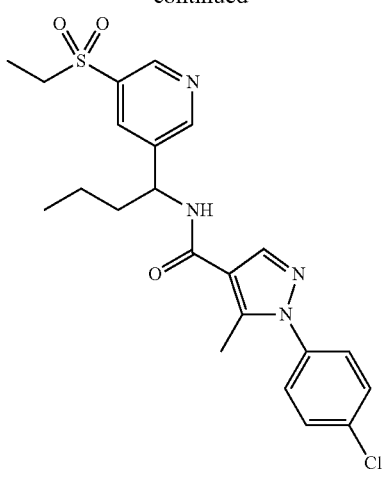
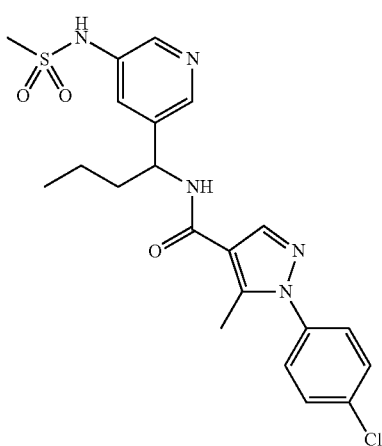
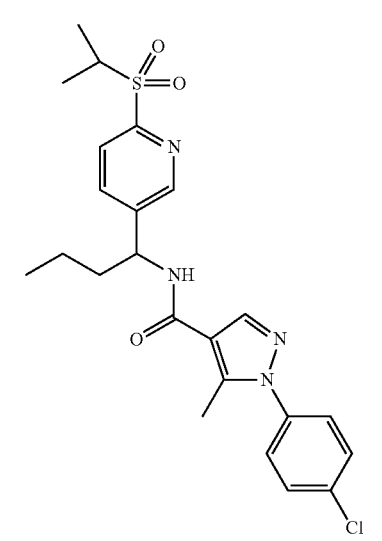
142
-continued
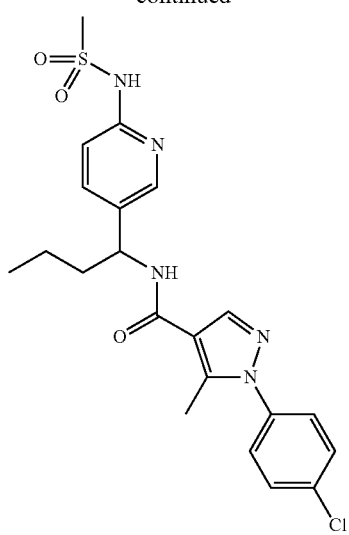
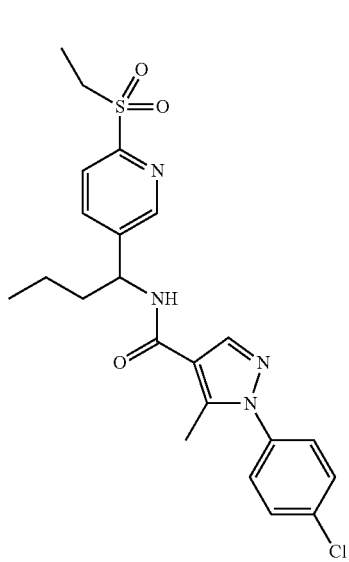
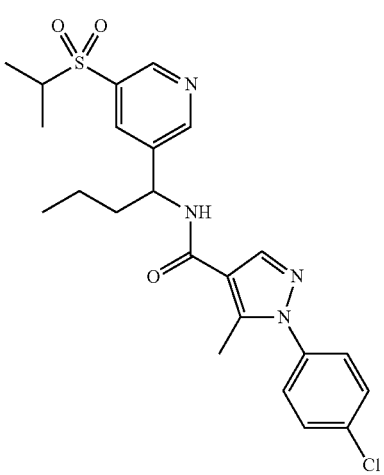

143
-continued
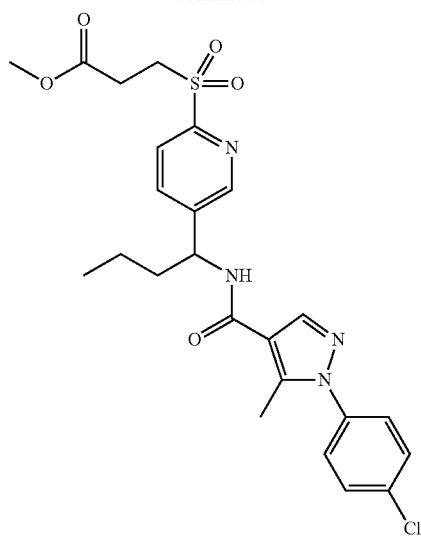
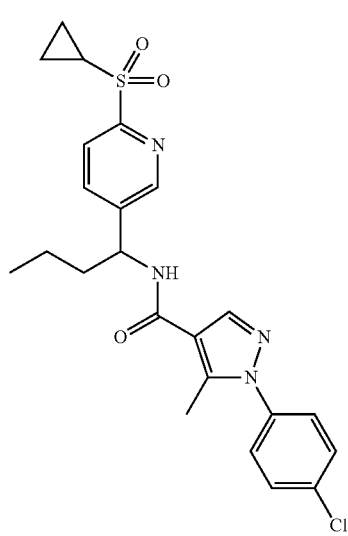
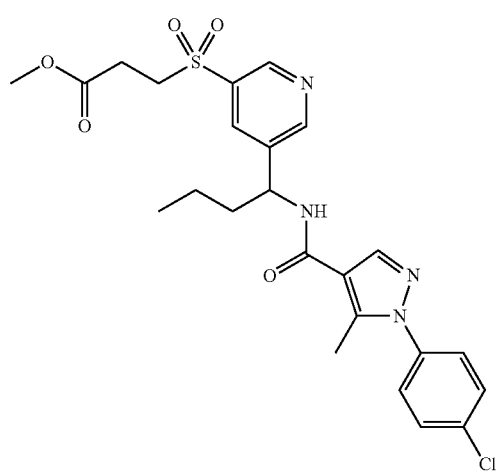
144
-continued
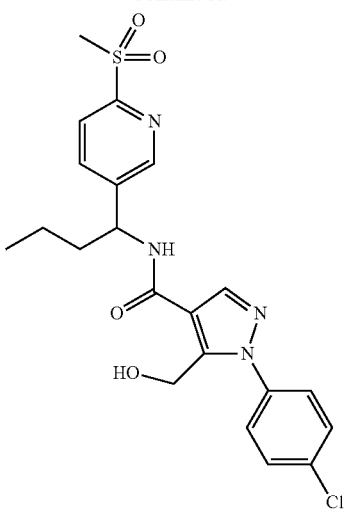
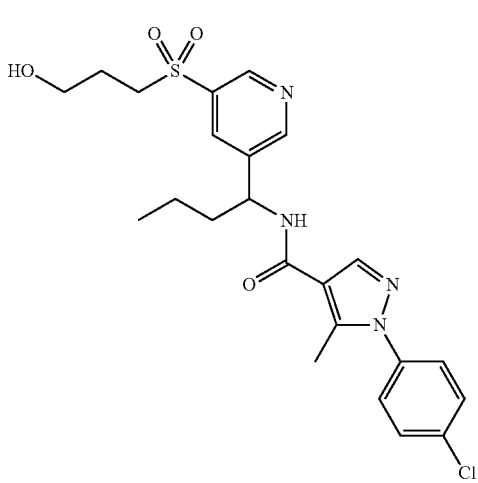
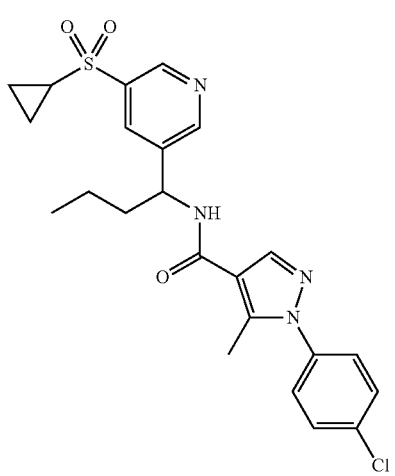

-continued

147 -continued

148 -continued

| 149 -continued | 150 -continued |
|---|---|
| 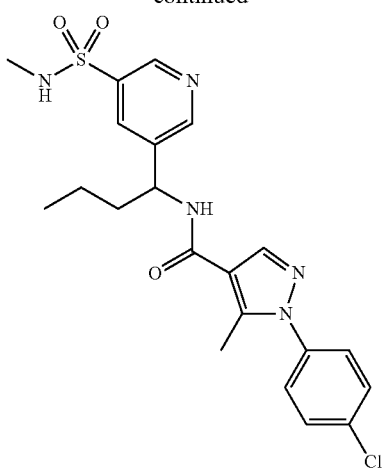 | 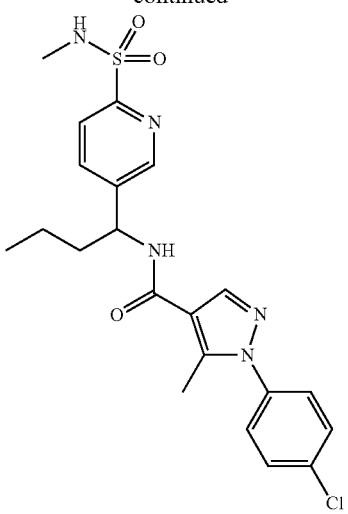 |
| 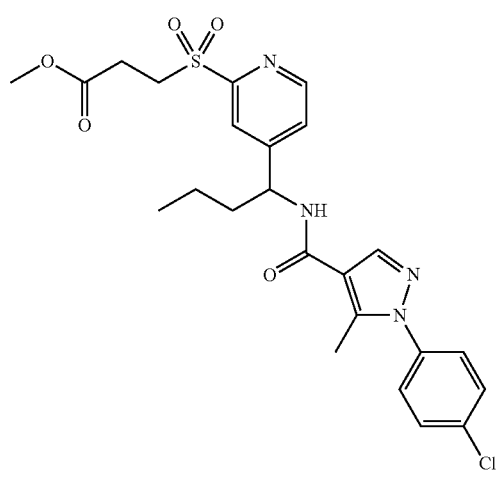 | 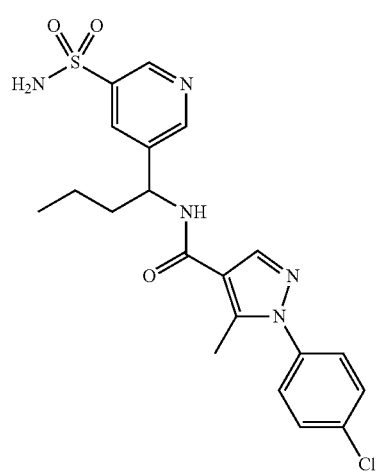 |
| 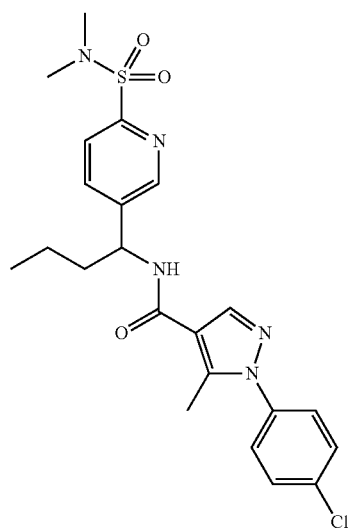 | 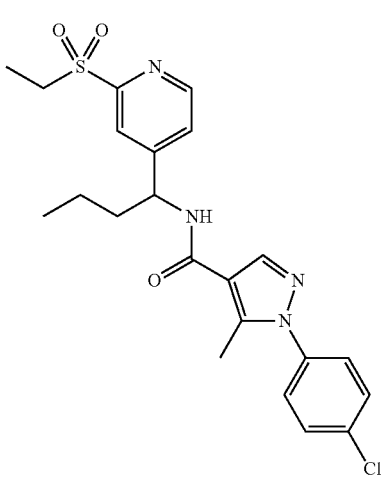 |

151
-continued
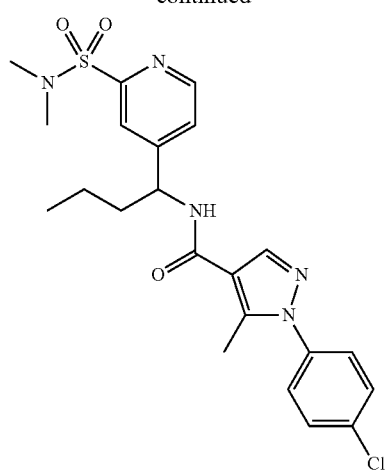
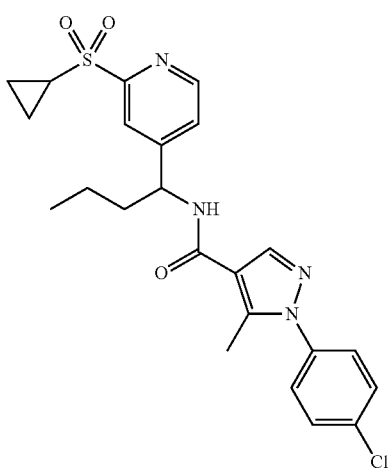
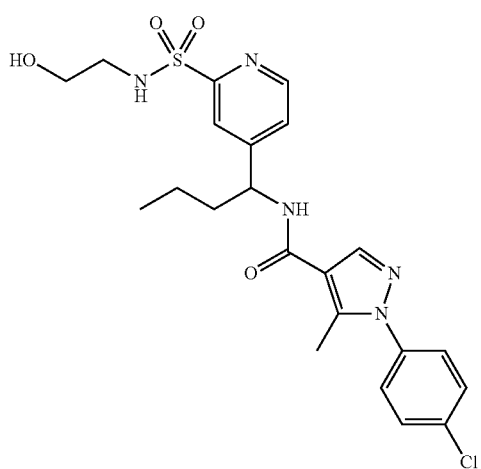
152
-continued
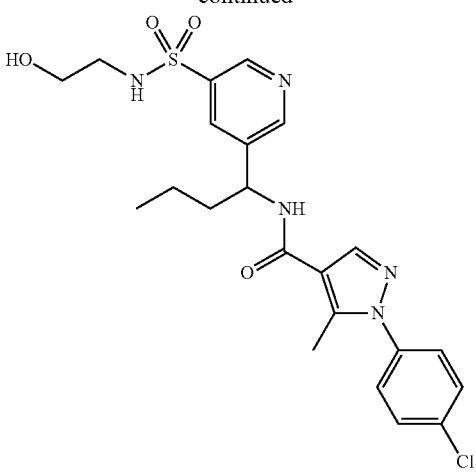
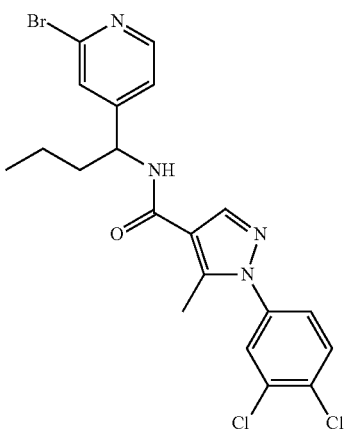
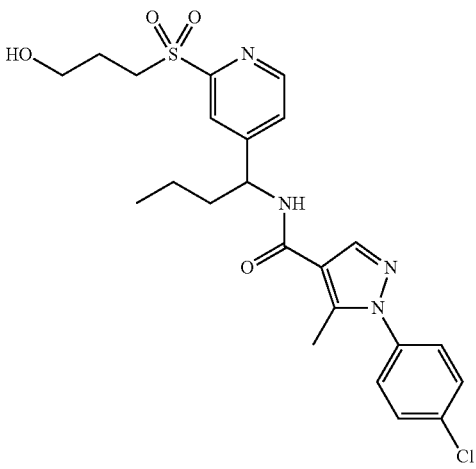

153
-continued
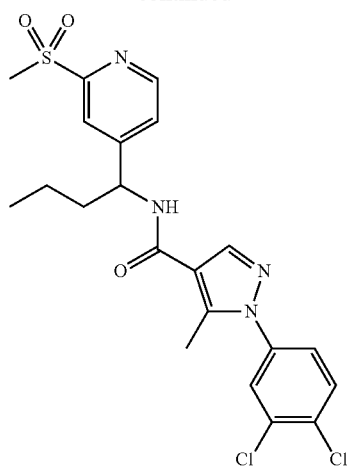
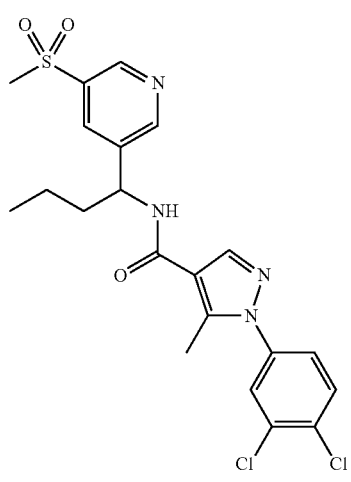
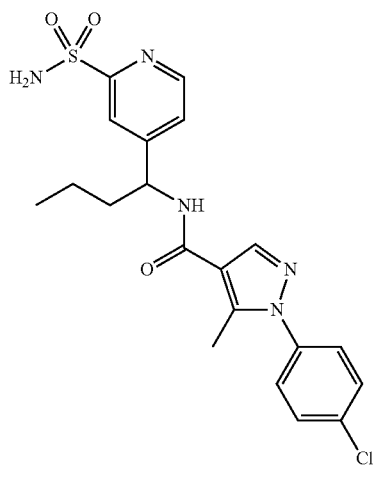
154
-continued
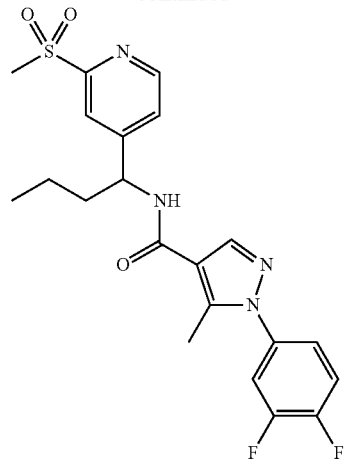
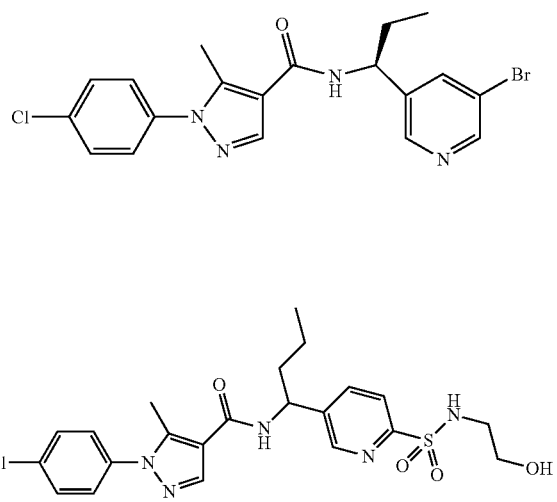
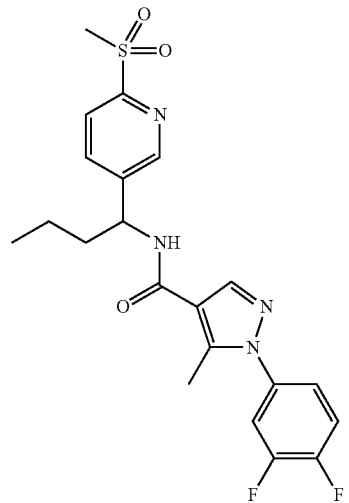

155
-continued
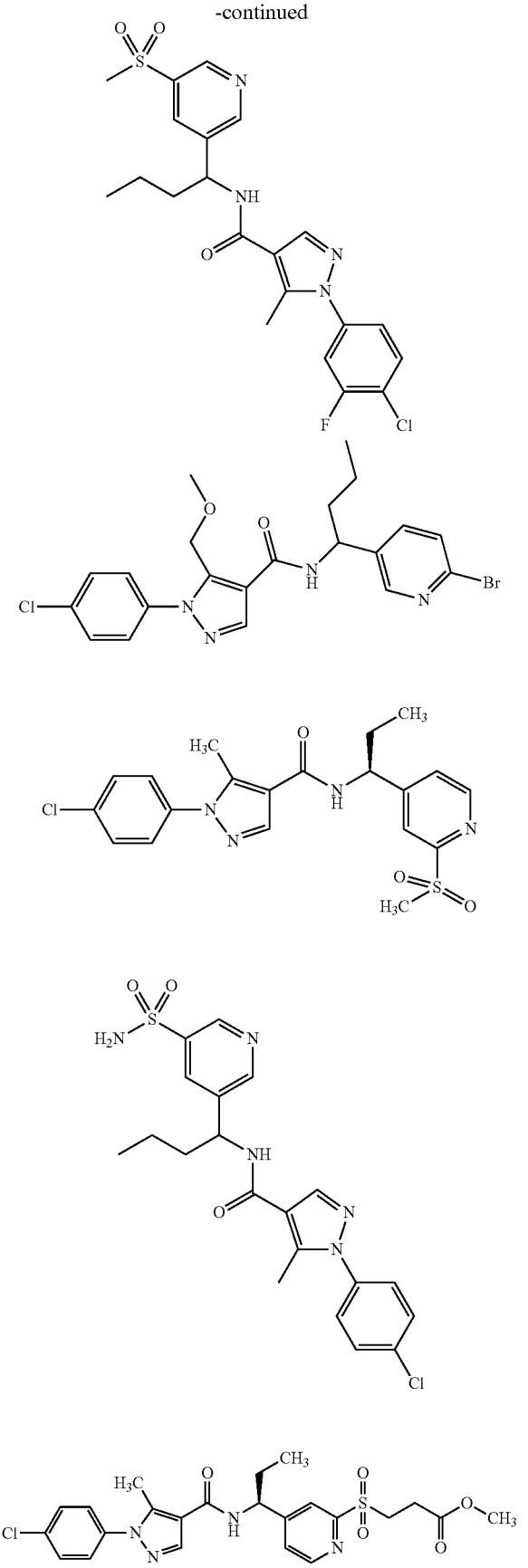
156
-continued
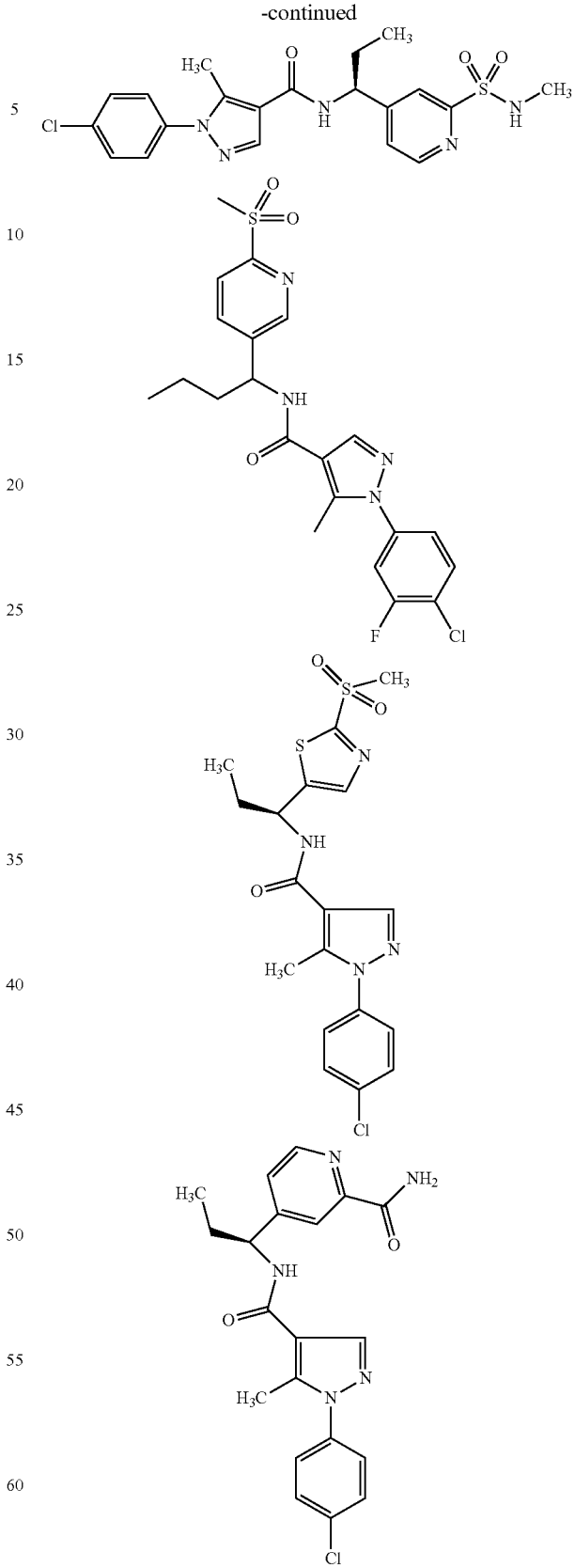
or a pharmaceutically acceptable salt thereof.

6. A pharmaceutical composition comprising a pharmaceutically effective amount of a compound according to claim 1.

7. A method of treating rheumatoid arthritis or multiple sclerosis, comprising administering to a patient a pharmaceutically effective amount of a compound according to claim 1.

8. The method according to claim 7 wherein the treatment is for rheumatoid arthritis.

9. The method according to claim 7 wherein the treatment is for multiple sclerosis.

* * * * *